United States Patent
Tanaka et al.

(10) Patent No.: US 10,696,637 B2
(45) Date of Patent: Jun. 30, 2020

(54) NITROGEN-CONTAINING HETEROCYCLIC COMPOUND

(71) Applicants: FUJIFILM Corporation, Minato-Ku, Tokyo (JP); FUJIFILM Toyama Chemical Co., Ltd., Tokyo (JP)

(72) Inventors: Tadashi Tanaka, Toyama (JP); Masataka Fujino, Toyama (JP); Kentaro Furuya, Toyama (JP)

(73) Assignees: FUJIFILM Corporation, Tokyo (JP); FUJIFILM Toyama Chemical Co., Ltd., Tokyo (JP)

( * ) Notice: Subject to any disclaimer, the term of this patent is extended or adjusted under 35 U.S.C. 154(b) by 0 days.

(21) Appl. No.: 15/743,758

(22) PCT Filed: Jul. 15, 2016

(86) PCT No.: PCT/JP2016/071047
§ 371 (c)(1),
(2) Date: Jan. 11, 2018

(87) PCT Pub. No.: WO2017/014201
PCT Pub. Date: Jan. 26, 2017

(65) Prior Publication Data
US 2019/0077761 A1    Mar. 14, 2019

(30) Foreign Application Priority Data

Jul. 17, 2015 (JP) .................. 2015-143503
Feb. 4, 2016 (JP) .................. 2016-019782

(51) Int. Cl.
| | | |
|---|---|---|
| *C07D 215/48* | (2006.01) | |
| *C07D 401/14* | (2006.01) | |
| *C07D 215/38* | (2006.01) | |
| *C07D 401/04* | (2006.01) | |
| *C07D 401/12* | (2006.01) | |
| *C07D 409/12* | (2006.01) | |
| *C07D 215/42* | (2006.01) | |
| *C07D 401/06* | (2006.01) | |
| *C07D 405/14* | (2006.01) | |
| *C07D 413/04* | (2006.01) | |
| *C07D 413/14* | (2006.01) | |
| *A61K 31/444* | (2006.01) | |
| *A61K 31/4704* | (2006.01) | |
| *A61K 31/4709* | (2006.01) | |
| *A61K 31/4725* | (2006.01) | |
| *A61K 31/498* | (2006.01) | |
| *A61K 31/5377* | (2006.01) | |
| *A61P 37/02* | (2006.01) | |

(52) U.S. Cl.
CPC .......... *C07D 215/48* (2013.01); *A61K 31/444* (2013.01); *A61K 31/4704* (2013.01); *A61K 31/4709* (2013.01); *A61K 31/4725* (2013.01); *A61K 31/498* (2013.01); *A61K 31/5377* (2013.01); *A61P 37/02* (2018.01); *C07D 215/38* (2013.01); *C07D 215/42* (2013.01); *C07D 401/04* (2013.01); *C07D 401/06* (2013.01); *C07D 401/12* (2013.01); *C07D 401/14* (2013.01); *C07D 405/14* (2013.01); *C07D 409/12* (2013.01); *C07D 413/04* (2013.01); *C07D 413/14* (2013.01); *Y02P 20/55* (2015.11)

(58) Field of Classification Search
None
See application file for complete search history.

(56) References Cited

U.S. PATENT DOCUMENTS

| 5,378,694 A | 1/1995 | Afonso et al. |
| 5,457,099 A | 10/1995 | Shogaki et al. |

(Continued)

FOREIGN PATENT DOCUMENTS

| CN | 102143949 A | 8/2011 |
| EA | 007464 B1 | 10/2006 |

(Continued)

OTHER PUBLICATIONS

Clark, Peter G. K. LP99: Discovery and Synthesis of the First Selective BRD7/9 Bromodomain Inhibitor. Angew. Chem. Int. Ed. 2015, 54, 6217-6221.*

Kelland, E. E., et al., "In vitro assessment of the direct effect of laquinimod on basic functions of human neural stem cells and oligodendrocyte progenitor cells", Journal of the Neurological Sciences, 2014, pp. 66-74, vol. 346, No. 1-2.

International Search Report dated Aug. 30, 2016 for International application No. PCT/JP2016/071047.

(Continued)

*Primary Examiner* — Samantha L Shterengarts
(74) *Attorney, Agent, or Firm* — Sughrue Mion, PLLC

(57) ABSTRACT

A compound represented by the general formula, or a salt thereof, has exceptional CXCL10 inhibitory activity and is useful as a treatment agent for the prevention and/or treatment, etc., of diseases involving overproduction of CXCL10. In the formula: $R^1$ is a $C_{1-6}$ alkyl group, etc.; $R^2$ is a hydrogen atom, etc.; $R^3$ is a halogen atom, etc.; $Z^1$, $Z^2$, and $Z^3$ are CH, etc.; $X^1$ is CONH, etc.; ring A is a phenyl group, etc.; $R^4$ is a halogen atom, etc.; and m is an integer of 0-5.

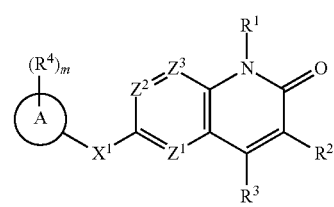

17 Claims, No Drawings

(56) References Cited

U.S. PATENT DOCUMENTS

| | | | |
|---|---|---|---|
| 6,509,352 | B1 | 1/2003 | Inaba et al. |
| 2004/0082592 | A1 | 4/2004 | Mabire et al. |
| 2004/0235848 | A1 | 11/2004 | Okuzumi et al. |
| 2010/0286127 | A1 | 11/2010 | Miyoshi et al. |
| 2010/0331326 | A1 | 12/2010 | Bock et al. |
| 2019/0314360 | A1 | 10/2019 | Makita et al. |

FOREIGN PATENT DOCUMENTS

| | | |
|---|---|---|
| JP | 6-73011 A | 3/1994 |
| JP | 6-502845 A | 3/1994 |
| JP | 7-252228 A | 10/1995 |
| TW | 515794 B | 1/2003 |
| WO | 02/051834 A1 | 7/2002 |
| WO | 02/051835 A1 | 7/2002 |
| WO | 2003/053926 A1 | 7/2003 |
| WO | 2004/005892 A2 | 1/2004 |
| WO | 2005/018573 A2 | 3/2005 |
| WO | 2009/041026 A1 | 4/2009 |
| WO | 2009/084693 A1 | 7/2009 |
| WO | 2010/028015 A2 | 3/2010 |
| WO | 2013/027168 A1 | 2/2013 |
| WO | 2014/159837 A1 | 10/2014 |
| WO | 2016/016316 A1 | 2/2016 |
| WO | 2016/077656 A2 | 5/2016 |

OTHER PUBLICATIONS

Written Opinion dated Aug. 30, 2016 for International application No. PCT/JP2016/071047.

International Preliminary Report on Patentability dated Jan. 23, 2018 for International application No. PCT/JP2016/071047.

Extended European Search Report (EESR) dated Feb. 26, 2019, from the European Patent Office in counterpart European Application No. 16827761.4.

English translation of WO 2009/041026.

International Preliminary Report on Patentability dated Jul. 2, 2019 from the International Bureau in counterpart International Application No. PCT/JP2017/046901 (corresponds to U.S. Appl. No. 16/453,393).

International Search Report dated Apr. 10, 2018 from the International Searching Authority in counterpart International Application No. PCT/JP2017/046901 (corresponds to U.S. Appl. No. 16/453,393).

Panagis Filippakopoulos et al., "Targeting bromodomains: epigenetic readers of lysine acetylation", Nature Reviews, Drug Discovery, vol. 13, May 2014, pp. 337-356.

Takayoshi Suzuki, "Development of Epigenetic Modulators for Cancer Therapy", Magazine of Kyoto Prefectural University of Medicine, vol. 124, No. 12, 2015, pp. 839-847.

Written Opinion dated Apr. 10, 2018 from the International Bureau in counterpart International Application No. PCT/JP2017/046901 (corresponds to U.S. Appl. No. 16/453,393).

Office Action dated Jun. 14, 2019, from the Intellectual Property Office of Singapore in counterpart Singapore Application No. 11201800445P.

Office Action dated Dec. 18, 2019 in Russian Application No. 2018105867.

Extended European Search Report dated Nov. 22, 2019 from the European Patent Office in EP Application No. 17885921.1 (corresponds to U.S. Appl. No. 16/453,393).

Igoe et al., "Design of a Biased Potent Small Molecule Inhibitor of the Bromodomain and PHD Finger-Containing (BRPF) Proteins Suitable for Cellular and in Vivo Studies", Journal of Medicinal Chemistry, 2017, vol. 60, No. 2, pp. 668-680 (total 13 pages).

Office Action dated Jan. 28, 2020 from the Intellectual Property India Patent Office in Indian Application 201947025350, corresponding to subject-matter related U.S. Appl. No. 16/453,393.

Elena Ferri, et al.,"Bromodomains: Structure, function and pharmacology of inhibition", Biochemical Pharmacology, 2015, one page, https://doi.org/10.1016/j.bcp.2015.12.005.

Office Action dated Mar. 10, 2020 from the Taiwan Intellectual Property Office in corresponding Taiwan patent application No. 105122410; 4 pages.

Office Action dated Mar. 13, 2020, in Russian Application No. 2019119836; 14 pages, corresponding to subject matter-related U.S. Appl. No. 16/453,393.

Office Action in Japanese Application No. 2018-559578 dated Apr. 28, 2020; 6 pages total with translation, corresponds to subject-matter related to U.S. Appl. No. 16/453,393.

* cited by examiner

NITROGEN-CONTAINING HETEROCYCLIC COMPOUND

CROSS REFERENCE TO RELATED APPLICATIONS

This application is a National Stage of International Application No. PCT/JP2016/071047 filed Jul. 15, 2016, claiming priority based on Japanese Patent Application No. 2015-143503 filed Jul. 17, 2015 and Japanese Patent Application No. 2016-019782 filed Feb. 4, 2016, the contents of all of which are incorporated herein by reference in their entirety.

TECHNICAL FIELD

The present invention relates to a nitrogen-containing heterocyclic compound that is useful as a chemokine CXCL10 inhibitor.

BACKGROUND ART

CXCL10 (C—X—C motif chemokine 10) is a CXC chemokine also known as IP-10 (interferon gamma inducible protein 10). Upon partial damage of living tissues by infection or the like, chemotactic factors such as CXCL10 and MCP-1 (monocyte chemotactic protein-1) are produced. As a result, monocytes, lymphocytes and neutrophils are infiltrated into inflammatory tissues.

It has been suggested that immune diseases such as inflammatory bowel disease, arthritis, psoriasis, systemic sclerosis, systemic lupus erythematosus and autoimmune neuroinflammatory disease develop due to the increased production of CXCL10. Therefore, a compound having an excellent CXCL10 inhibitory activity is considered to be useful as an agent for treatment such as prophylaxis and/or therapy of a disease involving the overproduction of CXCL10 (Patent Literature 1).

PRIOR ART DOCUMENTS

Patent Document

Patent Document 1: International Publication No. WO 2009/041026

SUMMARY OF INVENTION

Technical Problem

There has been a demand for a compound that has an excellent CXCL10 inhibitory activity and is useful as an agent for treatment such as prophylaxis and/or therapy of a disease involving the overproduction of CXCL10.

An object of the present invention is to provide a compound that has an excellent CXCL10 inhibitory activity and is useful as an agent for treatment such as prophylaxis and/or therapy of a disease involving the overproduction of CXCL10.

Solution to Problem

Under these circumstances, the present inventors have conducted diligent studies and consequently completed the present invention by finding that a nitrogen-containing heterocyclic compound shown below has an excellent CXCL10 inhibitory activity and is useful as an agent for treatment such as prophylaxis and/or therapy of a disease involving the overproduction of CXCL10.

Thus, the present invention provides the following:

<1>

A compound represented by the general formula [1] or a salt thereof:

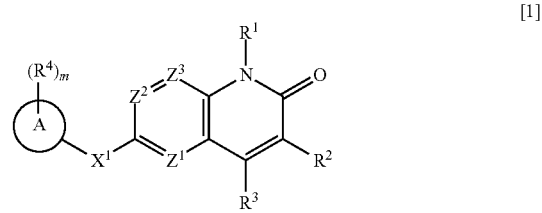

[1]

wherein
$R^1$ represents an optionally substituted $C_{1-6}$ alkyl group;
$R^2$ represents a hydrogen atom, a halogen atom or an optionally substituted $C_{1-6}$ alkyl group;
$R^3$ represents a halogen atom, an optionally substituted $C_{1-6}$ alkyl group, an optionally substituted $C_{2-6}$ alkenyl group, an optionally substituted $C_{3-8}$ cycloalkyl group, an optionally substituted $C_{4-8}$ cycloalkenyl group, an optionally substituted aryl group, an optionally substituted $C_{1-6}$ alkoxy group, an optionally substituted $C_{1-6}$ alkylamino group, an optionally substituted di($C_{1-6}$ alkyl)amino group or an optionally substituted heterocyclic group;
$Z^1$, $Z^2$ and $Z^3$ are the same or different and each represent a nitrogen atom or a group represented by the general formula $CR^5$ wherein $R^5$ represents a hydrogen atom, a halogen atom or an optionally substituted $C_{1-6}$ alkyl group;
$X^1$ represents
(1) a group represented by the general formula $C(=O)N(R^6)$ wherein the carbon atom is bonded to ring A, and $R^6$ represents a hydrogen atom, an amino-protective group or an optionally substituted $C_{1-6}$ alkyl group,
(2) a group represented by the general formula $N(R^7)C(=O)$ wherein the nitrogen atom is bonded to ring A, and $R^7$ represents a hydrogen atom, an amino-protective group or an optionally substituted $C_{1-6}$ alkyl group; or $R^7$ represents, together with one substituent $R^4$ on ring A, an optionally substituted $C_{2-4}$ alkylene group, a group represented by the general formula $O—Y^1$ wherein the oxygen atom is bonded to ring A, and $Y^1$ represents an optionally substituted $C_{1-3}$ alkylene group, a group represented by the general formula $S(O)_n—Y^2$ wherein the sulfur atom is bonded to ring A, $Y^2$ represents an optionally substituted $C_{1-3}$ alkylene group, and n represents an integer of 0 to 2, or a group represented by the general formula $N(R^8)—Y^3$ wherein the nitrogen atom is bonded to ring A, $Y^3$ represents an optionally substituted $C_{1-3}$ alkylene group, and $R^8$ represents a hydrogen atom, an amino-protective group, an optionally substituted $C_{3-6}$ alkyl group or an optionally substituted aryl group,
(3) an optionally substituted divalent cyclic hydrocarbon group resulting from the removal of one hydrogen atom from each of two adjacent atoms or
(4) an optionally substituted divalent heterocyclic group resulting from the removal of one hydrogen atom from each of two adjacent atoms;
ring A represents a cyclic hydrocarbon group or a heterocyclic group;
m number of $R^4$ are the same or different and each represent a halogen atom, a cyano group, a nitro group, an amino-protective group, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{4-8}$ cycloalkenyl group, an optionally substituted aryl group, an optionally substituted $C_{1-6}$ alkoxy group, an optionally substituted aryloxy group, an optionally substituted $C_{1-6}$ alkylamino group, an optionally substituted di($C_{1-6}$ alkyl)amino group, an optionally substituted arylamino group, an optionally substituted carbamoyl group, an optionally substituted sulfamoyl group, an optionally substituted $C_{1-6}$ alkylthio group, an optionally substituted arylthio group, an optionally substituted $C_{1-6}$ alkylsulfonyl group, an optionally substituted arylsulfonyl group, an optionally substituted heterocyclic group, an optionally protected amino group, an optionally protected hydroxyl group, an optionally protected carboxyl group, an optionally substituted $C_{2-5}$ alkylene group formed together by two adjacent $R^4$, an optionally substituted $C_{2-4}$ alkylene group formed together by one $R^4$ and $R^7$, a group represented by the general formula $O-Y^1$ formed together by one $R^4$ and $R^7$ wherein the oxygen atom is bonded to ring A, and $Y^1$ represents an optionally substituted $C_{1-3}$ alkylene group, a group represented by the general formula $S(O)_n-Y^2$ formed together by one $R^4$ and $R^7$ wherein the sulfur atom is bonded to ring A, $Y^2$ represents an optionally substituted $C_{1-3}$ alkylene group, and n represents an integer of 0 to 2, or a group represented by the general formula $N(R^8)-Y^3$ formed together by one $R^4$ and $R^7$ wherein the nitrogen atom is bonded to ring A, $Y^3$ represents an optionally substituted $C_{1-3}$ alkylene group, and $R^8$ represents a hydrogen atom, an amino-protective group, an optionally substituted $C_{1-6}$ alkyl group or an optionally substituted aryl group; and m represents an integer of 0 to 5.

<2>

The compound according to <1> or a salt thereof, wherein $R^2$ is a hydrogen atom or an optionally substituted $C_{1-6}$ alkyl group; and each of $Z^1$, $Z^2$ and $Z^3$ is CH.

<3>

The compound according to <1> or <2> or a salt thereof, wherein $R^1$ is a $C_{1-3}$ alkyl group, and $R^3$ is an optionally substituted $C_{1-6}$ alkyl group, an optionally substituted $C_{3-8}$ cycloalkyl group, an optionally substituted aryl group or an optionally substituted heterocyclic group.

<4>

The compound according to any one of <1> to <3> or a salt thereof, wherein ring A is a cyclic hydrocarbon group.

<5>

The compound according to any one of <1> to <4> or a salt thereof, wherein $X^1$ is a group represented by the general formula $C(=O)N(R^6)$ wherein the carbon atom is bonded to ring A, and $R^6$ represents a hydrogen atom, an amino-protective group or an optionally substituted $C_{1-6}$ alkyl group.

<6>

The compound according to any one of <1> to <4> or a salt thereof, wherein $X^1$ is a group represented by the general formula $C(=O)N(R^{6a})$ wherein the carbon atom is bonded to ring A, and $R^{6a}$ represents a hydrogen atom or an optionally substituted $C_{1-3}$ alkyl group;

m number of $R^4$ are the same or different and each are a halogen atom, an optionally substituted $C_{1-3}$ alkyl group, an optionally substituted $C_{1-3}$ alkylamino group or an optionally protected amino group; and m is an integer of 0 to 2.

<7>

The compound according to any one of <1> to <4> or a salt thereof, wherein $R^3$ is an optionally substituted $C_{1-6}$ alkyl group, an optionally substituted $C_{3-8}$ cycloalkyl group or an optionally substituted heterocyclic group;

$X^1$ is a group represented by the general formula $C(=O)N(R^{6b})$ wherein the carbon atom is bonded to ring A, and $R^{6b}$ represents an optionally substituted $C_{1-3}$ alkyl group;

m number of $R^4$ are the same or different and each are a halogen atom or an optionally substituted $C_{1-3}$ alkyl group; and m is an integer of 0 to 2.

<8>

The compound according to <7> or a salt thereof, wherein m number of $R^4$ are the same or different and each are a halogen atom; and m is an integer of 0 to 2.

<9>

The compound according to any one of <1> to <4> or a salt thereof, wherein $X^1$ is a group represented by the general formula $N(R^7)C(=O)$ wherein the nitrogen atom is bonded to ring A, and $R^7$ represents a hydrogen atom, an amino-protective group or an optionally substituted $C_{1-6}$ alkyl group; or $R^7$ represents, together with one substituent $R^4$ on ring A, an optionally substituted $C_{2-4}$ alkylene group, a group represented by the general formula $O-Y^1$ wherein the oxygen atom is bonded to ring A, and $Y^1$ represents an optionally substituted $C_{1-3}$ alkylene group, a group represented by the general formula $S(O)_n-Y^2$ wherein the sulfur atom is bonded to ring A, $Y^2$ represents an optionally substituted $C_{1-3}$ alkylene group, and n represents an integer of 0 to 2, or a group represented by the general formula $N(R^8)-Y^3$ wherein the nitrogen atom is bonded to ring A, $Y^3$ represents an optionally substituted $C_{1-3}$ alkylene group, and $R^8$ represents a hydrogen atom, an amino-protective group, an optionally substituted $C_{1-6}$ alkyl group or an optionally substituted aryl group.

<10>

The compound according to any one of <1> to <4> or a salt thereof, wherein $R^3$ is an optionally substituted $C_{1-6}$ alkyl group, an optionally substituted $C_{3-8}$ cycloalkyl group or an optionally substituted heterocyclic group;

$X^1$ is a group represented by the general formula $N(R^{7a})C(=O)$ wherein the nitrogen atom is bonded to ring A, and $R^{7a}$ represents an optionally substituted $C_{1-3}$ alkyl group, or $R^{7a}$ represents, together with one substituent $R^4$ on ring A, an optionally substituted $C_{2-3}$ alkylene group or a group represented by the general formula $O-Y^{1a}$ wherein the oxygen atom is bonded to ring A, and $Y^{1a}$ represents an ethylene group;

m number of $R^4$ are the same or different and each are a halogen atom, an optionally substituted $C_{1-3}$ alkyl group, an optionally substituted $C_{1-3}$ alkylsulfonyl group, an optionally substituted $C_{2-3}$ alkylene group formed together by two adjacent $R^4$, an optionally substituted $C_{2-3}$ alkylene group formed together by one $R^4$ and $R^{7a}$, or a group represented by the general formula $O-Y^{1a}$ formed together by one $R^4$ and $R^{7a}$ wherein the oxygen atom is bonded to ring A, and $Y^{1a}$ represents an ethylene group; and m is an integer of 0 to 2.

<11>

The compound according to any one of <1> to <4> or a salt thereof, wherein $R^3$ is an optionally substituted heterocyclic group;

$X^1$ is a group represented by the general formula $N(R^{7b})C(=O)$ wherein the nitrogen atom is bonded to ring A, and $R^{7b}$ represents an optionally substituted $C_{1-3}$ alkyl group, or $R^{7b}$ represents, together with one substituent $R^4$ on ring A, an optionally substituted $C_{2-3}$ alkylene group;

m number of $R^4$ are the same or different and each are an optionally substituted $C_{1-3}$ alkyl group, an optionally substituted $C_{2-3}$ alkylene group formed together by two adjacent $R^4$, or an optionally substituted $C_{2-3}$ alkylene group formed together by one $R^4$ and $R^{7b}$; and m is an integer of 0 to 2.

<12>

The compound according to <11> or a salt thereof, wherein $X^1$ is a group represented by the general formula $N(R^{7b})C(=O)$ wherein the nitrogen atom is bonded to ring A, and $R^{7b}$ represents an optionally substituted $C_{1-3}$ alkyl group, or $R^{7b}$ represents, together with one substituent $R^4$ on ring A, an optionally substituted $C_{2-3}$ alkylene group;

m number of $R^4$ are the same or different and each are an optionally substituted $C_{1-3}$ alkyl group, or an optionally substituted $C_{2-3}$ alkylene group formed together by one $R^4$ and $R^{7b}$; and m is an integer of 0 to 2.

<13>

The compound according to any one of <1> to <4> or a salt thereof, wherein $X^1$ is an optionally substituted divalent cyclic hydrocarbon group resulting from the removal of one hydrogen atom from each of two adjacent atoms or an optionally substituted divalent heterocyclic group resulting from the removal of one hydrogen atom from each of two adjacent atoms.

<14>

The compound according to any one of <1> to <4> or a salt thereof, wherein $R^3$ is an optionally substituted $C_{1-6}$ alkyl group or an optionally substituted heterocyclic group;

$X^1$ is an optionally substituted divalent cyclic hydrocarbon group resulting from the removal of one hydrogen atom from each of two adjacent atoms or an optionally substituted divalent heterocyclic group resulting from the removal of one hydrogen atom from each of two adjacent atoms;

m number of $R^4$ are the same or different and each are a halogen atom; and m is an integer of 0 to 2.

<15>

The compound according to <14> or a salt thereof, wherein $R^3$ is an optionally substituted heterocyclic group; and $X^1$ is an optionally substituted divalent heterocyclic group resulting from the removal of one hydrogen atom from each of two adjacent atoms.

<16>

A pharmaceutical composition comprising a compound according to any one of <1> to <15> or a salt thereof.

<17>

An agent for treatment of an immune disease, comprising a compound according to any one of <1> to <15> or a salt thereof.

Advantageous Effects of Invention

The compound of the present invention has an excellent CXCL10 inhibitory activity and is useful as an agent for treatment such as prophylaxis and/or therapy of a disease involving the overproduction of CXCL10.

DESCRIPTION OF EMBODIMENTS

The present invention will be described below in detail.

In the present invention, % means % by mass, unless otherwise specified.

In the present invention, each term has the following meaning, unless otherwise specified.

The halogen atom means a fluorine atom, a chlorine atom, a bromine atom or an iodine atom.

The $C_{1-6}$ alkyl group means a linear or branched $C_{1-6}$ alkyl group such as a methyl group, an ethyl group, a propyl group, an isopropyl group, a butyl group, a sec-butyl group, an isobutyl group, a tert-butyl group, a pentyl group, an isopentyl group and a hexyl group.

The $C_{1-3}$ alkyl group means a methyl group, an ethyl group, a propyl group or an isopropyl group.

The $C_{2-6}$ alkenyl group means a linear or branched $C_{2-6}$ alkenyl group such as a vinyl group, an allyl group, a propenyl group, an isopropenyl group, a butenyl group, an isobutenyl group, a 1,3-butadienyl group, a pentenyl group and a hexenyl group.

The $C_{2-6}$ alkynyl group means a linear or branched $C_{2-6}$ alkynyl group such as an ethynyl group, a propynyl group, a butynyl group, a pentynyl group and a hexynyl group.

The $C_{3-8}$ cycloalkyl group means a $C_{3-8}$ cycloalkyl group such as a cyclopropyl group, a cyclobutyl group, a cyclopentyl group and a cyclohexyl group.

The $C_{4-8}$ cycloalkenyl group means a $C_{4-8}$ cycloalkenyl group such as a cyclobutenyl group, a cyclopentenyl group, a cyclohexenyl group and a cyclohexadienyl group.

The aryl group means a phenyl group or a naphthyl group.

The ar-$C_{1-6}$ alkyl group means an ar-$C_{1-6}$ alkyl group such as a benzyl group, a diphenylmethyl group, a trityl group, a phenethyl group and a naphthylmethyl group.

The $C_{2-5}$ alkylene group means a linear or branched $C_{2-5}$ alkylene group such as an ethylidene group, an ethylene group, a trimethylene group, a propylene group, a tetramethylene group and a pentamethylene group.

The $C_{2-4}$ alkylene group means a linear or branched $C_{2-4}$ alkylene group such as an ethylidene group, an ethylene group, a trimethylene group, a propylene group and a tetramethylene group.

The $C_{2-3}$ alkylene group means an ethylidene group, an ethylene group, a trimethylene group or a propylene group.

The $C_{1-3}$ alkylene group means a methylene group, an ethylidene group, an ethylene group, a trimethylene group or a propylene group.

The $C_{1-6}$ alkoxy group means a linear or branched $C_{1-6}$ alkyloxy group such as a methoxy group, an ethoxy group, a propoxy group, an isopropoxy group, a butoxy group, an isobutoxy group, a sec-butoxy group, a tert-butoxy group, a pentyloxy group and a hexyloxy group.

The aryloxy group means a phenoxy group or a naphthyloxy group.

The $C_{1-6}$ alkoxy-$C_{1-6}$ alkyl group means a $C_{1-6}$ alkyloxy-$C_{1-6}$ alkyl group such as a methoxymethyl group and a 1-ethoxyethyl group.

The ar-$C_{1-6}$ alkoxy-$C_{1-6}$ alkyl group means an ar-$C_{1-6}$ alkyloxy-$C_{1-6}$ alkyl group such as a benzyloxymethyl group and a phenethyloxymethyl group.

The $C_{2-6}$ alkanoyl group means a linear or branched $C_{2-6}$ alkanoyl group such as an acetyl group, a propionyl group, a valeryl group, an isovaleryl group and a pivaloyl group.

The aroyl group means a benzoyl group or a naphthoyl group.

The heterocyclic carbonyl group means a furoyl group, a thenoyl group, a pyrrolidinylcarbonyl group, a piperidinylcarbonyl group, a piperazinylcarbonyl group, a morpholinylcarbonyl group or a pyridinylcarbonyl group.

The acyl group means a formyl group, a $C_{2-6}$ alkanoyl group, an aroyl group or a heterocyclic carbonyl group.

The $C_{1-6}$ alkoxycarbonyl group means a linear or branched $C_{1-6}$ alkyloxycarbonyl group such as a methoxycarbonyl group, an ethoxycarbonyl group, a propoxycarbonyl group, an isopropoxycarbonyl group, a tert-butoxycarbonyl group and a 1,1-dimethylpropoxycarbonyl group.

The aryloxycarbonyl group means a phenyloxycarbonyl group or a naphthyloxycarbonyl group.

The ar-$C_{1-6}$ alkoxycarbonyl group means an ar-$C_{1-6}$ alkyloxycarbonyl group such as a benzyloxycarbonyl group and a phenethyloxycarbonyl group.

The $C_{1-6}$ alkylamino group means a linear or branched $C_{1-6}$ alkylamino group such as a methylamino group, an ethylamino group, a propylamino group, an isopropylamino group, a butylamino group, a sec-butylamino group, a tert-butylamino group, a pentylamino group and a hexylamino group.

The $C_{1-3}$ alkylamino group means a linear or branched $C_{1-3}$ alkylamino group such as a methylamino group, an ethylamino group, a propylamino group and an isopropylamino group.

The di($C_{1-6}$ alkyl)amino group means a linear or branched di($C_{1-6}$ alkyl)amino group such as a dimethylamino group, a diethylamino group, a dipropylamino group, a diisopropylamino group, a dibutylamino group, a di(tert-butyl)amino group, a dipentylamino group, a dihexylamino group, an (ethyl)(methyl)amino group and a (methyl)(propyl)amino group.

The arylamino group means a phenylamino group or a naphthylamino group.

The $C_{1-6}$ alkylthio group means a $C_{1-6}$ alkylthio group such as a methylthio group, an ethylthio group and a propylthio group.

The arylthio group means a phenylthio group or a naphthylthio group.

The $C_{1-6}$ alkylsulfonyl group means a $C_{1-6}$ alkylsulfonyl group such as a methylsulfonyl group, an ethylsulfonyl group and a propylsulfonyl group.

The $C_{1-3}$ alkylsulfonyl group means a $C_{1-3}$ alkylsulfonyl group such as a methylsulfonyl group, an ethylsulfonyl group and a propylsulfonyl group.

The arylsulfonyl group means a benzenesulfonyl group, a p-toluenesulfonyl or a naphthalenesulfonyl group.

The $C_{1-6}$ alkylsulfonyloxy group means a $C_{1-6}$ alkylsulfonyloxy group such as a methylsulfonyloxy group, an ethylsulfonyloxy group and a propylsulfonyloxy group.

The arylsulfonyloxy group means a benzenesulfonyloxy group, a p-toluenesulfonyloxy group or a naphthalenesulfonyloxy group.

The silyl group means a trimethylsilyl group, a triethylsilyl group or a tributylsilyl group.

The cyclic amino group means, for example, a cyclic amino group which contains one or more nitrogen atoms as heteroatoms constituting the ring and may further contain one or more atoms selected from an oxygen atom and a sulfur atom, such as aziridinyl, azetidinyl, pyrrolidinyl, piperidinyl, homopiperidinyl, pyrrolyl, dihydropyrrolyl, pyrazolyl, pyrazolinyl, pyrazolidinyl, imidazolyl, imidazolinyl, imidazolidinyl, thiazolinyl, thiazolidinyl, dihydrothiadiazolyl, piperazinyl, homopiperazinyl, morpholinyl, homomorpholinyl, thiomorpholinyl, tetrahydroquinolinyl, tetrahydroisoquinolinyl, decahydroisoquinolinyl, benzomorpholinyl, dihydropyridoxazinyl and quinuclidinyl.

The cyclic hydrocarbon group means a $C_{3-8}$ cycloalkyl group, a $C_{4-8}$ cycloalkenyl group or an aryl group.

The monocyclic nitrogen-containing heterocyclic group means a monocyclic nitrogen-containing heterocyclic group which contains only a nitrogen atom as a heteroatom constituting the ring and is optionally substituted by an oxo group, such as an azetidinyl group, a pyrrolidinyl group, an oxopyrrolidinyl group, a pyrrolinyl group, a pyrrolyl group, a piperidyl group, an oxopiperidyl group, a tetrahydropyridyl group, a dihydropyridyl group, a pyridyl group, a homopiperidinyl group, an octahydroazocinyl group, an imidazolidinyl group, an oxoimidazolidinyl group, an imidazolinyl group, a dihydrooxoimidazolyl group, an imidazolyl group, a pyrazolidinyl group, a pyrazolinyl group, a pyrazolyl group, a piperazinyl group, a homopiperazinyl group, a pyrazinyl group, a pyridazinyl group, a pyrimidinyl group, a triazolidinyl group, a dioxotriazolidinyl group, a triazolyl group and a tetrazolyl group.

The monocyclic oxygen-containing heterocyclic group means an oxetanyl group, a tetrahydrofuranyl group, an oxotetrahydrofuranyl group, a furanyl group, a tetrahydropyranyl group, an oxotetrahydropyranyl group, a dihydropyranyl group or a pyranyl group.

The monocyclic sulfur-containing heterocyclic group means a tetrahydrothienyl group, an oxotetrahydrothienyl group or a thienyl group.

The monocyclic nitrogen- and oxygen-containing heterocyclic group means a monocyclic nitrogen- and oxygen-containing heterocyclic group which contains only a nitrogen atom and an oxygen atom as heteroatoms constituting the ring and is optionally substituted by an oxo group, such as an oxazolyl group, an isoxazolyl group, an oxoisoxazolyl group, an oxadiazolyl group and a morpholinyl group.

The monocyclic nitrogen- and sulfur-containing heterocyclic group means a monocyclic nitrogen- and sulfur-containing heterocyclic group which contains only a nitrogen atom and a sulfur atom as heteroatoms constituting the ring and is optionally substituted by an oxo group, such as a thiazolyl group, an isothiazolyl group, a thiadiazolyl group, a thiomorpholinyl group, a 1-oxidothiomorpholinyl group and a 1,1-dioxidothiomorpholinyl group.

The monocyclic heterocyclic group means a monocyclic nitrogen-containing heterocyclic group, a monocyclic oxygen-containing heterocyclic group, a monocyclic sulfur-containing heterocyclic group, a monocyclic nitrogen- and oxygen-containing heterocyclic group or a monocyclic nitrogen- and sulfur-containing heterocyclic group.

The bicyclic nitrogen-containing heterocyclic group means a bicyclic nitrogen-containing heterocyclic group which contains only a nitrogen atom as a heteroatom constituting the rings and is optionally substituted by an oxo group, such as an indolinyl group, an oxoindolinyl group, an indolyl group, an isoindolinyl group, an oxoisoindolinyl group, an isoindolyl group, a pyrrolopyridinyl group, an indazolyl group, a benzimidazolyl group, a benzotriazolyl group, a tetrahydroquinolinyl group, an oxotetrahydroquinolinyl group, a dihydroquinolinyl group, an oxodihydroquinolinyl group, a quinolinyl group, a dihydroisoquinolinyl group, an octahydroisoquinolinyl group, a oxooctahydroisoquinolinyl group, a tetrahydroisoquinolinyl group, a decahydroisoquinolinyl group, an isoquinolinyl group, a dihydroquinazolinyl group, a cinnolinyl group, a phthalazinyl group, a quinazolinyl group, a tetrahydroquinoxalinyl group, an oxotetrahydroquinoxalinyl group, a hydroquinoxalinyl group, a quinoxalinyl group, a naphthyridinyl group, a purinyl group, a pteridinyl group and a quinuclidinyl group.

The bicyclic oxygen-containing heterocyclic group means a bicyclic oxygen-containing heterocyclic group which contains only an oxygen atom as a heteroatom constituting the rings and is optionally substituted by an oxo group, such as a 2,3-dihydrobenzofuranyl group, an oxo-2,3-dihydrobenzofuranyl group, a benzofuranyl group, an isobenzofuranyl group, a chromanyl group, an oxochromanyl group, a chromenyl group, an isochromanyl group, an oxoisochromanyl group, a 1,3-benzodioxolyl group, a 1,3-benzodioxanyl and a 1,4-benzodioxanyl group.

The bicyclic sulfur-containing heterocyclic group means a bicyclic sulfur-containing heterocyclic group which contains only a sulfur atom as a heteroatom constituting the rings and is optionally substituted by an oxo group, such as a 2,3-dihydrobenzothienyl group, an oxo-2,3-dihydrobenzothienyl group and a benzothienyl group.

The bicyclic nitrogen- and oxygen-containing heterocyclic group means a bicyclic nitrogen- and oxygen-containing heterocyclic group which contains only a nitrogen atom and an oxygen atom as heteroatoms constituting the rings and is optionally substituted by an oxo group, such as a dihydrobenzoxazolyl group, an oxodihydrobenzoxazolyl group, a benzoxazolyl group, a benzisoxazolyl group, a benzoxadiazolyl group, a benzomorpholinyl group, an oxobenzomorpholinyl group, a dihydropyranopyridyl group, an oxodihydropyranopyridyl group, a dihydrodioxinopyridyl group, an oxodihydrodioxinopyridyl group and a dihydropyridoxazinyl group.

The bicyclic nitrogen- and sulfur-containing heterocyclic group means a bicyclic nitrogen- and sulfur-containing heterocyclic group which contains a nitrogen atom and a sulfur atom as heteroatoms constituting the rings and is optionally substituted by an oxo group, such as a dihydrobenzothiazolyl group, an oxodihydrobenzothiazolyl group, a benzothiazolyl group, a benzisothiazolyl group and a benzothiadiazolyl group.

The bicyclic heterocyclic group means a bicyclic nitrogen-containing heterocyclic group, a bicyclic oxygen-containing heterocyclic group, a bicyclic sulfur-containing heterocyclic group, a bicyclic nitrogen- and oxygen-containing heterocyclic group or a bicyclic nitrogen- and sulfur-containing heterocyclic group.

The heterocyclic group means a monocyclic heterocyclic group or a bicyclic heterocyclic group.

The $C_{3-8}$ cycloalkane means cyclopropane, cyclobutane, cyclopentane, cyclohexane, cycloheptane or cyclooctane.

The $C_{4-8}$ cycloalkene means $C_{4-8}$ cycloalkene such as cyclobutene, cyclopentene, cyclopentadiene, cyclohexene, cyclohexadiene and cycloheptene.

The cyclic hydrocarbon means $C_{3-8}$ cycloalkane, $C_{4-8}$ cycloalkene, benzene or naphthalene.

The nitrogen-containing heterocyclic ring means a nitrogen-containing heterocyclic ring which contains only a nitrogen atom as a heteroatom constituting the ring and is optionally substituted by an oxo group, such as azetidine, pyrrolidine, oxopyrrolidine, pyrroline, pyrrole, piperidine, oxopiperidine, tetrahydropyridine, dihydropyridine, oxodihydropyridine, pyridine, homopiperidine, octahydroazocine, imidazolidine, oxoimidazolidine, imidazoline, dihydrooxoimidazole, imidazole, pyrazolidine, dioxopyrazolidine, pyrazoline, oxopyrazoline, pyrazole, piperazine, homopiperazine, pyrazine, pyridazine, pyrimidine, triazolidine, dioxotriazolidine, triazole, tetrazole, 1H-benzimidazole and quinoxaline.

The oxygen-containing heterocyclic ring means oxetane, tetrahydrofuran, oxotetrahydrofuran, furan, tetrahydropyran, oxotetrahydropyran, dihydropyran or pyran.

The sulfur-containing heterocyclic ring means tetrahydrothiophene, oxotetrahydrothiophene or thiophene.

The nitrogen- and oxygen-containing heterocyclic ring means a monocyclic nitrogen- and oxygen-containing heterocyclic ring which contains only a nitrogen atom and an oxygen atom as heteroatoms constituting the ring and is optionally substituted by an oxo group, such as oxazole, isoxazole, oxoisoxazole, oxadiazole and morpholine.

The nitrogen- and sulfur-containing heterocyclic ring means a monocyclic nitrogen- and sulfur-containing heterocyclic ring which contains only a nitrogen atom and a sulfur atom as heteroatoms constituting the ring and is optionally substituted by an oxo group, such as thiazole, isothiazole, thiadiazole, thiomorpholine, 1-oxidothiomorpholine and 1,1-dioxidothiomorpholine.

The heterocyclic ring means a nitrogen-containing heterocyclic ring, an oxygen-containing heterocyclic ring, a sulfur-containing heterocyclic ring, a nitrogen- and oxygen-containing heterocyclic ring or a nitrogen- and sulfur-containing heterocyclic ring.

The divalent cyclic hydrocarbon group resulting from the removal of one hydrogen atom from each of two adjacent atoms means a group which is formed by the removal of two hydrogen atoms bonded to two adjacent atoms from cyclic hydrocarbon, such as cyclopropane-1,2-diyl, cyclobutane-1,2-diyl, cyclobutene-1,2-diyl, cyclopentane-1,2-diyl, cyclopentene-1,2-diyl, cyclopentadiene-1,2-diyl, cyclohexane-1,2-diyl, cyclohexene-1,2-diyl, cyclohexadiene-1,2-diyl, cycloheptane-1,2-diyl, cycloheptene-1,2-diyl, cyclooctane-1,2-diyl, benzene-1,2-diyl, naphthalene-1,2-diyl and naphthalene-2,3-diyl.

The divalent heterocyclic group resulting from the removal of one hydrogen atom from each of two adjacent atoms means a group which is formed by the removal of two hydrogen atoms bonded to two adjacent atoms from a heterocyclic ring and optionally substituted by an oxo group, such as azetidine-1,2-diyl, pyrrolidine-1,2-diyl, oxopyrrolidine-1,2-diyl, oxopyrrolidine-3,4-diyl, pyrroline-3,4-diyl, pyrrole-3,4-diyl, piperidine-2,3-diyl, piperidine-3,4-diyl, oxopiperidine-2,3-diyl, tetrahydropyridine-1,2-diyl, tetrahydropyridine-2,3-diyl, tetrahydropyridine-3,4-diyl, dihydropyridine-2,3-diyl, dihydropyridine-3,4-diyl, dihydropyridine-1,2-diyl, oxodihydropyridine-1,2-diyl, pyridine-2,3-diyl, pyridine-3,4-diyl, homopiperidine-2,3-diyl, homopiperidine-3,4-diyl, octahydroazocine-2,3-diyl, imidazolidine-1,5-diyl, oxoimidazolidine-1,5-diyl, 1,2-dihydroimidazole-3,4-diyl, 4,5-dihydroimidazole-1,2-diyl, dihydroxoimidazole-1,5-diyl, 2H-imidazole-4,5-diyl, imidazole-1,2-diyl, imidazole-1,5-diyl, imidazole-4,5-diyl, pyrazolidine-1,2-diyl, dioxopyrazolidine-1,2-diyl, pyrazoline-1,2-diyl, oxopyrazoline-1,2-diyl, pyrazoline-1,5-diyl, 1H-pyrazole-3,4-diyl, 1H-pyrazole-4,5-diyl, 1H-pyrazole-1,5-diyl, piperazine-1,2-diyl, piperazine-2,3-diyl, homopiperazine-1,2-diyl, homopiperazine-2,3-diyl, pyrazine-2,3-diyl, pyridazine-3,4-diyl, pyrimidine-4,5-diyl, 1,2,4-triazolidine-1,2-diyl, dioxotriazolidine-1,2-diyl, 1,2,3-triazole-1,5-diyl, 1,2,4-triazole-1,5-diyl, 1,2,4-triazole-3,4-diyl, tetrazole-1,5-diyl, 1H-benzimidazole-1,2-diyl, quinoxaline-2,3-diyl, oxetane-2,3-diyl, tetrahydrofuran-2,3-diyl, oxotetrahydrofuran-2,3-diyl, furan-2,3-diyl, tetrahydropyran-2,3-diyl, oxotetrahydropyran-2,3-diyl, dihydropyran-2,3-diyl, pyran-2,3-diyl, tetrahydrothiophene-2,3-diyl, oxotetrahydrothiophene-2,3-diyl, thiophene-3,4-diyl, oxazole-4,5-diyl, isoxazole-3,4-diyl, dihydrooxoisoxazole- 3,4-diyl, 1,2,3-oxadiazole-4,5-diyl, morpholine-2,3-diyl, morpholine-3,4-diyl, thiazole-4,5-diyl, isothiazole-4,5-diyl, 1,2,3-thiadiazole-4,5-diyl, thiomorpholine-2,3-diyl, 1-oxidothiomorpholine-2,3-diyl and 1,1-dioxidothiomorpholine-2,3-diyl.

The leaving group means a halogen atom, a $C_{1-6}$ alkylsulfonyloxy group or an arylsulfonyloxy group. The $C_{1-6}$ alkylsulfonyloxy group and the arylsulfonyloxy group are each optionally substituted by one or more groups selected from substituent group A.

Substituent group A: a halogen atom, a carbamoyl group optionally substituted by one or more groups selected from substituent group B, a sulfamoyl group optionally substituted by one or more groups selected from substituent group B, an acyl group optionally substituted by one or more groups selected from substituent group B, a $C_{1-6}$ alkyl group optionally substituted by one or more groups selected from substituent group B, a $C_{2-6}$ alkenyl group optionally substituted by one or more groups selected from substituent group B, a $C_{3-8}$ cycloalkyl group optionally substituted by one or more groups selected from substituent group B, a $C_{4-8}$ cycloalkenyl group optionally substituted by one or more groups selected from substituent group B, a $C_{1-6}$ alkoxy group optionally substituted by one or more groups selected from substituent group B, a $C_{1-6}$ alkylsulfonyl group optionally substituted by one or more groups selected from substituent group B, an arylsulfonyl group optionally substituted by one or more groups selected from substituent group B, a $C_{1-6}$ alkylamino group optionally substituted by one or more groups selected from substituent group B, a di($C_{1-6}$ alkyl)amino group optionally substituted by one or more groups selected from substituent group B, an aryl group optionally substituted by one or more groups selected from substituent group B, a heterocyclic group optionally substituted by one or more groups selected from substituent group B, an arylamino group optionally substituted by one or more groups selected from substituent group B, a cyano group, an optionally protected amino group, an optionally protected hydroxyl group, an optionally protected carboxyl group and an oxo group.

Substituent group B: a halogen atom, an acyl group, a $C_{1-6}$ alkyl group optionally substituted by one or more groups selected from substituent group C, a $C_{3-8}$ cycloalkyl group optionally substituted by one or more groups selected from substituent group C, a $C_{1-6}$ alkoxy group optionally substituted by one or more groups selected from substituent group C, a $C_{1-6}$ alkylamino group, a di($C_{1-6}$ alkyl)amino group, an aryl group optionally substituted by one or more groups selected from substituent group C, a heterocyclic group optionally substituted by one or more groups selected from substituent group C, a cyano group, an optionally protected amino group, an optionally protected hydroxyl group, an optionally protected carboxyl group and an oxo group.

Substituent group C: a halogen atom, an optionally protected amino group, an optionally protected hydroxyl group and an optionally protected carboxyl group.

The hydroxyl-protective group includes every group that can be used as a usual protective group for a hydroxyl group. Examples thereof include a group described in Greene's Protective Groups in Organic Synthesis, 5th ed., p. 17-471, 2014, John Wiley & Sons, INC. Specific examples thereof include a $C_{1-6}$ alkyl group, an ar-$C_{1-6}$ alkyl group, a $C_{1-6}$ alkoxy-$C_{1-6}$ alkyl group, an acyl group, a $C_{1-6}$ alkoxycarbonyl group, an ar-$C_{1-6}$ alkoxycarbonyl group, a $C_{1-6}$ alkylsulfonyl group, an arylsulfonyl group, a silyl group, a tetrahydrofuranyl group and a tetrahydropyranyl group. These groups are each optionally substituted by one or more groups selected from substituent group A.

The carboxyl-protective group includes every group that can be used as a usual protective group for an amino group. Examples thereof include a group described in Greene's Protective Groups in Organic Synthesis, 5th ed., p. 686-836, 2014, John Wiley & Sons, INC. Specific examples thereof include a $C_{1-6}$ alkyl group, an ar-$C_{1-6}$ alkyl group, a $C_{1-6}$ alkoxy-$C_{1-6}$ alkyl group, an ar-$C_{1-6}$ alkoxy-$C_{1-6}$ alkyl group and a silyl group. These groups are each optionally substituted by one or more groups selected from substituent group A.

The amino-protective group includes every group that can be used as a usual protective group for an amino group. Examples thereof include a group described in Greene's Protective Groups in Organic Synthesis, 5th ed., p. 895-1193, 2014, John Wiley & Sons, INC. Specific examples thereof include an ar-$C_{1-6}$ alkyl group, a $C_{1-6}$ alkoxy-$C_{1-6}$ alkyl group, an acyl group, a $C_{1-6}$ alkoxycarbonyl group, an ar-$C_{1-6}$ alkoxycarbonyl group, an aryloxycarbonyl group, a $C_{1-6}$ alkylsulfonyl group, an arylsulfonyl group and a silyl group. These groups are each optionally substituted by one or more groups selected from substituent group A.

The aliphatic hydrocarbons mean pentane, hexane, heptane, cyclohexane, methylcyclohexane or ethylcyclohexane.

The halogenated hydrocarbons mean dichloromethane, chloroform or dichloroethane.

The ethers mean diethyl ether, diisopropyl ether, tetrahydrofuran, 2-methyltetrahydrofuran, 1,4-dioxane, anisole, ethylene glycol dimethyl ether, diethylene glycol dimethyl ether or diethylene glycol diethyl ether.

The alcohols mean methanol, ethanol, propanol, 2-propanol, butanol, 2-methyl-2-propanol, ethylene glycol, propylene glycol or diethylene glycol.

The ketones mean acetone, 2-butanone or 4-methyl-2-pentanone.

The esters mean methyl acetate, ethyl acetate, propyl acetate, isopropyl acetate or butyl acetate.

The amides mean N,N-dimethylformamide, N,N-dimethylacetamide or N-methylpyrrolidone.

The nitriles mean acetonitrile or propionitrile.

The sulfoxides mean dimethyl sulfoxide or sulfolane.

The aromatic hydrocarbons mean benzene, toluene or xylene.

The inorganic base means sodium hydroxide, potassium hydroxide, sodium bicarbonate, sodium carbonate, sodium hydride, potassium carbonate, tripotassium phosphate, potassium acetate, cesium fluoride or cesium carbonate.

The organic base means sodium methoxide, sodium ethoxide, sodium tert-butoxide, potassium tert-butoxide, triethylamine, N,N-diisopropylethylamine, 1,8-diazabicyclo (5.4.0)undec-7-ene (DBU), pyridine, N,N-dimethyl-4-aminopyridine or 4-methylmorpholine.

The $C_{1-6}$ alkyl group represented by $R^1$; the $C_{1-6}$ alkyl group, the $C_{2-6}$ alkenyl group, the $C_{3-8}$ cycloalkyl group, the $C_{4-8}$ cycloalkenyl group, the aryl group, the $C_{1-6}$ alkoxy group, the $C_{1-6}$ alkylamino group, the di($C_{1-6}$ alkylamino group and the heterocyclic group represented by $R^3$; the $C_{1-6}$ alkyl group, the $C_{1-3}$ alkyl group, the $C_{2-6}$ alkenyl group, the $C_{2-6}$ alkynyl group, the $C_{3-8}$ cycloalkyl group, the $C_{4-8}$ cycloalkenyl group, the aryl group, the $C_{1-6}$ alkoxy group, the aryloxy group, the $C_{1-6}$ alkylamino group, the $C_{1-3}$ alkylamino group, the di($C_{1-6}$ alkyl)amino group, the arylamino group, the carbamoyl group, the sulfamoyl group, the $C_{1-6}$ alkylthio group, the arylthio group, the $C_{1-6}$ alkylsulfonyl group, the $C_{1-3}$ alkylsulfonyl group, the arylsulfonyl group and the heterocyclic group represented by $R^4$; the $C_{2-3}$ alkylene group and the $C_{2-5}$ alkylene group formed together by two adjacent $R^4$; the $C_{1-6}$ alkyl group represented by $R^3$; the $C_{1-6}$ alkyl group represented by $R^6$; the $C_{1-3}$ alkyl group represented by $R^{6a}$; the $C_{1-3}$ alkyl group represented by $R^{6b}$; the $C_{1-6}$ alkyl group represented by $R^7$; the $C_{1-3}$ alkylene group represented by $Y^1$; the $C_{1-3}$ alkylene group represented by $Y^2$; the $C_{1-3}$ alkylene group represented by $Y^3$; the $C_{1-3}$ alkyl group represented by $R^{7a}$; the $C_{1-3}$ alkyl group represented by $R^{7b}$; the $C_{2-4}$ alkylene group formed together by $R^4$ and $R^7$; the $C_{2-3}$ alkylene group formed together by $R^4$ and $R^{7a}$; the $C_{2-3}$ alkylene group formed together by $R^4$ and $R^{7b}$; the $C_{1-6}$ alkyl group and the aryl group represented by $R^8$; the divalent cyclic hydrocarbon group resulting from the removal of one hydrogen atom from each of two adjacent atoms and the divalent heterocyclic group resulting from the removal of one hydrogen atom from each of two adjacent atoms, represented by $X^1$; the divalent cyclic hydrocarbon group resulting from the removal of one hydrogen atom from each of two adjacent atoms and the divalent heterocyclic group resulting from the removal of one hydrogen atom from each of two adjacent atoms, represented by $X^{1A}$; the $C_{1-6}$ alkyl group represented by $R^a$; the $C_{1-6}$ alkyl group represented by $R^b$; the $C_{1-3}$ alkylene group formed together by $R^a$ and $R^b$; the $C_{1-6}$ alkyl group represented by $R^c$; the $C_{1-6}$ alkyl group represented by $R^d$; and the $C_{1-3}$ alkylene group formed together by $R^c$ and $R^d$ are each optionally substituted by one or more groups selected from substituent group A.

The $C_{1-6}$ alkyl group represented by $R^2$ is optionally substituted by one or more groups selected from substituent group B.

In the present invention, examples of preferred compounds include the following compounds or salts thereof.

$R^1$ is an optionally substituted $C_{1-6}$ alkyl group.

A compound in which $R^1$ is a $C_{1-3}$ alkyl group is preferred. A compound in which $R^1$ is an ethyl group is more preferred.

$R^2$ is a hydrogen atom, a halogen atom or an optionally substituted $C_{1-6}$ alkyl group.

A compound in which $R^2$ is a hydrogen atom or an optionally substituted $C_{1-6}$ alkyl group is preferred. A compound in which $R^2$ is a hydrogen atom is more preferred.

$R^3$ is a halogen atom, an optionally substituted $C_{1-6}$ alkyl group, an optionally substituted $C_{2-6}$ alkenyl group, an optionally substituted $C_{3-8}$ cycloalkyl group, an optionally substituted $C_{4-8}$ cycloalkenyl group, an optionally substituted aryl group, an optionally substituted $C_{1-6}$ alkoxy group, an optionally substituted $C_{1-6}$ alkylamino group, an optionally substituted di($C_{1-6}$ alkyl)amino group or an optionally substituted heterocyclic group.

A compound in which $R^3$ is a halogen atom, an optionally substituted $C_{1-6}$ alkyl group, an optionally substituted $C_{2-6}$ alkenyl group, an optionally substituted $C_{3-8}$ cycloalkyl group, an optionally substituted $C_{4-8}$ cycloalkenyl group, an optionally substituted aryl group, an optionally substituted di($C_{1-6}$ alkyl)amino group or an optionally substituted heterocyclic group is preferred.

A compound in which $R^3$ is an optionally substituted $C_{1-6}$ alkyl group, an optionally substituted $C_{3-8}$ cycloalkyl group, an optionally substituted aryl group or an optionally substituted heterocyclic group is more preferred.

A compound in which $R^3$ is an optionally substituted $C_{1-6}$ alkyl group, an optionally substituted $C_{3-8}$ cycloalkyl group or an optionally substituted heterocyclic group is further preferred.

A compound in which $R^3$ is an optionally substituted $C_{1-6}$ alkyl group or an optionally substituted heterocyclic group is still further preferred.

A compound in which $R^3$ is an optionally substituted heterocyclic group is particularly preferred.

$Z^1$, $Z^2$ and $Z^3$ are the same or different and each are a nitrogen atom or a group represented by the general formula $CR^5$ wherein $R^5$ is as defined above.

A compound in which each of $Z^1$, $Z^2$ and $Z^3$ is a group represented by the general formula $CR^5$ wherein $R^5$ is as defined above is preferred. A compound in which each of $Z^1$, $Z^2$ and $Z^3$ is CH is more preferred.

$X^1$ is (1) a group represented by the general formula $C(=O)N(R^6)$ wherein $R^6$ is as defined above, (2) a group represented by the general formula $N(R^7)C(=O)$ wherein $R^7$ is as defined above, (3) an optionally substituted divalent cyclic hydrocarbon group resulting from the removal of one hydrogen atom from each of two adjacent atoms or (4) an optionally substituted divalent heterocyclic group resulting from the removal of one hydrogen atom from each of two adjacent atoms.

A compound in which $X^1$ is a group represented by the general formula $C(=O)N(R^6)$ wherein $R^6$ is as defined above is preferred. A compound in which $X^1$ is a group represented by the general formula $C(=O)N(R^{6a})$ wherein $R^{6a}$ is as defined above is more preferred. A compound in which $X^1$ is a group represented by the general formula $C(=O)N(R^{6b})$ wherein $R^{6b}$ is as defined above is further preferred.

In an alternative embodiment, a compound in which $X^1$ is a group represented by the general formula $N(R^7)C(=O)$ wherein $R^7$ is as defined above is preferred. A compound in which $X^1$ is a group represented by the general formula $N(R^{7a})C(=O)$ wherein $R^{7a}$ is as defined above is more preferred. A compound in which $X^1$ is a group represented by the general formula $N(R^{7b})C(=O)$ wherein $R^{7b}$ is as defined above is further preferred.

In a further alternative embodiment, a compound in which $X^1$ is an optionally substituted divalent cyclic hydrocarbon group resulting from the removal of one hydrogen atom from each of two adjacent atoms or an optionally substituted divalent heterocyclic group resulting from the removal of one hydrogen atom from each of two adjacent atoms is preferred.

A compound in which $X^1$ is an optionally substituted divalent heterocyclic group resulting from the removal of one hydrogen atom from each of two adjacent atoms is more preferred.

Ring A is a cyclic hydrocarbon group or a heterocyclic group.

A compound in which ring A is a cyclic hydrocarbon group is preferred.

A compound in which ring A is a phenyl group is more preferred.

"m" number of $R^4$ are the same or different and each are a halogen atom, a cyano group, a nitro group, an amino-protective group, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{4-8}$ cycloalkenyl group, an optionally substituted aryl group, an optionally substituted $C_{1-6}$ alkoxy group, an optionally substituted aryloxy group, an optionally substituted $C_{1-6}$ alkylamino group, an optionally substituted di($C_{1-6}$ alkyl)amino group, an optionally substituted arylamino group, an optionally substituted carbamoyl group, an optionally substituted sulfamoyl group, an optionally substituted $C_{1-6}$ alkylthio group, an optionally substituted arylthio group, an optionally substituted $C_{1-6}$ alkylsulfonyl group, an optionally substituted arylsulfonyl group, an optionally substituted heterocyclic group, an optionally protected amino group, an optionally protected hydroxyl group or an optionally protected carboxyl group. In this context, two adjacent $R^4$ may together form an optionally substituted $C_{2-5}$ alkylene group, and one $R^4$ may form, together with $R^7$, an optionally substituted $C_{2-4}$ alkylene group, a group represented by the general formula $O—Y^1$ wherein $Y^1$ is as defined above, a group represented by the general formula $S(O)_n—Y^2$ wherein $Y^2$ and n are as defined above or a group represented by the general formula $N(R^8)—Y^3$ wherein $Y^3$ and $R^8$ are as defined above.

A compound in which m number of $R^4$ are the same or different and each are a halogen atom, a cyano group, an optionally substituted $C_{1-6}$ alkyl group, an optionally substituted $C_{2-6}$ alkenyl group, an optionally substituted $C_{3-8}$ cycloalkyl group, an optionally substituted $C_{4-8}$ cycloalkenyl group, an optionally substituted aryl group, an optionally substituted $C_{1-6}$ alkoxy group, an optionally substituted $C_{1-6}$ alkylamino group, an optionally substituted di($C_{1-6}$ alkyl)amino group, an optionally substituted arylamino group, an optionally substituted carbamoyl group, an optionally substituted sulfamoyl group, an optionally substituted $C_{1-6}$ alkylsulfonyl group, an optionally substituted heterocyclic group, an optionally protected amino group, an optionally protected hydroxyl group or an optionally protected carboxyl group is preferred.

A compound in which m number of $R^4$ are the same or different and each are a halogen atom, an optionally substituted $C_{1-3}$ alkyl group, an optionally substituted $C_{1-3}$ alkylamino group, an optionally substituted $C_{1-3}$ alkylsulfonyl group or an optionally protected amino group is more preferred.

A compound in which m number of $R^4$ are the same or different and each are a halogen atom, an optionally substituted $C_{1-3}$ alkyl group, an optionally substituted $C_{1-3}$ alkylamino group or an optionally protected amino group is further preferred.

A compound in which m number of $R^4$ are the same or different and each are a halogen atom or an optionally substituted $C_{1-3}$ alkyl group is still further preferred. A compound in which each of m number of $R^4$ is a halogen atom is particularly preferred.

In an alternative embodiment, a compound in which m number of $R^4$ are the same or different and each are a halogen atom, a cyano group, an optionally substituted $C_{1-6}$ alkyl group, an optionally substituted $C_{1-6}$ alkoxy group, an optionally substituted carbamoyl group, an optionally substituted $C_{1-6}$ alkylsulfonyl group, an optionally substituted heterocyclic group, an optionally protected amino group, an optionally protected carboxyl group,
an optionally substituted $C_{2-5}$ alkylene group formed together by two adjacent $R^4$, an optionally substituted $C_{2-4}$ alkylene group formed together by one $R^4$ and $R^7$,
a group represented by the general formula $O—Y^1$ formed together by one $R^4$ and $R^7$ wherein $Y^1$ is as defined above,
a group represented by the general formula $S(O)_n—Y^2$ formed together by one $R^4$ and $R^7$ wherein $Y^2$ is as defined above, or
a group represented by the general formula $N(R^8)—Y^3$ formed together by one $R^4$ and $R^7$ wherein $R^8$ and $Y^3$ are as defined above
is preferred.

A compound in which
m number of $R^4$ are the same or different and each are a halogen atom, an optionally substituted $C_{1-3}$ alkyl group, an optionally substituted $C_{1-3}$ alkylamino group, an optionally substituted $C_{1-3}$ alkylsulfonyl group, an optionally protected amino group,
an optionally substituted $C_{2-5}$ alkylene group formed together by two adjacent $R^4$, an optionally substituted $C_{2-4}$ alkylene group formed together by one $R^4$ and $R^7$,
a group represented by the general formula $O—Y^1$ formed together by one $R^4$ and $R^7$ wherein $Y^1$ is as defined above,
a group represented by the general formula $S(O)_n—Y^2$ formed together by one $R^4$ and $R^7$ wherein $Y^2$ is as defined above, or
a group represented by the general formula $N(R^8)—Y^3$ formed together by one $R^4$ and $R^7$ wherein $R^8$ and $Y^3$ are as defined above
is more preferred.

A compound in which
m number of $R^4$ are the same or different and each are a halogen atom, an optionally substituted $C_{1-3}$ alkyl group, an optionally substituted $C_{1-3}$ alkylsulfonyl group,
an optionally substituted $C_{2-3}$ alkylene group formed together by two adjacent $R^4$, an optionally substituted $C_{2-4}$ alkylene group formed together by one $R^4$ and $R^7$,
a group represented by the general formula $O—Y^1$ formed together by one $R^4$ and $R^7$ wherein $Y^1$ is as defined above,
a group represented by the general formula $S(O)_n—Y^2$ formed together by one $R^4$ and $R^7$ wherein $Y^2$ is as defined above, or
a group represented by the general formula $N(R^8)—Y^3$ formed together by one $R^4$ and $R^7$ wherein $R^8$ and $Y^3$ are as defined above
is further preferred.

A compound in which
m number of $R^4$ are the same or different and each are a halogen atom, an optionally substituted $C_{1-3}$ alkyl group, an optionally substituted $C_{1-3}$ alkylsulfonyl group,
an optionally substituted $C_{2-3}$ alkylene group formed together by two adjacent $R^4$, an optionally substituted $C_{2-3}$ alkylene group formed together by one $R^4$ and $R^{7a}$, or
a group represented by the general formula $O—Y^{1a}$ formed together by one $R^4$ and $R^{7a}$ wherein $Y^{1a}$ is defined above
is still further preferred.

A compound in which
m number of $R^4$ are the same or different and each are an optionally substituted $C_{1-3}$ alkyl group,
an optionally substituted $C_{2-3}$ alkylene group formed together by two adjacent $R^4$, or
an optionally substituted $C_{2-3}$ alkylene group formed together by one $R^4$ and $R^{7b}$ is particularly preferred.

A compound in which m number of $R^4$ are the same or different and each are an optionally substituted $C_{1-3}$ alkyl group or an optionally substituted $C_{2-3}$ alkylene group formed together by one $R^4$ and $R^{7b}$ is most preferred.

In a further alternative embodiment, a compound in which m number of $R^4$ are the same or different and each are a halogen atom is preferred.

"m" is an integer of 0 to 5.

A compound in which m is an integer of 0 to 2 is preferred.

$R^5$ is a hydrogen atom, a halogen atom or an optionally substituted $C_{1-6}$ alkyl group.

A compound in which $R^5$ is a hydrogen atom is preferred.

$R^6$ is a hydrogen atom, an amino-protective group or an optionally substituted $C_{1-6}$ alkyl group.

A compound in which $R^6$ is a hydrogen atom or an optionally substituted $C_{1-3}$ alkyl group is preferred. A compound in which $R^6$ is an optionally substituted $C_{1-3}$ alkyl group is more preferred.

$R^7$ is a hydrogen atom, an amino-protective group or an optionally substituted $C_{1-6}$ alkyl group. Alternatively, $R^7$ is, together with one substituent $R^4$ on ring A, an optionally substituted $C_{2-4}$ alkylene group, a group represented by the general formula O—$Y^1$ wherein $Y^1$ is as defined above, a group represented by the general formula S(O)$_n$—$Y^2$ wherein $Y^2$ and n are as defined above, or a group represented by the general formula N($R^8$)—$Y^3$ wherein $Y^3$ and $R^8$ are as defined above.

A compound in which $R^7$ is an optionally substituted $C_{1-3}$ alkyl group, or a compound in which $R^7$ is, together with one substituent $R^4$ on ring A, an optionally substituted $C_{2-3}$ alkylene group, a group represented by the general formula O—$Y^{1a}$ wherein $Y^{1a}$ is as defined above, or a group represented by the general formula N($R^{8a}$)—$Y^3$ wherein $R^{8a}$ represents an optionally substituted $C_{1-3}$ alkyl group; and $Y^3$ is as defined above is preferred.

A compound in which $R^7$ is an optionally substituted $C_{1-3}$ alkyl group, or a compound in which $R^7$ is, together with one substituent $R^4$ on ring A, an optionally substituted $C_{2-3}$ alkylene group or a group represented by the general formula O—$Y^{1a}$ wherein $Y^{1a}$ is as defined above is more preferred.

A compound in which $R^7$ is an optionally substituted $C_{1-3}$ alkyl group, or a compound in which $R^7$ is, together with one substituent $R^4$ on ring A, an optionally substituted $C_{2-3}$ alkylene group is further preferred.

$R^8$ is a hydrogen atom, an amino-protective group, an optionally substituted $C_{1-6}$ alkyl group or an optionally substituted aryl group.

A compound in which $R^8$ is a hydrogen atom or an optionally substituted $C_{1-6}$ alkyl group is preferred. A compound in which $R^8$ is a hydrogen atom is more preferred.

$Y^1$ is an optionally substituted $C_{1-3}$ alkylene group.

A compound in which $Y^1$ is an ethylene group is preferred.

$Y^2$ is an optionally substituted $C_{1-3}$ alkylene group.

A compound in which $Y^2$ is a $C_{1-3}$ alkylene group is preferred.

$Y^3$ is an optionally substituted $C_{1-3}$ alkylene group.

A compound in which $Y^3$ is a $C_{1-3}$ alkylene group is preferred.

In an alternative embodiment, a compound in which
$R^2$ is a hydrogen atom or an optionally substituted $C_{1-6}$ alkyl group; and
each of $Z^1$, $Z^2$ and $Z^3$ is CH
is preferred.

In an alternative embodiment, a compound in which
$R^1$ is a $C_{1-3}$ alkyl group, and
$R^3$ is an optionally substituted $C_{1-6}$ alkyl group, an optionally substituted $C_{3-8}$ cycloalkyl group,
an optionally substituted aryl group or an optionally substituted heterocyclic group
is preferred.

In an alternative embodiment, a compound in which
$X^1$ is a group represented by the general formula C(=O)N($R^{6a}$) wherein $R^{6a}$ is as defined above;
m number of $R^4$ are the same or different and each are a halogen atom, an optionally substituted $C_{1-3}$ alkyl group, an optionally substituted $C_{1-3}$ alkylamino group or an optionally protected amino group; and
m is an integer of 0 to 2
is preferred.

In an alternative embodiment, a compound in which
$R^3$ is an optionally substituted $C_{1-6}$ alkyl group, an optionally substituted $C_{3-8}$ cycloalkyl group or an optionally substituted heterocyclic group;

$X^1$ is a group represented by the general formula C(=O)N($R^{6b}$) wherein $R^{6b}$ is as defined above;
m number of $R^4$ are the same or different and each are a halogen atom or an optionally
substituted $C_{1-3}$ alkyl group; and
m is an integer of 0 to 2
is preferred.

In an alternative embodiment, a compound in which
$R^3$ is an optionally substituted $C_{1-6}$ alkyl group, an optionally substituted $C_{3-8}$ cycloalkyl group or an optionally substituted heterocyclic group;
$X^1$ is a group represented by the general formula N($R^{7a}$)C(=O) wherein $R^{7a}$ is as defined above;
in number of $R^4$ are the same or different and each are a halogen atom, an optionally substituted $C_{1-3}$ alkyl group, an optionally substituted $C_{1-3}$ alkylsulfonyl group,
an optionally substituted $C_{2-3}$ alkylene group formed together by two adjacent $R^4$,
an optionally substituted $C_{2-3}$ alkylene group formed together by one $R^4$ and $R^{7a}$, or
a group represented by the general formula O—$Y^1$ formed together by one $R^4$ and $R^{7a}$ wherein
$Y^{1a}$ is as defined above; and
m is an integer of 0 to 2
is preferred.

A compound in which
$R^3$ is an optionally substituted heterocyclic group;
$X^1$ is a group represented by the general formula N($R^{7b}$)C(=O) wherein $R^{7b}$ is as defined above;
m number of $R^4$ are the same or different and each are an optionally substituted $C_{1-3}$ alkyl group,
an optionally substituted $C_{2-3}$ alkylene group formed together by two adjacent $R^4$, or
an optionally substituted $C_{2-3}$ alkylene group formed together by one $R^4$ and $R^{7b}$; and
m is an integer of 0 to 2
is more preferred.

A compound in which
$R^3$ is an optionally substituted heterocyclic group;
$X^1$ is a group represented by the general formula N($R^{7b}$)C(=O) wherein e is as defined above;
m number of $R^4$ are the same or different and each are an optionally substituted $C_{1-3}$ alkyl group, or
an optionally substituted $C_{2-3}$ alkylene group formed together by one $R^4$ and $R^{7b}$; and
m is an integer of 0 to 2
is further preferred.

In an alternative embodiment, a compound in which
$R^3$ is an optionally substituted $C_{1-6}$ alkyl group or an optionally substituted heterocyclic group;
$X^1$ is an optionally substituted divalent cyclic hydrocarbon group resulting from the removal of one hydrogen atom from each of two adjacent atoms or an optionally substituted divalent heterocyclic group resulting from the removal of one hydrogen atom from each of two adjacent atoms;
m number of $R^4$ are the same or different and each are a halogen atom;
m is an integer of 0 to 2
is preferred.

A compound in which
$R^3$ is an optionally substituted heterocyclic group;
$X^1$ is an optionally substituted divalent heterocyclic group resulting from the removal of one hydrogen atom from each of two adjacent atoms;
m number of $R^4$ are the same or different and each are a halogen atom; and
m is an integer of 0 to 2
is more preferred.

Examples of preferred compounds according to the present invention include the following compounds.

6-(3,4-dihydroquinolin-1(2H)-ylcarbonyl)-1-ethyl-4-(1-methylpiperidin-4-yl)quinolin-2(1H)-one, 1-ethyl-N-methyl-N-(4-methylphenyl)-4-(1-methylpiperidin-4-yl)-2-oxo-1,2-dihydroquinoline-6-carboxamide, N-(2,3-dihydro-1H-inden-5-yl)-1-ethyl-N-methyl-4-(1-methylpiperidin-4-yl)-2-oxo-1,2-dihydroquinoline-6-carboxamide, 6-(5-(4-chlorophenyl)-2-oxo-2,3-dihydro-1H-imidazol-1-yl)-1-ethyl-4-(morpholin-4-yl)quinolin-2(1H)-one, 6-(5-(4-chlorophenyl)-3-methyl-2-oxo-2,3-dihydro-1H-imidazol-1-yl)-1-ethyl-4-(morpholin-4-yl)quinolin-2(1H)-one, 1-ethyl-4-(morpholin-4-yl)-6-(2-oxo-5-phenyl-3-(propan-2-yl)-2,3-dihydro-1H-imidazol-1-yl)quinolin-2(1H)-one, 1-ethyl-N-(3-fluoro-4-methylphenyl)-N-methyl-4-(1-methylpiperidin-4-yl)-2-oxo-1,2-dihydroquinoline-6-carboxamide, N-(3-chloro-4-methylphenyl)-1-ethyl-N-methyl-4-(1-methylpiperidin-4-yl)-2-oxo-1,2-dihydroquinoline-6-carboxamide and N-(3,4-dimethylphenyl)-1-ethyl-N-methyl-4-(1-methylpiperidin-4-yl)-2-oxo-1,2-dihydroquinoline-6-carboxamide.

Examples of the salt of the compound represented by the general formula [1] can include a usually known salt of a basic group such as an amino group or an acidic group such as a hydroxyl group or a carboxyl group.

Examples of the salt of a basic group include: a salt with a mineral acid such as hydrochloric acid, hydrobromic acid, nitric acid and sulfuric acid; a salt with an organic carboxylic acid such as formic acid, acetic acid, citric acid, oxalic acid, fumaric acid, maleic acid, succinic acid, malic acid, tartaric acid, aspartic acid, trichloroacetic acid and trifluoroacetic acid; and a salt with a sulfonic acid such as methanesulfonic acid, benzenesulfonic acid, p-toluenesulfonic acid, mesitylenesulfonic acid and naphthalenesulfonic acid.

Examples of the salt of an acidic group include: a salt with an alkali metal such as sodium and potassium; a salt with an alkaline earth metal such as calcium and magnesium; an ammonium salt; and a salt with a nitrogen-containing organic base such as trimethylamine, triethylamine, tributylamine, pyridine, N,N-dimethylaniline, N-methylpiperidine, 4-methylmorpholine, diethylamine, dicyclohexylamine, procaine, dibenzylamine, N-benzyl-β-phenethylamine, 1-ephenamine and N,N'-dibenzylethylenediamine.

Among the salts described above, examples of preferred salts include pharmacologically acceptable salts.

When the compound represented by the general formula [1] has isomers (e.g., optical isomers, geometric isomers and tautomers), the present invention encompasses these isomers and also encompasses solvates, hydrates and various forms of crystals.

Next, methods for producing the compound of the present invention will be described.

The compound of the present invention is produced by a combination of methods known per se in the art and can be produced according to, for example, the following production methods:

[Production method 1]

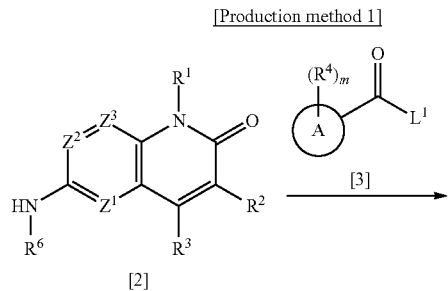

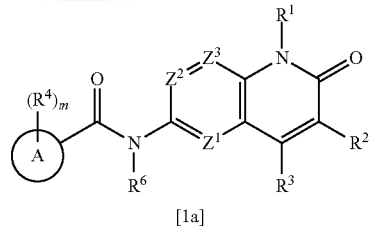

wherein $L^1$ represents a hydroxyl group or a leaving group; and $R^1$, $R^2$, $R^3$, $R^4$, $R^6$, $Z^1$, $Z^2$, $Z^3$, A and in are as defined above.

(1-1) In the Case where $L^1$ is a Hydroxyl Group

For example, p-chlorobenzoic acid is known as the compound represented by the general formula [3].

The compound represented by the general formula [1a] can be produced by reacting the compound represented by the general formula [2] with the compound represented by the general formula [3] in the presence of a condensing agent or an acid halide and in the presence of a base.

The solvent for use in this reaction is not particularly limited as long as the solvent does not influence the reaction. Examples thereof include halogenated hydrocarbons, ethers, esters, amides, nitriles, sulfoxides and aromatic hydrocarbons. These solvents may be used as a mixture.

Preferred examples of the solvent include halogenated hydrocarbons, ethers, esters and amides. Halogenated hydrocarbons and amides are more preferred.

The amount of the solvent used is not particularly limited and can be 1 to 500 times (v/w) the amount of the compound represented by the general formula [2].

Examples of the base for use in this reaction include an inorganic base and an organic base.

Preferred examples of the base include an organic base. Triethylamine, N,N-diisopropylethylamine and 4-methylmorpholine are more preferred, and N,N-diisopropylethylamine and 4-methylmorpholine are further preferred.

The amount of the base used can be 1 to 50 times, preferably 1 to 10 times the mol of the compound represented by the general formula [2].

Examples of the condensing agent for use in this reaction include: carbodiimides such as N,N-diisopropylcarbodiimide (DIC), N,N'-di-(tert-butyl)carbodiimide, N,N'-dicyclohexylcarbodiimide (DCC), N-(tert-butyl)-N-ethylcarbodiimide (BEC), N-cyclohexyl-N'-(2-morpholinoethyl)carbodiimide (CMC) and 1-ethyl-3-(3-dimethylaminopropyl)carbodiimide (EDC); imidazoliums such as 1,1'-carbonyldiimidazole (CDI) and 1,1'-carbonyldi(1,2,4-triazole) (CDT); acid azides such as diphenylphosphorylazide; acid cyanides such as diethylphosphorylcyanide; 2-ethoxy-1-ethoxycarbonyl-1,2-dihydroquinoline; and uroniums such as O-(benzotriazol-1-yl)-N,N,N',N'-tetramethyluronium hexafluorophosphate (HBTU), O-(7-azabenzotriazol-1-yl)-N,N,N',N'-tetramethyluronium hexafluorophosphate (HATU), O-(benzotriazol-1-yl)-N,N,N',N'-bis(tetramethylene)uronium hexafluorophosphate (HBPyU), O-(benzotriazol-1-yl)-N,N,N',N'-bis(pentamethylene)uronium hexafluorophosphate (HBPipU), O-(6-chlorobenzotriazol-1-yl)-N,N,N',N'-tetramethyluronium hexafluorophosphate (HCTU), O-(3,4-dihydro-4-oxo-1,2,3-benzotriazin-3-yl)-N,N,N',N'-tetramethyluronium hexafluorophosphate (HDBTU), O-(2-oxo-1(2H)pyridyl)-N,N,N',N'-tetramethyluronium hexafluorophosphate (TPTU), O-((ethoxycarbonyl)cyanomethyleneamino)-N,N,N',N'-tetramethyluronium hexafluorophosphate (HOTU), O-((ethoxycarbonyl)cyanomethyleneamino)-N,N,N',N'-tetramethyluronium tetrafluoroborate (TOTU), N,N,N',N'-tetramethyl-O—(N-succinimidyl)uronium hexafluorophosphate (HSTU), N,N,N',N'-tetramethyl-O—(N-succinimidyl)uronium tetrafluoroborate (TSTU) dipyrrolidino(N-succinimidyloxy)carbenium hexafluorophosphate (HSPyU) and S-(1-oxido-2-pyridyl)-N,N,N',N'-tetramethylthiouronium tetrafluoroborate (TOTT).

Preferred examples of the condensing agent include carbodiimides. EDC is more preferred.

The amount of the condensing agent used can be 1 to 50 times, preferably 1 to 5 times the mol of the compound represented by the general formula [2].

In the case of using a carbodiimide as the condensing agent, it is preferred to add an additive.

Examples of the additive include 1-hydroxybenzotriazole (HOBT), 1-hydroxy-7-azabenzotriazole (HOAT) and ethyl (hydroxyimino)cyanoacetate. HOBT and ethyl (hydroxyimino)cyanoacetate are preferred.

The amount of the additive used can be 0.01 to 10 times, preferably 0.1 to 1 times the mol of the compound represented by the general formula [2].

Examples of the acid halide for use in this reaction include: oxalyl chloride; carboxylic acid halides such as acetyl chloride and trifluoroacetyl chloride; sulfonic acid halides such as methanesulfonyl chloride and tosyl chloride; and chloroformic acid esters such as ethyl chloroformate and isobutyl chloroformate.

The amount of the compound represented by the general formula [3] used is not particularly limited and can be 1 to 10 times the mol of the compound represented by the general formula [2].

This reaction can be carried out at −30 to 150° C., preferably 0 to 100° C., for 30 minutes to 48 hours.

(1-2) In the Case where $L^1$ is a Leaving Group

For example, p-chlorobenzoyl chloride is known as the compound represented by the general formula [3].

The compound represented by the general formula [1a] can be produced by reacting the compound represented by the general formula [2] with the compound represented by the general formula [3] in the presence of a base.

The solvent for use in this reaction is not particularly limited as long as the solvent does not influence the reaction. Examples thereof include halogenated hydrocarbons, ethers, esters, amides, nitriles, sulfoxides and aromatic hydrocarbons. These solvents may be used as a mixture.

Preferred examples of the solvent include halogenated hydrocarbons, ethers and esters. Halogenated hydrocarbons are more preferred.

The amount of the solvent used is not particularly limited and can be 1 to 500 times (v/w) the amount of the compound represented by the general formula [2].

Examples of the base for use in this reaction include an inorganic base and an organic base.

Preferred examples of the base include an organic base. Triethylamine, N,N-diisopropylethylamine, 4-methylmorpholine and pyridine are more preferred, and N,N-diisopropylethylamine, 4-methylmorpholine and pyridine are further preferred.

The amount of the base used can be 1 to 50 times, preferably 1 to 10 times the mol of the compound represented by the general formula [2].

The amount of the compound represented by the general formula [3] used is not particularly limited and can be 1 to 10 times the mol of the compound represented by the general formula [2].

This reaction can be carried out at −30 to 150° C., preferably 0 to 100° C., for 30 minutes to 48 hours.

[Production method 2]

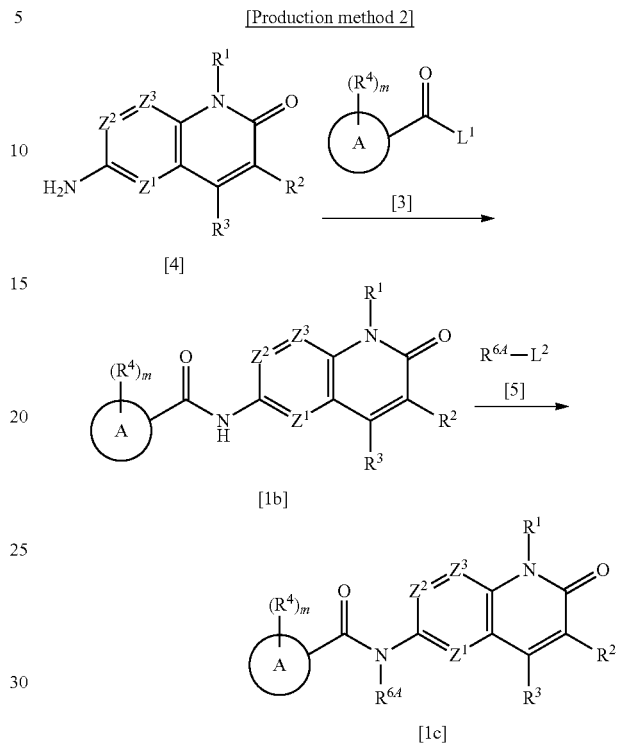

wherein $R^{6A}$ represents an optionally substituted $C_{1-6}$ alkyl group; $L^2$ represents a leaving group; and $R^1$, $R^2$, $R^3$, $R^4$, $L^1$, $Z^1$, $Z^2$, $Z^3$, A and m are as defined above.

<Step 1>

The compound represented by the general formula [1b] can be produced by reacting the compound represented by the general formula [4] with the compound represented by the general formula [3].

This reaction can be carried out according to Production method 1.

<Step 2>

For example, methyl iodide is known as the compound represented by the general formula [5].

The compound represented by the general formula [1c] can be produced by reacting the compound represented by the general formula [1b] with the compound represented by the general formula [5] in the presence of a base.

The solvent for use in this reaction is not particularly limited as long as the solvent does not influence the reaction. Examples thereof include halogenated hydrocarbons, ethers, ketones, esters, amides, nitriles, sulfoxides and aromatic hydrocarbons. These solvents may be used as a mixture.

Preferred examples of the solvent include ethers and amides. Amides are more preferred.

The amount of the solvent used is not particularly limited and can be 1 to 500 times (v/w) the amount of the compound represented by the general formula [1b].

Examples of the base for use in this reaction include: an organic base such as sodium methoxide, sodium ethoxide, potassium tert-butoxide, pyridine, dimethylaminopyridine and triethylamine; and an inorganic base such as sodium hydride, sodium hydroxide, potassium hydroxide, sodium bicarbonate, potassium carbonate and sodium carbonate. Preferred examples of the base include sodium hydride and potassium carbonate.

The amount of the base used is not particularly limited and can be 1 to 20 times, preferably 1 to 5 times the mol of the compound represented by the general formula [1b].

The amount of the compound represented by the general formula [5] used is not particularly limited and can be 1 to 10 times the mol of the compound represented by the general formula [1b].

This reaction can be carried out at −30 to 150° C., preferably 0 to 100° C., for 30 minutes to 48 hours.

[Production method 3]

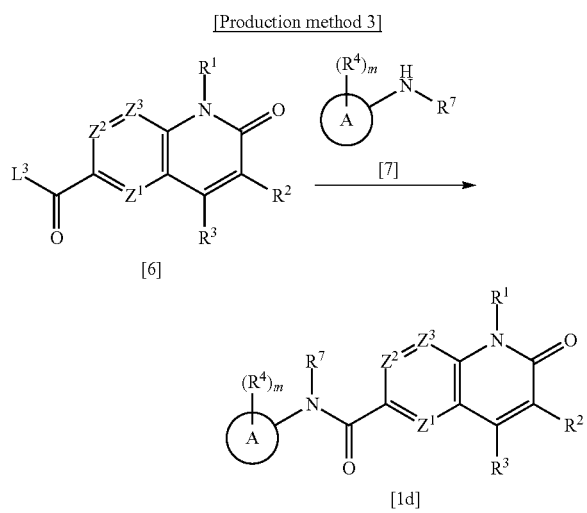

[1d]

wherein $L^3$ represents a hydroxyl group or a leaving group; and $R^1$, $R^2$, $R^3$, $R^4$, $R^7$, $Z^1$, $Z^2$, $Z^3$, A and m are as defined above.

For example, N-methylaniline is known as the compound represented by the general formula [7].

The compound represented by the general formula [1d] can be produced by reacting the compound represented by the general formula [6] with the compound represented by the general formula [7].

This reaction can be carried out according to Production method 1.

[Production method 4]

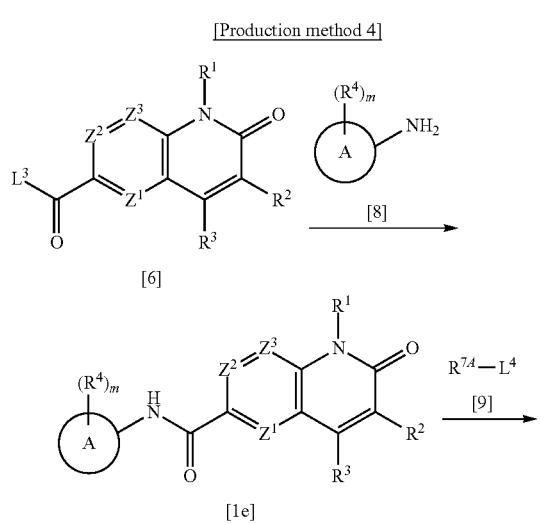

[1e]

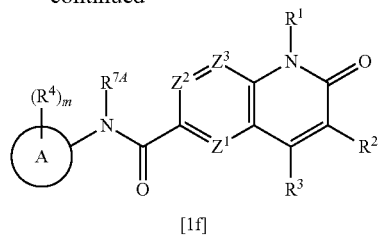

[1f]

wherein $R^{7A}$ represents an optionally substituted $C_{1-6}$ alkyl group; $L^4$ represents a leaving group; and $R^1$, $R^2$, $R^3$, $R^4$, $L^3$, $Z^1$, $Z^2$, $Z^3$, A and m are as defined above.

<Step 1>

The compound represented by the general formula [1e] can be produced by reacting the compound represented by the general formula [6] with the compound represented by the general formula [8].

This reaction can be carried out according to Production method 1.

<Step 2>

For example, methyl iodide is known as the compound represented by the general formula [9].

The compound represented by the general formula [1f] can be produced by reacting the compound represented by the general formula [1e] with the compound represented by the general formula [9].

This reaction can be carried out according to <Step 2> of Production method 2.

[Production method 5]

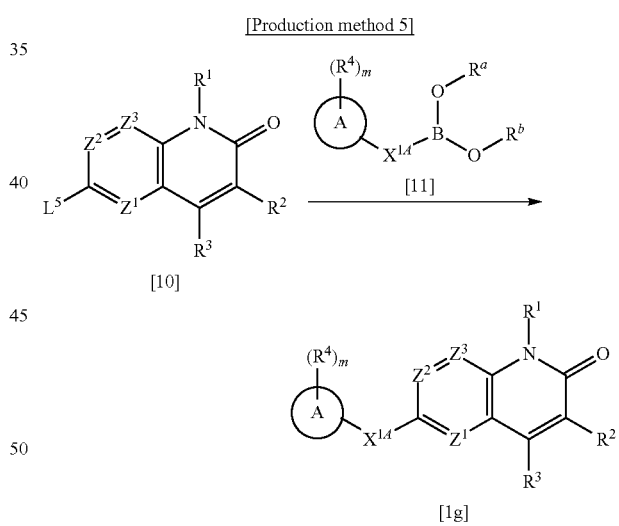

[1g]

wherein $R^a$ represents a hydrogen atom or an optionally substituted $C_{1-6}$ alkyl group; $R^b$ represents a hydrogen atom or an optionally substituted $C_{1-6}$ alkyl group; or $R^a$ and $R^b$ together represent an optionally substituted $C_{1-3}$ alkylene group; $L^5$ represents a leaving group; $X^{1A}$ represents an optionally substituted divalent cyclic hydrocarbon group resulting from the removal of one hydrogen atom from each of two adjacent atoms or an optionally substituted divalent heterocyclic group resulting from the removal of one hydrogen atom from each of two adjacent atoms; and $R^1$, $R^2$, $R^3$, $R^4$, $Z^1$, $Z^2$, $Z^3$, A and m are as defined above.

For example, 2-biphenylboric acid is known as the compound represented by the general formula [11].

The compound represented by the general formula [1g] can be produced by reacting the compound represented by the general formula [10] with the compound represented by the general formula [11] in the presence or absence of a base, in the presence of a palladium catalyst and in the presence or absence of a ligand.

The solvent for use in this reaction is not particularly limited as long as the solvent does not influence the reaction. Examples thereof include water, alcohols, halogenated hydrocarbons, ethers, ketones, esters, amides, nitriles, sulfoxides and aromatic hydrocarbons. These solvents may be used as a mixture.

Preferred examples of the solvent include mixed solvents of aromatic hydrocarbons and water and mixed solvents of ethers and water.

The amount of the solvent used is not particularly limited and can be 1 to 500 times (v/w) the amount of the compound represented by the general formula [10].

Examples of the palladium catalyst for use in this reaction include: metal palladium such as palladium-carbon and palladium black; an inorganic palladium salt such as palladium chloride; an organic palladium salt such as palladium acetate; chloro(2-(dicyclohexylphosphino)-3,6-dimethoxy-2',4',6'-triisopropyl-1,1'-biphenyl)(2-(2-aminoethyl)phenyl)palladium(II); an organic palladium complex such as tetrakis(triphenylphosphine)palladium(0), bis(triphenylphosphine)palladium(II) dichloride, bis(di-tert-butyl(4-dimethylaminophenyl)phosphine)dichloropalladium(II), 1,1'-bis(diphenylphosphino)ferrocene palladium(II) dichloride, (E)-di(μ-acetato)bis(o-(di-o-tolylphosphino)benzyl)dipalladium(II) and tris(dibenzylideneacetone)dipalladium(0); and a polymer-supported organic palladium complex such as polymer-supported bis(acetato)triphenylphosphine palladium(II) and polymer-supported di(acetato)dicyclohexylphenylphosphine palladium(II). An organic palladium complex is preferred.

The amount of the palladium catalyst used can be 0.00001 to 1 times, preferably, 0.01 to 0.2 times the mol of the compound represented by the general formula [10].

Examples of the ligand that is used in this reaction, if desired, include: trialkylphosphines such as trimethylphosphine and tri-tert-butylphosphine; tricycloalkylphosphines such as tricyclohexylphosphine; triarylphosphines such as triphenylphosphine and tritolylphosphine; trialkyl phosphites such as trimethyl phosphite, triethyl phosphite and tributyl phosphite; tricycloalkyl phosphites such as tricyclohexyl phosphite; triaryl phosphites such as triphenyl phosphite; imidazolium salts such as 1,3-bis(2,4,6-trimethylphenyl)imidazolium chloride; diketones such as acetylacetone and octafluoroacetylacetone; amines such as trimethylamine, triethylamine, tripropylamine, triisopropylamine and tributylamine; 1,1'-bis(diphenylphosphino)ferrocene; 2,2'-bis(diphenylphosphino)-1,1'-binaphthyl; 2-dicyclohexylphosphino-2,',6'-dimethoxybiphenyl; 2-dicyclohexylphosphino-2',4',6'-triisopropylbiphenyl; 2-(di-tert-butylphosphino)-2',4',6'-triisopropylbiphenyl; 2-dicyclohexylphosphino-2'-(N,N-dimethylamino)biphenyl; 4,5-bis(diphenylphosphino)-9,9-dimethylxanthene; and 2-(di-tert-butylphosphino)biphenyl.

The amount of the ligand used can be 0.00001 to 1 times, preferably 0.02 to 0.5 times the mol of the compound represented by the general formula [10].

Examples of the base that is used in this reaction, if desired, include an inorganic base and an organic base. An inorganic base such as sodium bicarbonate, sodium carbonate, potassium carbonate, cesium carbonate and tripotassium phosphate is preferred.

The amount of the base used can be 1 to 50 times, preferably 2 to 10 times the mol of the compound represented by the general formula [10].

The amount of the compound represented by the general formula [11] used can be 1 to 50 times, preferably 1 to 2 times the mol of the compound represented by the general formula [10].

This reaction can usually be carried out at 0 to 160° C., preferably 20 to 120° C., for 1 minute to 96 hours in an inert gas (e.g. nitrogen and/or argon) atmosphere.

[Production method 6]

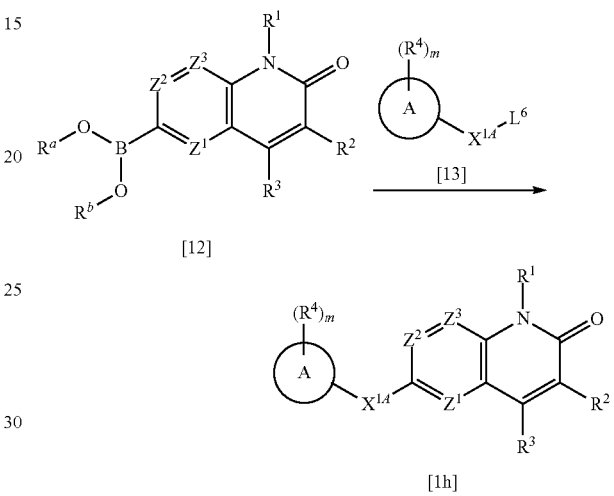

wherein $L^6$ represents a leaving group; and $R^1$, $R^2$, $R^3$, $R^4$, $R^a$, $R^b$, $X^{1A}$, $Z^1$, $Z^2$, $Z^3$, A and m are as defined above.

The compound represented by the general formula [1h] can be produced by reacting the compound represented by the general formula [12] with the compound represented by the general formula [13].

This reaction can be carried out according to Production method 5.

[Production method 7]

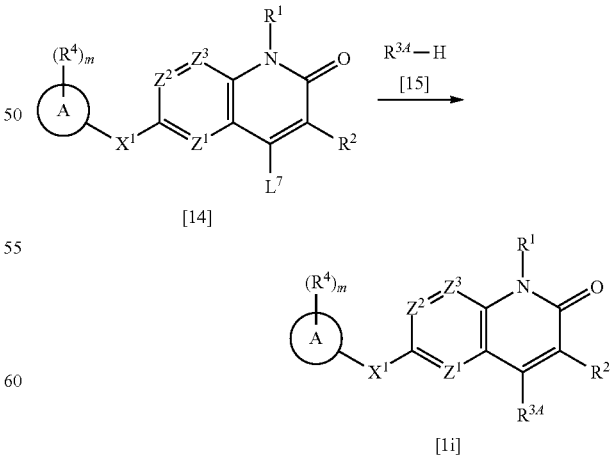

wherein $R^{3A}$ represents an optionally substituted $C_{1-6}$ alkylamino group, an optionally substituted di($C_{1-6}$ alkylamino group or an optionally substituted cyclic amino group; $L^7$ represents a leaving group; and $R^1$, $R^2$, $R^4$, $X^1$, $Z^1$, $Z^2$, $Z^3$, A and m are as defined above.

For example, morpholine is known as the compound represented by the general formula [15].

The compound represented by the general formula [1i] can be produced by reacting the compound represented by the general formula [14] with the compound represented by the general formula [15] in the presence or absence of a base.

The solvent for use in this reaction is not particularly limited as long as the solvent does not influence the reaction. Examples thereof include halogenated hydrocarbons, ethers, esters, amides, nitriles, sulfoxides and aromatic hydrocarbons. These solvents may be used as a mixture.

Preferred examples of the solvent include halogenated hydrocarbons, ethers, esters and amides. Amides are more preferred.

The amount of the solvent used is not particularly limited and can be 1 to 500 times (v/w) the amount of the compound represented by the general formula [14].

Examples of the base for use in this reaction include an inorganic base and an organic base.

Preferred examples of the base include an organic base. Triethylamine, N,N-diisopropylethylamine and 4-methylmorpholine are more preferred, and N,N-diisopropylethylamine and 4-methylmorpholine are further preferred.

The amount of the base used can be 1 to 50 times, preferably 1 to 10 times the mol of the compound represented by the general formula [14].

The amount of the compound represented by the general formula [15] used is not particularly limited and can be 1 to 10 times the mol of the compound represented by the general formula [14].

This reaction can be carried out at −30 to 150° C., preferably 0 to 150° C., for 30 minutes to 48 hours.

Next, methods for producing starting materials for the production of the compound of the present invention will be described.

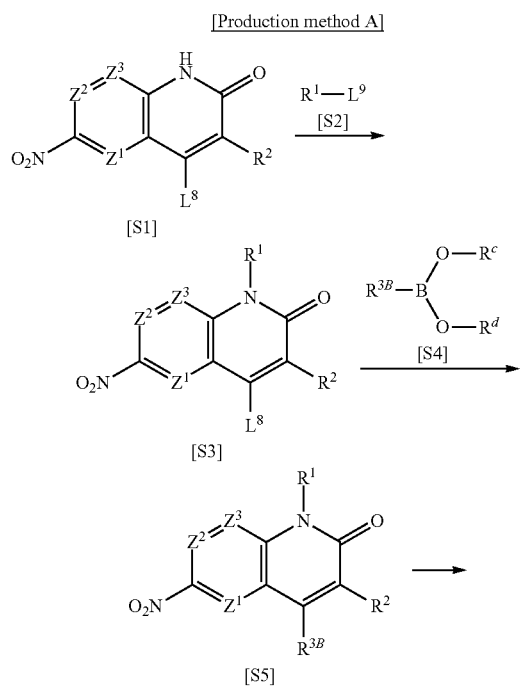

[Production method A]

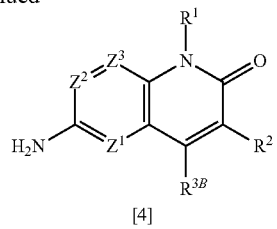

[4]

wherein $R^{3B}$ represents an optionally substituted $C_{1-6}$ alkyl group, an optionally substituted $C_{3-8}$ cycloalkyl group, an optionally substituted aryl group or an optionally substituted heterocyclic group; $R^c$ represents a hydrogen atom or an optionally substituted $C_{1-6}$ alkyl group; $R^d$ represents a hydrogen atom or an optionally substituted $C_{1-6}$ alkyl group; or $R^c$ and $R^d$ together represent an optionally substituted $C_{1-3}$ alkylene group; $L^8$ represents a leaving group; $L^9$ represents a leaving group; and $R^1$, $R^2$, $Z^1$, $Z^2$ and $Z^3$ are as defined above.

<Step 1>

For example, 4-chloro-6-nitroquinolin-2(1H)-one is known as the compound represented by the general formula [S1].

For example, ethyl iodide is known as the compound represented by the general formula [S2].

The compound represented by the general formula [S3] can be produced by reacting the compound represented by the general formula [S1] with the compound represented by the general formula [S2] in the presence of a base.

The solvent for use in this reaction is not particularly limited as long as the solvent does not influence the reaction. Examples thereof include halogenated hydrocarbons, ethers, esters, amides, nitriles, sulfoxides and aromatic hydrocarbons. These solvents may be used as a mixture.

Preferred examples of the solvent include amides and sulfoxides. Amides are more preferred.

The amount of the solvent used is not particularly limited and can be 1 to 500 times (v/w) the amount of the compound represented by the general formula [S1].

Examples of the base for use in this reaction include an inorganic base and an organic base.

Preferred examples of the base include an inorganic base. Cesium carbonate is more preferred.

The amount of the base used can be 1 to 50 times, preferably 1 to 10 times the mol of the compound represented by the general formula [S1].

The amount of the compound represented by the general formula [S2] used is not particularly limited and can be 1 to 10 times the mol of the compound represented by the general formula [S1].

This reaction can be carried out at −30 to 150° C., preferably 0 to 100° C., for 30 minutes to 48 hours.

<Step 2>

For example, cyclopropylboric acid is known as the compound represented by the general formula [S4].

The compound represented by the general formula [S5] can be produced by reacting the compound represented by the general formula [S3] with the compound represented by the general formula [S4] in the presence of a base, in the presence of a palladium catalyst and in the presence or absence of a ligand.

This reaction can be carried out according to Production method 5.

29

<Step 3>

The compound represented by the general formula [4] can be produced by subjecting the compound represented by the general formula [S5] to reduction reaction. This reaction can be carried out according to a method described in Richard C. Larock et al., Comprehensive Organic Transformations, 2nd edition, p. 823-827, 1999, John Wiley & Sons, INC. or a method equivalent thereto. Specific examples thereof include catalytic hydrogenation reaction using a metal catalyst, and reduction reaction using a metal such as iron or zinc.

In the case of subjecting the compound represented by the general formula [S5] to the catalytic hydrogenation reaction, the solvent used is not particularly limited as long as the solvent has no adverse effect on the reaction. Examples thereof include water, alcohols, amides, halogenated hydrocarbons, aromatic hydrocarbons, ethers, acetonitrile, ketones, esters, acetic acid and pyridine. These solvents may be used as a mixture.

Examples of the metal catalyst for use in this reaction include: metal palladium such as palladium-carbon and palladium black; a palladium salt such as palladium oxide and palladium hydroxide; nickel metal such as Raney nickel; and a platinum salt such as platinum oxide.

The amount of the metal catalyst used is 0.001 to 5 times (w/w), preferably 0.01 to 1 times (w/w) the amount of the compound represented by the general formula [S5].

Examples of the hydrogen source include: hydrogen; formic acid; formate such as sodium formate, ammonium formate and triethylammonium formate; cyclohexane; and cyclohexadiene.

The amount of the hydrogen source used can be 2 to 100 times, preferably, 2 to 10 times the mol of the compound represented by the general formula [S5].

This reaction can be carried out at 0 to 200° C., preferably 0 to 100° C., for 1 minute to 24 hours.

In the case of subjecting the compound represented by the general formula [S5] to the reduction reaction using a metal, the solvent used is not particularly limited as long as the solvent has no adverse effect on the reaction. Examples thereof include water, alcohols, amides, halogenated hydrocarbons, aromatic hydrocarbons, ethers, acetonitrile, ketones and esters. These solvents may be used as a mixture.

Examples of the metal for use in this reaction include iron, zinc, tin and tin(II) chloride.

The amount of the metal used is 1 to 50 times, preferably 1 to 10 times the mol of the compound represented by the general formula [S5].

Examples of the acid that is used in this reaction, if desired, include hydrogen chloride, hydrogen bromide, acetic acid and ammonium chloride.

The amount of the acid used can be 0.001 to 100 times (v/w), preferably 0.01 to 20 times (v/w) the amount of the compound represented by the general formula [S5].

This reaction can be carried out at 0 to 200° C., preferably 0 to 100° C., for 1 minute to 24 hours.

30

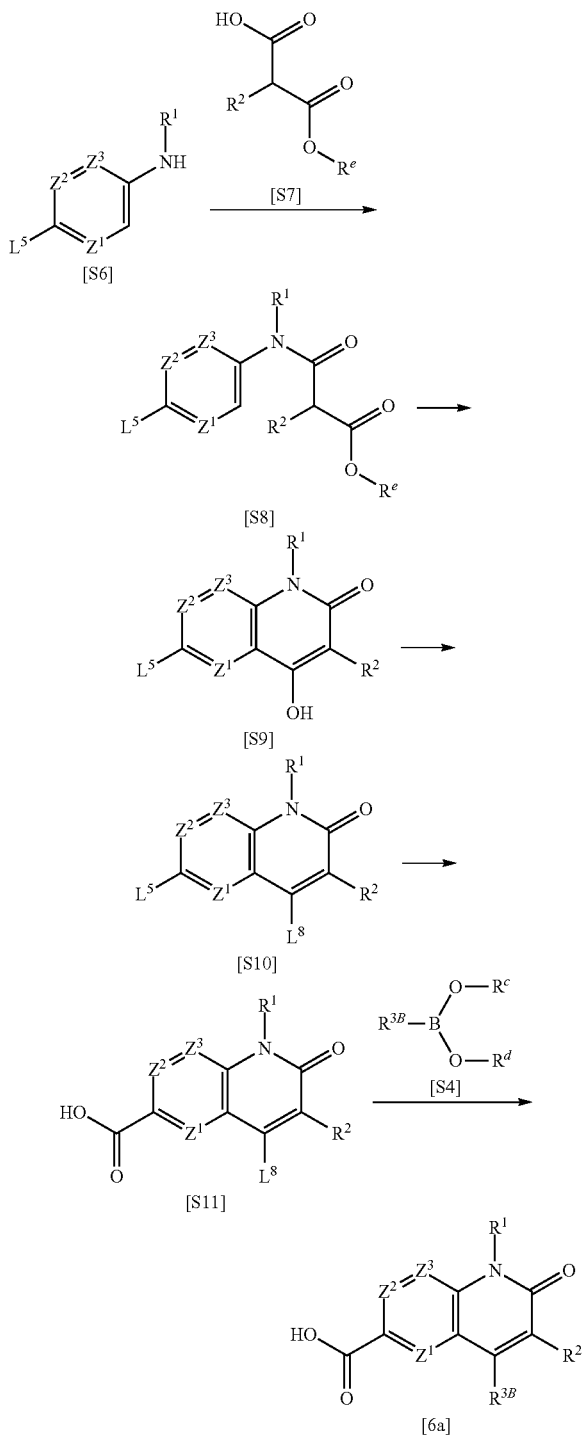

wherein $R^e$ represents a carboxyl-protective group; and $R^1$, $R^2$, $R^{3B}$, $R^c$, $R^d$, $L^5$, $L^8$, $Z^1$, $Z^2$ and $Z^3$ are as defined above.

<Step 1>

For example, N-ethyl-4-iodoaniline is known as the compound represented by the general formula [S6].

For example, 3-tert-butoxy-3-oxopropionic acid is known as the compound represented by the general formula [S7].

The compound represented by the general formula [S8] can be produced by reacting the compound represented by the general formula [S6] with the compound represented by the general formula [S7] in the presence of a condensing agent or an acid halide and in the presence of a base.

This reaction can be carried out according to Production method 1.

<Step 2>

The compound represented by the general formula [S9] can be produced by reacting the compound represented by the general formula [S8] with a dehydrating agent.

The solvent for use in this reaction is not particularly limited as long as the solvent does not influence the reaction. Examples thereof include halogenated hydrocarbons, ethers, esters, amides, nitriles, sulfoxides and aromatic hydrocarbons. These solvents may be used as a mixture.

Preferred examples of the solvent include amides and sulfoxides. Amides are more preferred.

The amount of the solvent used is not particularly limited and can be 1 to 500 times (v/w) the amount of the compound represented by the general formula [S8].

Examples of the dehydrating agent for use in this reaction include diphosphorus pentoxide, phosphorus pentachloride, phosphoryl chloride and thionyl chloride.

The amount of the dehydrating agent used can be 1 to 50 times, preferably 1 to 10 times the mol of the compound represented by the general formula [S8].

This reaction can be carried out at −30 to 150° C., preferably 0 to 100° C., for 30 minutes to 48 hours.

<Step 3>

When $L^8$ is, for example, a halogen atom, the compound represented by the general formula [S10] can be produced by reacting the compound represented by the general formula [S9] with a halogenating agent.

The solvent for use in this reaction is not particularly limited as long as the solvent does not influence the reaction. Examples thereof include aliphatic hydrocarbons, halogenated hydrocarbons, ethers, ketones, esters, amides, nitriles, sulfoxides and aromatic hydrocarbons. These solvents may be used as a mixture.

Preferred examples of the solvent include aromatic hydrocarbons.

The amount of the solvent used is not particularly limited and can be 1 to 500 times (v/w) the amount of the compound represented by the general formula [S9].

Examples of the halogenating agent for use in this reaction include phosphorus oxychloride, phosphoryl chloride and thionyl chloride.

The amount of the halogenating agent used can be 1 to 50 times, preferably 1 to 10 times the mol of the compound represented by the general formula [S9]. Also, the halogenating agent may be used as a solvent.

This reaction can be carried out at −30 to 150° C., preferably 0 to 100° C., for 30 minutes to 48 hours.

<Step 4>

The compound represented by the general formula [S11] can be produced by reacting the compound represented by the general formula [S10] with sodium formate in the presence of a base and in the presence of a palladium catalyst.

The solvent for use in this reaction is not particularly limited as long as the solvent does not influence the reaction. Examples thereof include halogenated hydrocarbons, ethers, esters, amides, nitriles, sulfoxides and aromatic hydrocarbons. These solvents may be used as a mixture.

Preferred examples of the solvent include amides and sulfoxides. Amides are more preferred.

The amount of the solvent used is not particularly limited and can be 1 to 500 times (v/w) the amount of the compound represented by the general formula [S10].

Examples of the base for use in this reaction include an organic base.

The amount of the base used can be 1 to 50 times, preferably 1 to 10 times the mol of the compound represented by the general formula [S10].

Examples of the palladium catalyst for use in this reaction include: metal palladium such as palladium-carbon and palladium black; an inorganic palladium salt such as palladium chloride; an organic palladium salt such as palladium acetate; chloro(2-(dicyclohexylphosphino)-3,6-dimethoxy-2',4',6'-triisopropyl-1,1'-biphenyl)(2-(2-aminoethyl)phenyl) palladium(II); an organic palladium complex such as tetrakis(triphenylphosphine)palladium(0), bis(triphenylphosphine) palladium(II) dichloride, bis(di-tert-butyl(4-dimethylaminophenyl)phosphine)dichloropalladium(II), 1,1'-bis(diphenylphosphino)ferrocene palladium(II) dichloride, (E)-di(μ-acetato)bis(o-(di-o-tolylphosphino)benzyl)dipalladium(II) and tris(dibenzylideneacetone)dipalladium(0); and a polymer-supported organic palladium complex such as polymer-supported bis(acetato)triphenylphosphine palladium(II) and polymer-supported di(acetato)dicyclohexylphenylphosphine palladium(II). An organic palladium complex is preferred.

The amount of the palladium catalyst used can be 0.00001 to 1 times, preferably 0.01 to 0.2 times the mol of the compound represented by the general formula [S10].

The amount of sodium formate used can be 1 to 50 times, preferably 1 to 10 times the mol of the compound represented by the general formula [S10].

This reaction can be carried out at −30 to 150° C., preferably 0 to 100° C., for 30 minutes to 48 hours.

<Step 5>

For example, tert-butyl 4-(4,4,5,5-tetramethyl-1,3,2-dioxaborolan-2-yl)-3,6-dihydropyridine-1(2H)-carboxylate is known as the compound represented by the general formula [S4].

The compound represented by the general formula [6a] can be produced by reacting the compound represented by the general formula [S11] with the compound represented by the general formula [S4] in the presence of a base, in the presence of a palladium catalyst and in the presence or absence of a ligand.

This reaction can be carried out according to Production method 5.

When each compound used in these production methods has solvates, hydrates and various forms of crystals, these solvates, hydrates and various forms of crystals can also be used.

Among the compounds used in these production methods, a compound having, for example, an amino group, a hydroxyl group or a carboxyl group can be subjected to the protection of the group with a usual protective group in advance, and after the reaction, the protective group can be eliminated by a method known per se in the art.

Each compound obtained by these production methods can be converted to a different compound, for example, by subjecting the compound to a reaction known per se in the art such as condensation, addition, oxidation, reduction, dislocation, substitution, halogenation, dehydration or hydrolysis or by appropriately combining these reactions.

In the case of using the compound represented by the general formula [1] as a medicament, the compound represented by the general formula [1] may be appropriately mixed with a pharmaceutical aid usually used in formulation, such as an excipient, a carrier and a diluent. Such a preparation can be administered orally or parenterally in a form such as a tablet, a capsule, a powder, a syrup, granules, a pill, a suspension, an emulsion, a solution, a dust, a suppository, eye drops, nasal drops, ear drops, a patch, an ointment or an injection according to a routine method. The administration method, the dose and the number of doses can be appropriately selected according to the age, body weight and symptoms of a patient. Usually, the compound represented by the general formula [1] can be administered orally or parenterally (e.g. administered through injection, administered through intravenous drip, and administered to a rectal site) to an adult at a daily dose of 0.01 to 1000 mg/kg, which is administered in one portion or several portions.

Examples of the disease involving the overproduction of CXCL10 include an immune disease such as inflammatory bowel disease, arthritis, psoriasis, systemic sclerosis, systemic lupus erythematosus and autoimmune neuroinflammatory disease.

The pharmaceutical composition means a composition containing the compound of the present invention or the salt thereof as an active ingredient appropriately mixed with a pharmaceutical aid usually used in formulation, such as an excipient, a carrier and a diluent.

The agent for treatment means a pharmaceutical composition aimed at treatment.

The treatment includes prophylaxis or therapy. The prophylaxis includes the inhibition of development, reduction in the risk of development and the delay of development. The therapy includes the amelioration of a target disease or condition and the suppression (sustentation or delay) of progression of the disease or the condition. The recipient for the treatment includes a human or a nonhuman animal in need of the treatment.

Next, the present invention will be described with reference to Reference Examples, Examples and Test Examples. However, the present invention is not intended to be limited by them.

Purification by column chromatography employed an automatic purification apparatus ISOLERA (Biotage Japan Ltd.) or a medium-pressure liquid chromatograph YFLC-W Prep 2XY.N (Yamazen Corp.), unless otherwise specified.

The carrier used in silica gel column chromatography was SNAP KP-Sil Cartridge (Biotage Japan Ltd.) or Hi-Flash Column W001, W002, W003, W004 or W005 (Yamazen Corp.), and the carrier used in basic silica gel column chromatography was SNAP KP-NH Cartridge (Biotage Japan Ltd.), unless otherwise specified.

The mixing ratio of an eluent is a volume ratio. For example, "hexane:ethyl acetate gradient elution=100:0–50:50" means that an eluent composed of 100% hexane and 0% ethyl acetate was finally changed to an eluent composed of 50% hexane and 50% ethyl acetate.

The flow hydrogenation reaction apparatus used was H-Cube (ThalesNano Nanotechnology Inc.).

The microwave apparatus used was Initiator+ or Initiator Sixty (both from Biotage Japan Ltd.).

MS spectra were measured using ACQUITY SQD LC/MS System (Waters Corp., ionization method: ESI (electrospray ionization), model M-8000 (Hitachi, Ltd., ionization: ESI), LCMS-2010EV (Shimadzu Corp., ionization: simultaneous ionization method of ESI and APCI (atmospheric pressure chemical ionization)) or JMS-T100LP (DART) (JEOL Ltd., ionization: DART (direct analysis in real time)).

NMR spectra were measured using tetramethylsilane as internal standards and Bruker AV300 (Bruker Corp.) or model JNM-AL400 (JEOL Ltd.), and total δ values were indicated by ppm.

Abbreviations in NMR measurement have the following meanings:
s: Singlet
brs: Broad singlet
d: Doublet
dd: Double doublet
t: Triplet
q: Quartet
quint: Quintet
m: Multiplet
DMSO-$D_6$: deuterated dimethyl sulfoxide Abbreviations in Reference Examples and Examples have the following meanings:
Bn: Benzyl
Me: Methyl

REFERENCE EXAMPLE 1

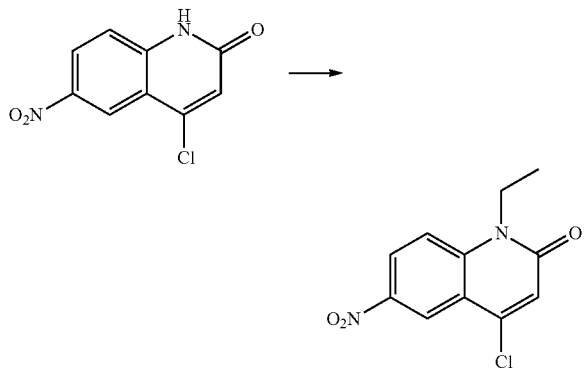

To a suspension of 18.5 g of 4-chloro-6-nitroquinolin-2 (1H)-one in 150 mL of N,N-dimethylacetamide was added 53.8 g of cesium carbonate at 40-50° C. To the reaction mixture under ice cooling was added 7.91 mL of ethyl iodide, and then the mixture was stirred at room temperature for 3 hours. To the reaction mixture were added ethyl acetate and water, and the pH of the mixture was adjusted to 2.0 with 2 mol/L hydrochloric acid. The solid matter was filtered and washed with water to obtain a slightly brown solid. To the obtained solid were added ethyl acetate and diisopropyl ether, and then the solid matter was filtered and washed with ethyl acetate to obtain 8.88 g of 4-chloro-1-ethyl-6-nitro-quinolin-2(1H)-one as a slightly brown solid.

$^1$H-NMR (CDCl$_3$) δ: 1.39 (3H, t, J=7.3 Hz), 4.39 (2H, q, J=7.3 Hz), 7.01 (1H, s), 7.51 (1H, d, J=9.9 Hz), 8.48 (1H, dd, J=9.2, 2.6 Hz), 8.94 (1H, d, J=2.6 Hz).

REFERENCE EXAMPLE 2

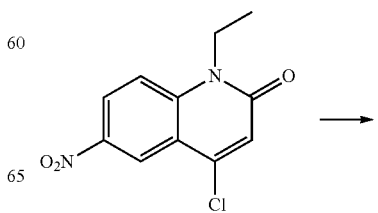

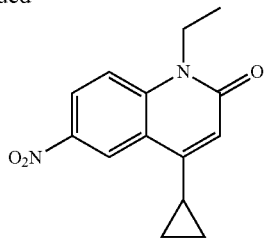

A mixture of 5.17 g of 4-chloro-1-ethyl-6-nitroquinolin-2(1H)-one, 4.26 g of cyclopropylboric acid monohydrate, 10.9 g of sodium carbonate, 0.44 g of bis(di-tert-butyl(4-dimethylaminophenyl)phosphine)dichloropalladium(II), 50 mL of ethylene glycol dimethyl ether, and 5.0 mL of water was heated at reflux under nitrogen atmosphere for 3 hours. The reaction mixture was cooled to room temperature, and then ethyl acetate and water were added. The organic layer was fractionated, washed successively with water and saturated sodium chloride aqueous solution, and then dried over anhydrous magnesium sulfate, and the solvent was distilled off under reduced pressure. To the obtained residue were added diisopropyl ether, ethyl acetate, and hexane, and the solid matter was filtered and washed with diisopropyl ether to obtain 4.81 g of 4-cyclopropyl-1-ethyl-6-nitroquinolin-2(1H)-one as a slightly brown solid.

$^1$H-NMR (CDCl$_3$) δ: 0.79-0.87 (2H, m), 1.15-1.24 (2H, m), 1.37 (3H, t, J=7.3 Hz), 2.11-2.23 (1H, m), 4.37 (2H, q, J=7.1 Hz), 6.54 (1H, s), 7.47 (1H, d, J=9.2 Hz), 8.42 (1H, dd, J=9.2, 2.6 Hz), 9.00 (1H, d, J=2.6 Hz).

REFERENCE EXAMPLE 3

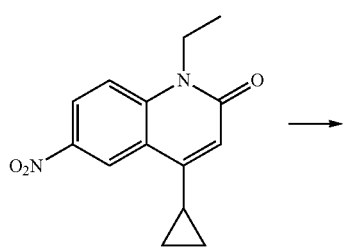

A mixture of 4.8 g of 4-cyclopropyl-1-ethyl-6-nitroquinolin-2(1H)-one, 0.68 g of ammonium chloride, 3.91 g of iron powder, 48 mL of ethanol, and 9.6 mL of water was heated at reflux for 1 hour. The reaction mixture was cooled to room temperature, and then water and ethyl acetate were added, and the insoluble matter was filtered off. The filter residue was washed with ethyl acetate and water. The filtrate was combined with the wash solution, and the organic layer was fractionated, washed with water and saturated sodium chloride aqueous solution, then dried over anhydrous magnesium sulfate, and the solvent was distilled off under reduced pressure. To the obtained residue were added diisopropyl ether and ethyl acetate, and the solid matter was filtered to obtain 3.92 g of 6-amino-4-cyclopropyl-1-ethylquinolin-2(1H)-one as a light yellow solid.

$^1$H-NMR (CDCl$_3$) δ: 0.71-0.79 (2H, m), 0.99-1.08 (2H, m), 1.33 (3H, t, J=7.3 Hz), 1.96-2.08 (1H, m), 3.74 (2H, brs), 4.31 (2H, q, J=7.1 Hz), 6.42 (1H, s), 6.99 (1H, dd, J=9.2, 2.6 Hz), 7.23 (1H, d, J=9.2 Hz), 7.38 (1H, d, J=2.6 Hz).

REFERENCE EXAMPLE 4

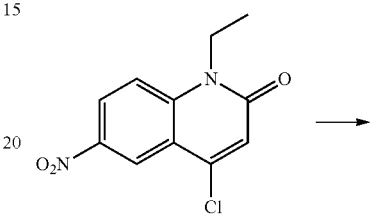

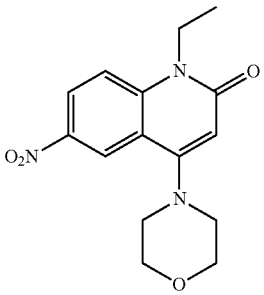

A mixture of 2.0 g of 4-chloro-1-ethyl-6-nitroquinolin-2(1H)-one, 10 mL of N,N-dimethylacetamide and 3.46 mL of morpholine was stirred at the ambient temperature of 130-140° C. for 2 hours. The reaction mixture was cooled to room temperature and the solvent was distilled off under reduced pressure. To the obtained residue was added water, and the solid matter was filtered and washed with diisopropyl ether to obtain 2.29 g of 1-ethyl-4-(morpholin-4-yl)-6-nitroquinolin-2(1H)-one as a slightly brown solid.

$^1$H-NMR (CDCl$_3$) δ: 1.37 (3H, t, J=7.3 Hz), 3.10-3.18 (4H, m), 3.95-4.03 (4H, m), 4.36 (2H, q, J=7.0 Hz), 6.27 (1H, s), 7.46 (1H, d, J=9.2 Hz), 8.38 (1H, dd, J=9.2, 2.6 Hz), 8.71 (1H, d, J=2.6 Hz).

REFERENCE EXAMPLE 5

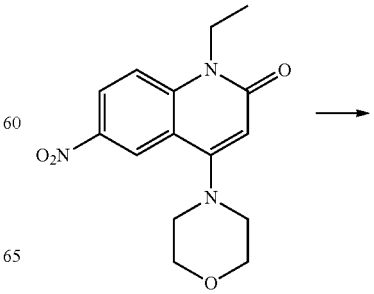

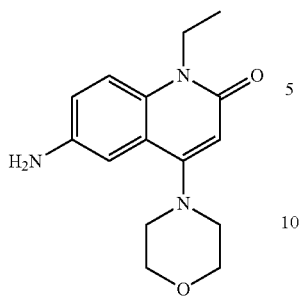

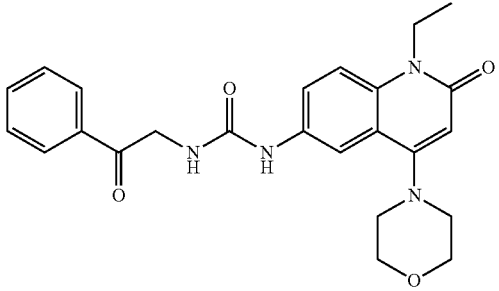

A mixture of 2.27 g of 1-ethyl-4-(morpholin-4-yl)-6-nitroquinolin-2(1H)-one, 0.26 g of ammonium chloride, 1.46 g of iron powder, 20 mL of ethanol and 4.0 mL of water was heated at reflux for 3 hours and 20 minutes. To the reaction mixture were added 20 mL of dioxane and 20 mL of ethyl acetate, and the mixture was heated at reflux for 3 hours. The reaction mixture was cooled to room temperature, allowed to stand overnight, and then heated at reflux for 1 hour. To the reaction mixture was added 100 mL of chloroform, and the mixture was heated at reflux for 1 hour. To the reaction mixture were added 0.26 g of ammonium chloride and 0.73 g of iron powder, and the mixture was heated at reflux for 5 hours. The reaction mixture was cooled to room temperature and the insoluble matter was filtered off. The filter residue was washed with chloroform and water. The filtrate was combined with the wash solution, and then the organic layer was fractionated, washed with saturated sodium chloride aqueous solution, then dried over anhydrous magnesium sulfate, and the solvent was distilled off under reduced pressure. To the obtained residue was added diisopropyl ether, and the solid matter was filtered to obtain 1.76 g of 6-amino-1-ethyl-4-(morpholin-4-yl)quinolin-2(1H)-one as slightly brown solid.

$^1$H-NMR (CDCl$_3$) δ: 1.32 (3H, t, J=7.3 Hz), 3.04-3.12 (4H, m), 3.71 (2H, brs), 3.89-3.96 (4H, m), 4.29 (2H, q, J=7.0 Hz), 6.18 (1H, s), 6.96 (1H, dd, J=8.6, 2.6 Hz), 7.09 (1H, d, J=3.3 Hz), 7.24 (1H, d, J=9.2 Hz).

REFERENCE EXAMPLE 6

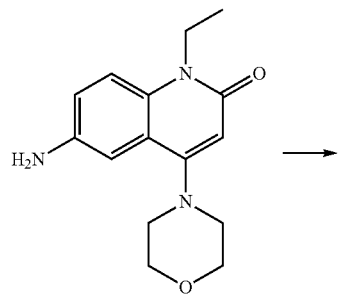

To a solution of 0.7 g of 6-amino-1-ethyl-4-(morpholin-4-yl)quinolin-2(1H)-one in 14 mL of dichloromethane was added 0.46 g of 1,1'-carbonyldiimidazole, and the mixture was stirred at room temperature for 4 hours. To the reaction mixture was added 0.54 mL of triethylamine. To the reaction mixture under ice cooling was added 0.48 g of 2-amino-1-phenylethanone hydrochloride, and the mixture was stirred at room temperature for 3 hours. To the reaction mixture were added chloroform and water, and the pH of the mixture was adjusted to 2.0 with 2 mol/L hydrochloric acid. The organic layer was fractionated, washed with saturated sodium chloride aqueous solution, and then dried over anhydrous magnesium sulfate, and the solvent was distilled off under reduced pressure. To the obtained residue were added diisopropyl ether and ethyl acetate, and the solid matter was filtered to obtain 0.86 g of 1-(1-ethyl-4-(morpholin-4-yl)-2-oxo-1,2-dihydroquinolin-6-yl)-3-(2-oxo-2-phenylethyl)urea as a slightly brown solid.

$^1$H-NMR (CDCl$_3$) δ: 1.34 (3H, t, J=6.9 Hz), 3.10-3.17 (4H, m), 3.89-3.97 (4H, m), 4.32 (2H, q, J=7.0 Hz), 4.86 (2H, d, J=4.0 Hz), 5.93-6.01 (1H, m), 6.22 (1H, s), 6.98 (1H, s), 7.34 (1H, d, J=9.2 Hz), 7.42-7.56 (3H, m), 7.59-7.68 (1H, m), 7.96-8.03 (3H, m).

REFERENCE EXAMPLE 7

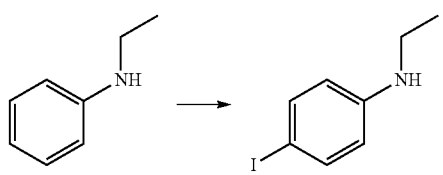

To a solution of 5 mL of N-ethylaniline in 50 mL of dichloromethane and 25 mL of methanol was added 6.7 g of sodium bicarbonate at room temperature, followed by the addition of 13.8 g of benzyltrimethylammonium dichloroiodate. After stirring the reaction mixture at room temperature for 30 minutes, ethyl acetate and water were added to the mixture. The organic layer was fractionated, washed successively with water and saturated sodium chloride aqueous solution, and then dried over anhydrous magnesium sulfate, and the solvent was distilled off under reduced pressure to obtain 9.8 g of N-ethyl-4-iodoaniline as a slightly brown solid.

$^1$H-NMR (CDCl$_3$) δ: 1.24 (3H, t, J=6.9 Hz), 3.12 (2H, q, J=7.0 Hz), 3.60 (1H brs), 6.34-6.42 (2H, m), 7.37-7.45 (2H, m).

REFERENCE EXAMPLE 8

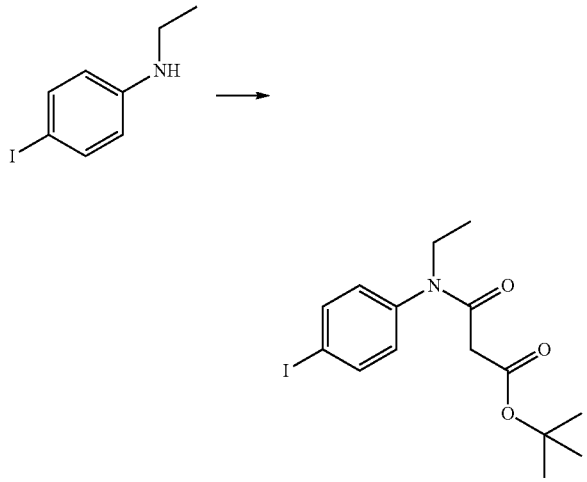

To a mixture of 9.8 g of N-ethyl-4-iodoaniline, 7.0 g of 3-tert-butoxy-3-oxopropionic acid and 50 mL of dichloromethane was added 8.38 g of 1-ethyl-3-(3-dimethylaminopropyl)carbodiimide hydrochloride under ice cooling, and the obtained mixture was stirred at room temperature for 2 hours. To the reaction mixture were added 6.1 mL of triethylamine and 5.34 g of N,N-dimethyl-4-aminopyridine, and the mixture was stirred at room temperature for 1 hour. To the reaction mixture were added 1.75 g of 3-tert-butoxy-3-oxopropionic acid and 4.2 g of 1-ethyl-3-(3-dimethylaminopropyl)carbodiimide hydrochloride, and the mixture was stirred at room temperature for 1 hour. To the reaction mixture were added water and ethyl acetate. The organic layer was fractionated, washed twice with saturated sodium hydrogen carbonate aqueous solution and 1 mol/L hydrochloric acid, and then dried over anhydrous magnesium sulfate, and the solvent was distilled off under reduced pressure. To the obtained residue was added diisopropyl ether and ethyl acetate, and the solid matter was filtered and washed with diisopropyl ether to obtain 8.1 g of tert-butyl 3-(ethyl-(4-iodophenyl)amino)-3-oxopropanoate as a white solid.

$^1$H-NMR (CDCl$_3$) δ: 1.12 (3H, t, J=7.3 Hz), 1.42 (9H, s), 3.07 (2H, s), 3.75 (2H, q, J=7.0 Hz), 6.94-7.01 (2H, m), 7.71-7.79 (2H, m).

REFERENCE EXAMPLE 9

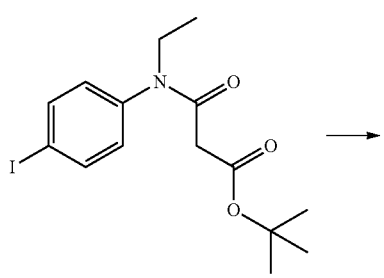

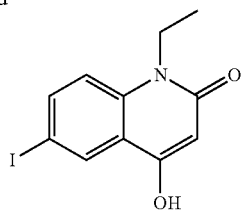

To 40 mL of methanesulfonic acid was added 8.1 g of tert-butyl 3-(ethyl (4-iodophenyl)amino)-3-oxopropanoate at room temperature. To the obtained mixture was added 5.91 g of diphosphorus pentaoxide, and then the mixture was stirred at the ambient temperature of 50-60° C. for 30 minutes. The reaction mixture was warmed and stirred at the ambient temperature of 100-110° C. for 30 minutes. The reaction mixture was cooled to room temperature, and then the mixture was put into iced water. The solid matter was filtered and washed with water to obtain 6.55 g of 1-ethyl-4-hydroxy-6-iodoquinolin-2(1H)-one as a slightly brown solid.

$^1$H-NMR (DMSO-D$_6$) δ: 1.14 (3H, t, J=7.3 Hz), 4.17 (2H, q, J=7.0 Hz), 5.86 (1H, s), 7.36 (1H, d, J=9.2 Hz), 7.88 (1H, dd, J=8.6, 2.0 Hz), 8.14 (1H, d, J=2.0 Hz), 11.56 (1H, brs).

REFERENCE EXAMPLE 10

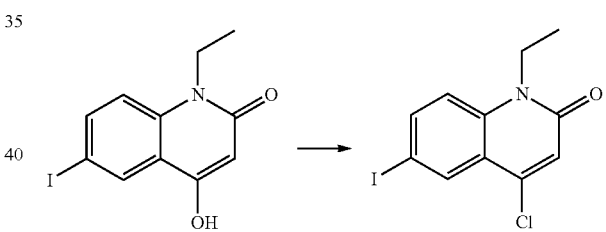

To 25 mL of phosphorous oxychloride was added 6.5 g of 1-ethyl-4-hydroxy-6-iodoquinolin-2(1H)-one at room temperature, and the mixture was stirred at the ambient temperature of 90-100° C. for 30 minutes. The reaction mixture was cooled to room temperature, and then the mixture was put into water. To the obtained mixture was added ethyl acetate, the organic layer was fractionated, washed with saturated sodium chloride aqueous solution, and then dried over anhydrous magnesium sulfate, and the solvent was distilled off under reduced pressure. The obtained residue was purified by silica gel column chromatography [ethyl acetate]. To the obtained residue were added diisopropyl ether, ethyl acetate, and hexane, and the solid matter was filtered to obtain 4.87 g of 4-chloro-1-ethyl-6-iodoquinolin-2(1H)-one as a slightly brown solid.

$^1$H-NMR (DMSO-D$_6$) δ: 1.19 (3H, t, J=7.3 Hz), 4.25 (2H, q, J=7.0 Hz), 6.98 (1H, s), 7.52 (1H, d, J=9.2 Hz), 8.01 (1H, dd, J=9.2, 2.0 Hz), 8.19 (1H, d, J=2.0 Hz).

REFERENCE EXAMPLE 11

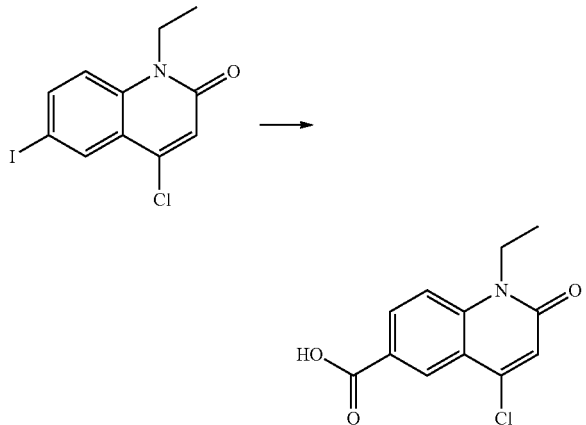

A mixture of 1.48 g of 4-chloro-1-ethyl-6-iodoquinolin-2(1H)-one, 0.9 g of sodium formate, 0.56 g of lithium chloride, 1.51 mL of N,N-diisopropylethylamine, 0.86 mL of acetic anhydride, 0.12 g of tris(dibenzylideneacetone)dipalladium (0), and 10 mL of N,N-dimethylacetamide was stirred under nitrogen atmosphere at the ambient temperature of 90° C. for 4 hours. The reaction mixture was cooled to room temperature and the insoluble matter was filtered off. The filter residue was washed with 5 mol; sodium hydroxide aqueous solution and water. After combining the filtrate with the wash solution and adjusting the pH to 2.0 with 6 mol/L hydrochloric acid, diisopropyl ether and ethyl acetate were added to the mixture. The solid matter was filtered and washed with diisopropyl ether to obtain 1.06 g of 4-chloro-1-ethyl-2-oxo-1,2-dihydroquinoline-6-carboxylic acid as a slightly brown solid.

$^1$H-NMR (DMSO-D$_6$) δ: 1.23 (3H, t, J=7.3 Hz), 4.31 (2H, q, J=7.0 Hz), 7.06 (1H, s), 7.80 (1H, d, J=9.2 Hz), 8.22 (1H, dd, J=8.6, 2.0 Hz), 8.51 (1H, d, J=2.0 Hz), 13.27 (1H, brs).

REFERENCE EXAMPLE 12

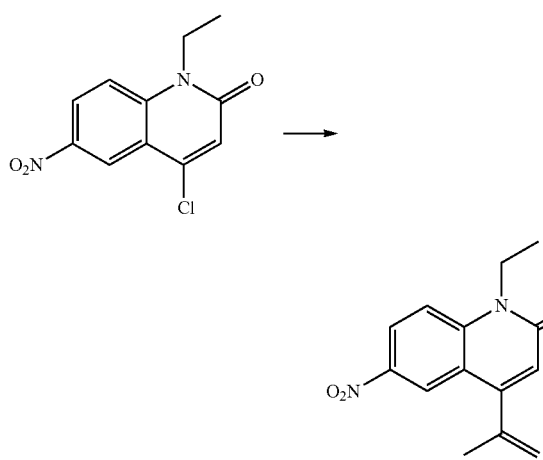

A mixture of 10.1 g of 4-chloro-1-ethyl-6-nitroquinolin-2(1H)-one, 8.07 g of isopropenylboronic acid pinacol ester, 17.38 g of tripotassium phosphate, 0.28 g of bis(di-tert-butyl(4-dimethylaminophenyl)phosphine)dichloropalladium(II), 225 mL of dioxane and 90 mL of water was heated at reflux under nitrogen atmosphere for 3 hours and 10 minutes. To the reaction mixture was added 0.28 g of bis(di-tert-butyl(4-dimethylaminophenyl)phosphine)dichloropalladium(II), and the mixture was heated at reflux for 30 minutes. To the reaction mixture was added 0.28 g of bis(di-tert-butyl(4-dimethylaminophenyl)phosphine)dichloropalladium(II), and the mixture was heated at reflux for 1 hour and 30 minutes. The reaction mixture was cooled to room temperature, and then ethyl acetate and water were added. The organic layer was fractionated, and the aqueous layer was extracted twice with ethyl acetate. The organic layer was combined with the extract, washed with saturated sodium chloride aqueous solution, and then dried over anhydrous magnesium sulfate, and the solvent was distilled off under reduced pressure. To the obtained residue were added diisopropyl ether and ethyl acetate, and the solid matter was filtered to obtain 10.19 g of 1-ethyl-6-nitro-4-(prop-1-en-2-yl)quinolin-2(1H)-one as a yellow solid.

$^1$H-NMR (CDCl$_3$) δ: 1.40 (3H, t, J=7.2 Hz), 2.14-2.19 (3H, m), 4.40 (2H, q, J=7.2 Hz), 5.13-5.18 (1H, m), 5.49-5.53 (1H, m), 6.66 (1H, s), 7.48 (1H, d, J=9.3 Hz), 8.40 (1H, dd, J=9.3, 2.7 Hz), 8.64 (1H, d, J=2.7 Hz).

REFERENCE EXAMPLE 13

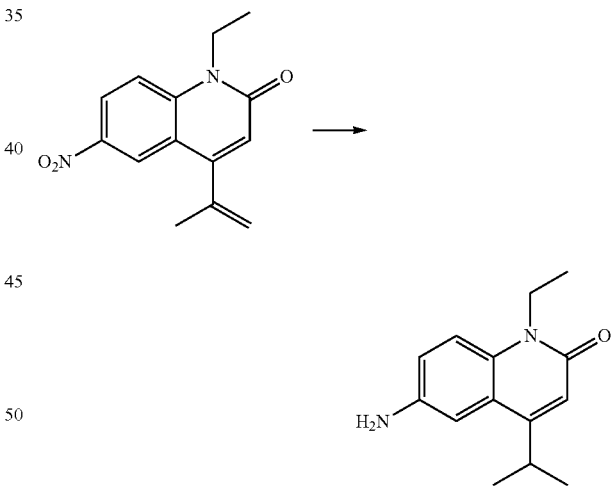

A solution of 5.0 g of 1-ethyl-6-nitro-4-(prop-1-en-2-yl)quinolin-2(1H)-one in 450 mL of methanol, and 50 mL of dioxane was added 2.5 g of 10% palladium-carbon. and the mixture was stirred at room temperature under hydrogen atmosphere for 2 hours. The insoluble matter was filtered off, and the solvent was distilled off under reduced pressure, to obtain 3.86 g of 6-amino-1-ethyl-4-(propan-2-yl)quinolin-2(1H)-one as a yellow foam.

$^1$H-NMR (CDCl$_3$) δ: 1.31 (6H, d, J=6.8 Hz), 1.27-1.38 (3H, m), 3.23-3.35 (1H, m), 4.32 (2H, q, J=7.2 Hz), 6.63 (1H, s), 6.98 (1H, dd, J=9.0, 2.4 Hz), 7.10 (1H, d, J=2.4 Hz), 7.23-7.30 (1H, m).

REFERENCE EXAMPLE 14

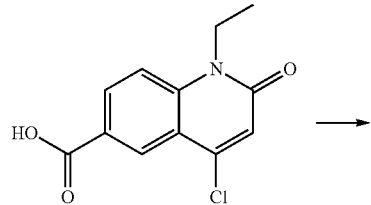

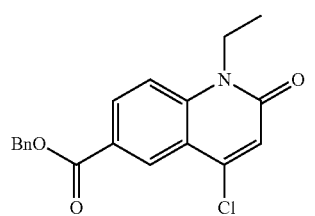

To a suspension of 1.01 g of 4-chloro-1-ethyl-2-oxo-1,2-dihydroquinoline-6-carboxylic acid in 5 mL of N,N-dimethylformamide were added 0.83 g of potassium carbonate and 0.51 mL of benzyl chloride, and the mixture was stirred at the ambient temperature of 80° C. for 1 hour. The reaction mixture was cooled to room temperature, and then ethyl acetate and water were added, and the pH of the mixture was adjusted to 2.0 with 6 mol/L hydrochloric acid. The organic layer was fractionated, and the aqueous layer was extracted with ethyl acetate. The organic layer was combined with the extract, washed successively with water and saturated sodium chloride aqueous solution, and then dried over anhydrous magnesium sulfate, and the solvent was distilled off under reduced pressure. The obtained residue was purified by silica gel column chromatography [hexane:ethyl acetate gradient elution=80:20 to 70:30]. To the obtained residue was added diisopropyl ether, and the solid matter was filtered to obtain 1.09 g of benzyl 4-chloro-1-ethyl-2-oxo-1,2-dihydroquinoline-6-carboxylate as a white solid.

$^1$H-NMR (CDCl$_3$) δ: 1.36 (3H, t, J=7.2 Hz), 4.36 (2H, q, J=7.2 Hz), 5.43 (2H, s), 6.93 (1H, s), 7.34-7.52 (6H, m), 8.30 (1H, dd, J=9.0, 2.0 Hz), 8.75 (1H, d, J=2.0 Hz).

REFERENCE EXAMPLE 15

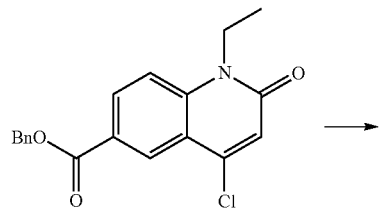

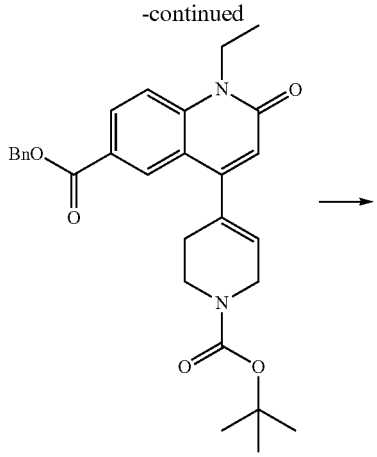

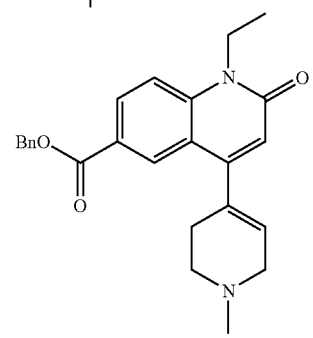

A mixture of 1.09 g of benzyl 4-chloro-1-ethyl-2-oxo-1,2-dihydroquinoline-6-carboxylate, 1.18 g of tert-butyl 4-(4,4,5,5-tetramethyl-1,3,2-dioxaborolan-2-yl)-3,6-dihydropyridine-1(2H)-carboxylate, 1.36 g of tripotassium phosphate, 68 mg of bis(di-tert-butyl(4-dimethylaminophenyl)phosphine)dichloropalladium(II), 23 mL of dioxane and 9 mL of water was heated at reflux under nitrogen atmosphere for 30 minutes. The reaction mixture was cooled to room temperature, and then ethyl acetate and water were added. The organic layer was fractionated, and the aqueous layer was extracted twice with ethyl acetate. The organic layer was combined with the extract, washed with saturated sodium chloride aqueous solution, and then dried over anhydrous magnesium sulfate, and the solvent was distilled off under reduced pressure. The obtained residue was purified by silica gel column chromatography [hexane:ethyl acetate gradient elution=70:30 to 60:40] to obtain benzyl 4-(1-(tert-butoxycarbonyl)-1,2,3,6-tetrahydropyridin-4-yl)-1-ethyl-2-oxo-1,2-dihydroquinoline-6-carboxylate as a yellow oil.

To a solution of the obtained benzyl 4-(1-(tert-butoxycarbonyl)-1,2,3,6-tetrahydropyridin-4-yl)-1-ethyl-2-oxo-1,2-dihydroquinoline-6-carboxylate in 4 mL of formic acid was added 2.5 mL of 37% formaldehyde aqueous solution, and the mixture was stirred at the ambient temperature of 80° C. for 1 hour and 30 minutes. To sodium hydrogen carbonate aqueous solution were added the reaction mixture and ethyl acetate. The organic layer was fractionated, and the aqueous layer was extracted twice with ethyl acetate. The organic layer was combined with the extract, washed with saturated sodium chloride aqueous solution, and then dried over anhydrous sodium sulfate, and the solvent was distilled off under reduced pressure. The obtained residue was purified by silica gel column chromatography [chloroform:methanol gradient elution=100:0 to 70:30] to obtain 1.17 g of benzyl 1-ethyl-4-(1-methyl-1,2,3,6-tetrahydropyridin-4-yl)-2-oxo-1,2-dihydroquinoline-6-carboxylate as a light brown solid.

$^1$H-NMR (CDCl$_3$) δ: 1.37 (3H, t, J=7.2 Hz), 2.45 (3H, s), 2.42-2.53 (2H, m), 2.71 (2H, t, J=5.6 Hz), 3.13-3.21 (2H, m), 4.37 (2H, q, J=7.2 Hz), 5.39 (2H, s), 5.80-5.87 (1H, m), 6.58 (1H, s), 7.33-7.50 (6H, m), 8.21 (1H, dd, J=9.0, 2.0 Hz), 8.45 (1H, d, J=2.0 Hz).

REFERENCE EXAMPLE 16

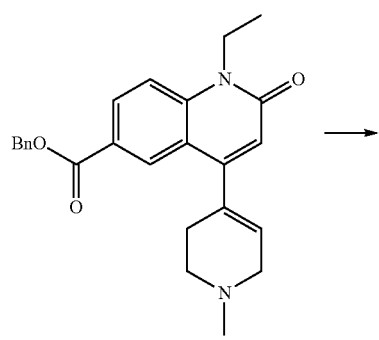

To a solution of 118 mg of benzyl 1-ethyl-4-(1-methyl-1,2,3,6-tetrahydropyridin-4-yl)-2-oxo-1,2-dihydroquinoline-6-carboxylate in 20 mL of methanol was added 118 mg of 10% palladium-carbon, and the mixture was stirred under hydrogen atmosphere at room temperature for 3 hours and 15 minutes. The insoluble matter was filtered off, and the solvent was distilled off under reduced pressure. To the obtained residue was added ethyl acetate, and the solid matter was filtered to obtain 62 mg of 1-ethyl-4-(1-methyl-piperidin-4-yl)-2-oxo-1,2-dihydroquinoline-6-carboxylic acid.

$^1$H-NMR (D$_2$O) δ: 1.12 (3H, t, J=7.3 Hz), 1.70-1.85 (2H, m), 2.01-2.12 (2H, m), 2.81 (3H, s), 3.13-3.23 (2H, m), 3.24-3.34 (1H, m), 3.48-3.57 (2H, m), 4.13 (2H, q, J=7.3 Hz), 6.41 (1H, s), 7.51 (1H, d, J=9.0 Hz), 7.98 (1H, d, J=9.0 Hz), 8.25 (1H, s).

REFERENCE EXAMPLE 17

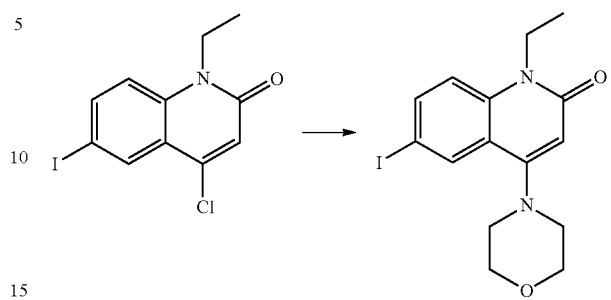

A mixture of 0.39 g of 4-chloro-1-ethyl-6-iodoquinolin-2(1H)-one, 2.0 mL of N,N-dimethylacetamide and 0.51 mL of morpholine was stirred in a sealed tube at the ambient temperature of 130-140° C. for 1 hour and 30 minutes. The reaction mixture was cooled to room temperature and then the solvent was distilled off under reduced pressure. To the obtained residue were added ethyl acetate and water, and the pH of the mixture was adjusted to 2.0 with 2 mol/L hydrochloric acid. The organic layer was fractionated, washed with saturated sodium chloride aqueous solution, and then dried over anhydrous magnesium sulfate, and the solvent was distilled off under reduced pressure. To the obtained residue were added diisopropyl ether and hexane, and the solid matter was filtered to obtain 0.33 g of 1-ethyl-6-iodo-4-(morpholin-4-yl)quinolin-2(1H)-one as slightly brown solid.

$^1$H-NMR (CDCl$_3$) δ: 1.32 (3H, t, J=7.3 Hz), 3.04-3.13 (4H, m), 3.90-3.99 (4H, m), 4.28 (2H, q, J=7.3 Hz), 6.18 (1H, s), 7.14 (1H, d, J=9.2 Hz), 7.79 (1H, dd, J=8.9, 2.3 Hz), 8.10 (1H, d, J=8.9 Hz).

REFERENCE EXAMPLE 18

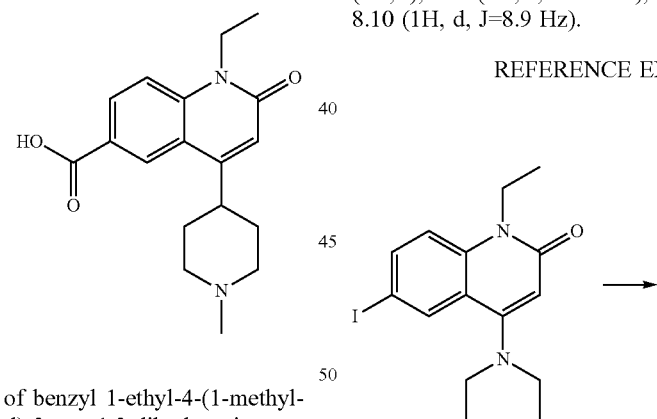

A mixture of 0.25 g of 1-ethyl-6-iodo-4-(morpholin-4-yl)quinolin-2(1H)-one, 53 mg of 1,1'-bis(diphenyl phosphino)

ferrocene palladium(II) dichloride, 0.19 g of potassium acetate, 0.17 g of bis(pinacolato)diboron, and 3.0 mL of dioxane was heated at reflux under nitrogen atmosphere for 4 hours. The reaction mixture was cooled to room temperature, and then ethyl acetate and water were added. The organic layer was fractionated, washed with saturated sodium chloride aqueous solution, and then dried over anhydrous magnesium sulfate, and the solvent was distilled off under reduced pressure. The obtained residue was purified by silica gel column chromatography [hexane:ethyl acetate gradient elution=80:20 to 0:100] to obtain 66 mg of 1-ethyl-4-(morpholin-4-yl)-6-(4,4,5,5-tetramethyl-1,3,2-dioxaborolan-2-yl)quinolin-2(1H)-one as a slightly brown oil.

$^1$H-NMR (CDCl$_3$) δ: 1.20-1.45 (15H, m), 3.05-3.22 (4H, m), 3.90-4.05 (4H, m), 4.25-4.41 (2H, m), 6.14-6.22 (1H, m), 7.33-7.43 (1H, m), 7.89-8.00 (1H, m), 8.23-8.33 (1H, m).

REFERENCE EXAMPLE 19

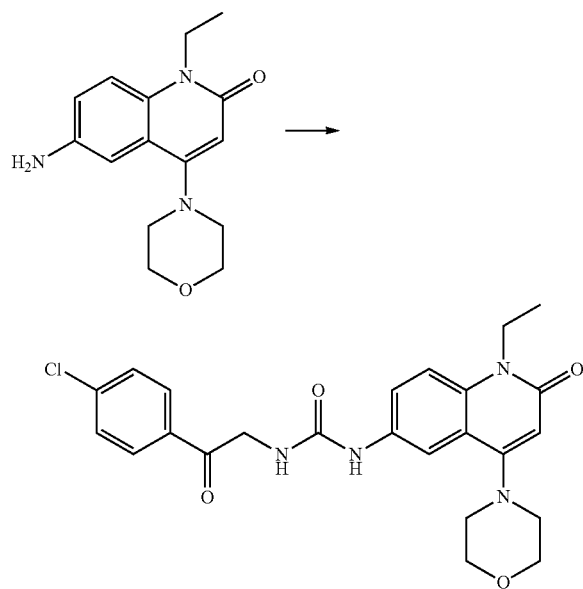

To a solution of 1.0 g of 6-amino-1-ethyl-4-(morpholin-4-yl)quinolin-2(1H)-one in 10 mL of dichloromethane was added 0.65 g of 1,1'-carbonyldiimidazole, and the mixture was stirred at the ambient temperature of 40-50° C. for 2 hours. To the reaction mixture under ice cooling were added 0.76 mL of triethylamine and 0.84 g of 2-amino-1-(4-chlorophenyl)ethanone hydrochloride, and the mixture was stirred at room temperature for 2 hours. To the reaction mixture were added chloroform and water, and the pH of the mixture was adjusted to 2.0 with 2 mol/L hydrochloric acid. The organic layer was fractionated, washed with water and saturated sodium chloride aqueous solution, and then dried over anhydrous magnesium sulfate, and the solvent was distilled off under reduced pressure. The obtained residue was purified by silica gel column chromatography [chloroform:methanol gradient elution=100:0 to 90:10]. To the obtained residue were added diisopropyl ether and ethyl acetate, and the solid matter was filtered to obtain 0.74 g of 1-(2-(4-chlorophenyl)-2-oxoethyl)-3-(1-ethyl-4-(morpholin-4-yl)-2-oxo-1,2-dihydroquinolin-6-yl)urea as a slightly brown solid.

$^1$H-NMR (DMSO-D$_6$) δ: 1.17 (3H, t, J=7.0 Hz), 3.01-3.08 (4H, m), 3.79-3.86 (4H, m), 4.20 (2H, q, J=7.1 Hz), 4.70 (2H, d, J=5.1 Hz), 5.99 (1H, s), 6.50 (1H, t, J=5.2 Hz), 7.47 (1H, d, J=9.3 Hz), 7.56 (1H, dd, J=9.1, 2.6 Hz), 7.61-7.67 (2H, m), 8.01-8.07 (3H, m), 9.07 (1H, s).

REFERENCE EXAMPLE 20

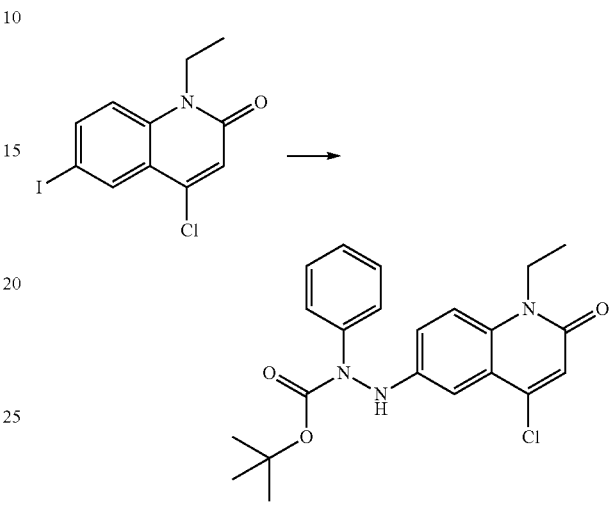

A mixture of 11.14 g of 4-chloro-1-ethyl-6-iodoquinolin-2(1H)-one, 7.93 g of tert-butyl 1-phenylhydrazinecarboxylate, 581 mg of tri-tert-butyl phosphonium tetrafluoroborate, 375 mg of palladium acetate, 16.32 g of cesium carbonate, and 160 mL of toluene was heated at reflux under nitrogen atmosphere for 1 hour and 30 minutes. The reaction mixture was cooled to room temperature, and then water was added. The organic layer was fractionated, and the aqueous layer was extracted with ethyl acetate. The organic layer was combined with the extract, washed with saturated sodium chloride aqueous solution, and then dried over anhydrous sodium sulfate, and the solvent was distilled off under reduced pressure. The obtained residue was purified by silica gel column chromatography [hexane:ethyl acetate gradient elution=80:20 to 60:40] to obtain 6.01 g of tert-butyl 2-(4-chloro-1-ethyl-2-oxo-1,2-dihydroquinolin-6-yl)-1-phenylhydrazinecarboxylate as a yellow solid.

$^1$H-NMR (CDCl$_3$) δ: 1.33 (3H, t, J=7.2 Hz), 1.43 (9H, s), 4.31 (2H, q, J=7.1 Hz), 6.58 (1H, s), 6.87 (1H, s), 7.13-7.20 (2H, m), 7.29-7.39 (3H, m), 7.45 (1H, d, J=2.7 Hz), 7.54-7.60 (2H, m).

REFERENCE EXAMPLE 21

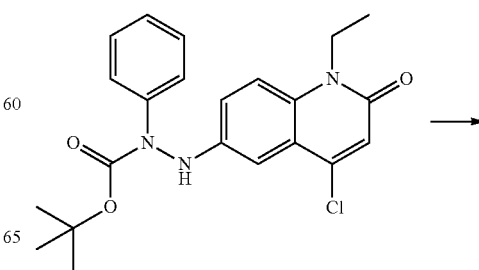

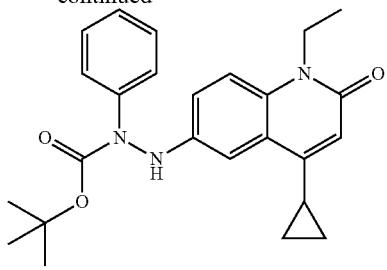

A mixture of 690 mg of tert-butyl 2-(4-chloro-1-ethyl-2-oxo-1,2-dihydroquinolin-6-yl)-1-phenylhydrazinecarboxylate, 172 mg of cyclopropylboric acid, 1.06 g of tripotassium phosphate, 35 mg of bis(di-tert-butyl(4-dimethylaminophenyl)phosphine)dichloropalladium(II), 12 mL of dioxane and 4.0 mL of water was stirred at 140° C. for 5 minutes using microwave equipment. The reaction mixture was cooled to room temperature, and then ethyl acetate and water were added. The organic layer was fractionated, and the aqueous layer was extracted with ethyl acetate. The organic layer was combined with the extract, washed with saturated sodium chloride aqueous solution, and then dried over anhydrous magnesium sulfate, and the solvent was distilled off under reduced pressure. The obtained residue was purified by silica gel column chromatography [hexane:ethyl acetate gradient elution=60:40 to 40:60] to obtain 527 mg of tert-butyl 2-(4-cyclopropyl-1-ethyl-2-oxo-1,2-dihydroquinolin-6-yl)-1-phenylhydrazinecarboxylate as a light yellow solid.

$^1$H-NMR (CDCl$_3$) δ: 0.67-0.73 (2H, m), 0.94-1.01 (2H, m), 1.32 (3H, t, J=7.1 Hz), 1.41 (9H, s), 1.90-2.00 (1H, m), 4.31 (2H, q, J=7.2 Hz), 6.44 (1H, d, J=0.98 Hz), 6.56 (1H, s), 7.08-7.19 (2H, m), 7.25-7.39 (3H, m), 7.52 (1H, d, J=2.4 Hz), 7.57-7.63 (2H, m).

REFERENCE EXAMPLE 22

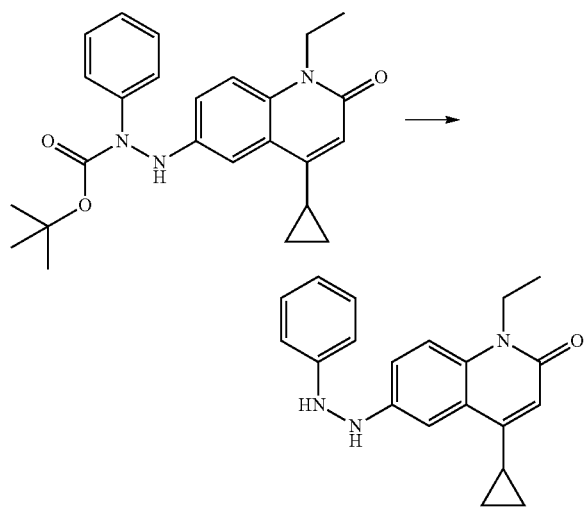

A mixture of 200 mg of tert-butyl 2-(4-cyclopropyl-1-ethyl-2-oxo-1,2-dihydroquinolin-6-yl-1-phenylhydrazinecarboxylate and 2 mL of 20% sodium ethoxide-ethanol solution was stirred at 140° C. for 2 minutes using microwave equipment. The reaction mixture was cooled to room temperature, and then ethyl acetate and water were added. The organic layer was fractionated, washed successively with water and saturated sodium chloride aqueous solution, and then dried over anhydrous magnesium sulfate, and the solvent was distilled off under reduced pressure. To the obtained residue was added diisopropyl ether, and the solid matter was filtered and washed with diisopropyl ether to obtain 115 mg of 4-cyclopropyl-1-ethyl-6-(2-phenylhydrazinyl)quinolin-2(1H)-one as a light yellow solid.

$^1$H-NMR (DMSO-D$_6$) δ: 0.62-0.69 (2H, m), 0.87-0.95 (2H, m), 1.15 (3H, t, J=7.0 Hz), 1.90-2.00 (1H, m), 4.18 (2H, q, J=7.0 Hz), 6.20 (1H, s), 6.65 (1H, t, J=7.2 Hz), 6.74-6.81 (2H, m), 7.08-7.15 (3H, m), 7.41 (1H, d J=9.3 Hz), 7.45 (1H, d, J=2.4 Hz), 7.69-7.77 (2H, m).

REFERENCE EXAMPLE 23

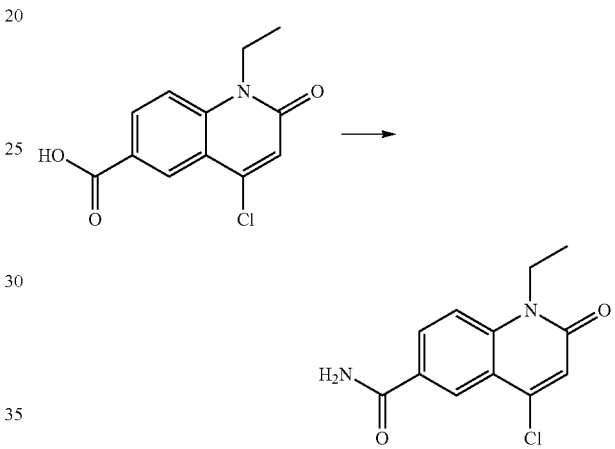

To a suspension of 4.0 g of 4-chloro-1-ethyl-2-oxo-1,2-dihydroquinoline-6-carboxylic acid in 25 mL of tetrahydrofuran at room temperature were added 2.6 mL of oxalyl chloride and 10 μL of N,N-dimethylformamide, and the mixture was stirred for 3 hours. To a 28% ammonium aqueous solution under ice cooling were added the reaction mixture and 100 mL of water. The solid matter was filtered and washed with water to obtain 3.70 g of 4-chloro-1-ethyl-2-oxo-1,2-dihydroquinoline-6-carboxamide as a slightly brown solid.

$^1$H-NMR (DMSO-D$_6$) δ: 1.22 (3H, t, J=7.1 Hz), 4.31 (2H, q, J=7.2 Hz), 7.02 (1H, s), 7.52 (1H, brs), 7.76 (1H, d, J=9.0 Hz), 8.22 (1H, dd, J=8.9, 2.1 Hz), 8.25 (1H, brs), 8.50 (1H, d, J=2.2 Hz).

REFERENCE EXAMPLE 24

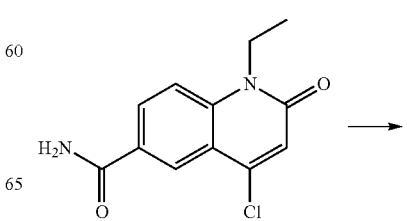

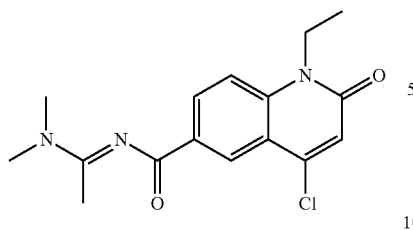

A mixture of 4-chloro-1-ethyl-2-oxo-1,2-dihydroquinoline-6-carboxamide and 10 mL of 1,1-dimethoxy-N,N-dimethylethaneamine was heated at reflux for 4 hours. After cooling the reaction mixture to room temperature, diisopropyl ether was added to the reaction mixture, the solid matter was filtered and washed with diisopropyl ether to obtain 2.13 g of 4-chloro-N-((1E)-1-(dimethylamino)ethylidene)-1-ethyl-2-oxo-1,2-dihydroquinoline-6-carboxamide as a slightly brown solid.

$^1$H-NMR (DMSO-D$_6$) δ: 1.22 (3H, t, J=7.1 Hz), 2.31 (3H, s), 3.16 (3H, s), 3.19 (3H, s), 4.30 (2H, q, J=7.1 Hz), 7.00 (1H, s), 7.72 (1H, d, J=8.8 Hz), 8.33 (1H, dd, J=8.8, 2.0 Hz), 8.64 (1H, d, J=2.0 Hz).

REFERENCE EXAMPLE 25

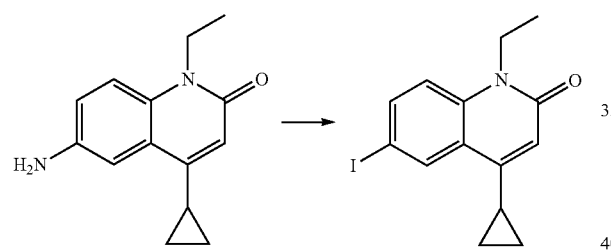

To a solution of 0.50 g of 6-amino-4-cyclopropyl-1-ethylquinolin-2(1H)-one in 9 mL of acetonitrile was added 1.25 g of p-toluenesulfonic acid monohydrate followed by the addition of 1.3 mL of aqueous solution of 0.91 g of potassium iodide and 0.30 g of sodium nitrite under ice cooling. The mixture was stirred for 10 minutes, and then stirred at room temperature for 1 hour. To the reaction mixture were added water, saturated sodium carbonate aqueous solution, 1% sodium thiosulfate aqueous solution, and ethyl acetate. The organic layer was fractionated, and the aqueous layer was extracted with ethyl acetate. The organic layer was combined with the extract, washed with saturated sodium chloride aqueous solution, and then dried over anhydrous sodium sulfate, and the solvent was distilled off under reduced pressure. The obtained residue was purified by silica gel column chromatography [hexane:ethyl acetate gradient elution=70:30 to 40:60]. To the obtained residue was added diisopropyl ether, and the solid matter was filtered to obtain 0.31 g of 4-cyclopropyl-1-ethyl-6-iodoquinolin-2(1H)-one as a light yellow solid.

$^1$H-NMR (CDCl$_3$) δ: 0.75-0.79 (2H, m), 1.07-1.12 (2H, m), 1.32 (3H, t, J=7.2 Hz), 2.01-2.08 (1H, m), 4.30 (2H, q, J=7.2 Hz), 6.43 (1H, d, J=1.2 Hz), 7.14 (1H, d, J=8.8 Hz), 7.81 (1H, dd, J=8.8, 2.0 Hz), 8.38 (1H, d, J=2.0 Hz).

REFERENCE EXAMPLE 26

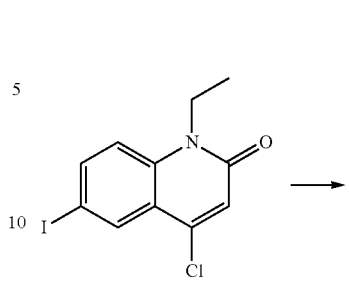

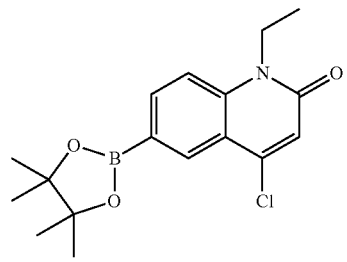

By the same method as Reference Example 18, from 4-chloro-1-ethyl-6-iodoquinolin-2(1H)-one was obtained 4-chloro-1-ethyl-6-(4,4,5,5-tetramethyl-1,3,2-dioxaborolan-2-yl)quinolin-2(1H)-one.

$^1$H-NMR (CDCl$_3$) δ: 1.35 (3H, t, J=7.2 Hz), 1.38 (12H, s), 4.36 (2H, q, J=7.2 Hz), 6.88 (1H, s), 7.39 (1H d, J=8.5 Hz), 8.03 (1H, dd, J=8.5, 1.5 Hz), 8.46 (1H d, J=1.5 Hz).

REFERENCE EXAMPLE 27

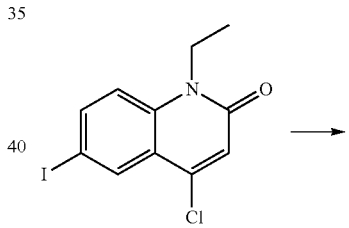

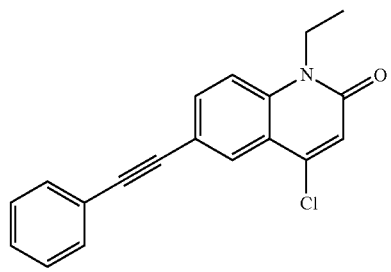

A mixture of 334 mg of 4-chloro-1-ethyl-6-iodoquinolin-2(1H)-one, 112 mg of ethynylbenzene, 2 mg of copper iodide(I), 5 mg of triphenylphosphine, 2 mg of dichloropalladium, 0.42 mL of triethylamine, and 5 mL of tetrahydrofuran was stirred under nitrogen atmosphere at room temperature for 2 hours. To the reaction mixture were added ethyl acetate, water and 1 mol/L hydrochloric acid. The organic layer was fractionated, and the aqueous layer was extracted with ethyl acetate. The organic layer was combined with the extract, washed with saturated sodium chloride aqueous solution, and then dried over anhydrous magnesium sulfate, and the solvent was distilled off under reduced pressure. To the obtained residue was added diisopropyl ether, and the solid matter was filtered to obtain 160 mg of 4-chloro-1-ethyl-6-(phenylethynyl)quinolin-2(1H)-one as a brown solid.

$^1$H-NMR (CDCl$_3$) δ: 1.37 (3H, t, J=7.2 Hz), 4.36 (2H, q, J=7.2 Hz), 6.92 (1H, s), 7.35-7.42 (4H, m), 7.55-7.60 (2H, m), 7.76 (1H, dd, J=8.8, 2.0 Hz), 8.20 (1H, d, J=2.0 Hz).

REFERENCE EXAMPLE 28

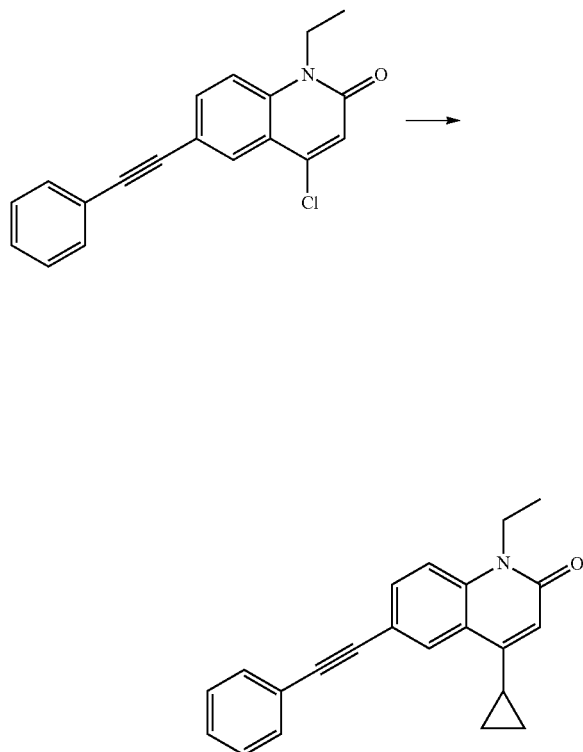

A mixture of 154 mg of 4-chloro-1-ethyl-6-(phenylethynyl)quinolin-2(1H)-one, 52 mg of cyclopropylboric acid, 318 mg of tripotassium phosphate, 11 mg of bis(di-tert-butyl (4-dimethylaminophenyl)phosphine)dichloropalladium(II), 3 mL of dioxane and 1 mL of water was stirred at 140° C. for 15 minutes using microwave equipment. The reaction mixture was cooled to room temperature, and then ethyl acetate, water and 2 mol/L hydrochloric acid were added. The organic layer was fractionated, and the aqueous layer was extracted with ethyl acetate. The organic layer was combined with the extract, washed with saturated sodium chloride aqueous solution, and then dried over anhydrous magnesium sulfate, and the solvent was distilled off under reduced pressure. The obtained residue was purified by silica gel chromatography [hexane:ethyl acetate gradient elution=80:20 to 60:40]. To the obtained residue was added diisopropyl ether, and the solid matter was filtered to obtain 100 mg of 4-cyclopropyl-1-ethyl-6-(phenylethynyl)quinolin-2(1H)-one as a white solid.

$^1$H-NMR (CDCl$_3$) δ: 0.77-0.83 (2H, m), 1.08-1.16 (2H, m), 1.36 (3H, t, J=7.1 Hz), 2.08-2.19 (1H, m), 4.35 (2H, q, J=7.2 Hz), 6.45-6.49 (1H, m), 7.34-7.42 (4H, m), 7.55-7.61 (2H, m), 7.71 (1H, dd, J=8.9, 1.8 Hz), 8.27 (1H, d, J=2.0 Hz).

REFERENCE EXAMPLE 29

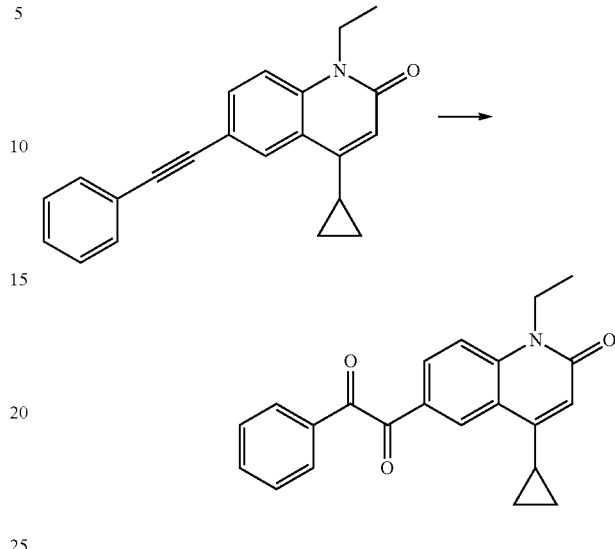

A mixture of 31 mg of 4-cyclopropyl-1-ethyl-6-(phenylethynyl)quinolin-2(1H)-one, 24 mg of magnesium sulfate, 19 mg of potassium permanganate, 5 mg of sodium hydrogen carbonate, 3 mL of acetone, and 1.7 mL of water was stirred at room temperature for 20 minutes. To the reaction mixture was added 43 mg of potassium permanganate, and the mixture was stirred at room temperature for 1 hour. To the reaction mixture were added 30 mg of sodium nitrite and 10% sulfuric acid aqueous solution, and then the insoluble matter was filtered off. The filter residue was washed with ethyl acetate and water. The filtrate was combined with the wash solution, and the organic layer was fractionated, and the aqueous layer was extracted with ethyl acetate. The organic layer was combined with the extract, washed with saturated sodium chloride aqueous solution, and then dried over anhydrous magnesium sulfate, and the solvent was distilled off under reduced pressure. The obtained residue was purified by silica gel chromatography [hexane:ethyl acetate gradient elution=60:40 to 30:70] to obtain 20 mg of 1-(4-cyclopropyl-1-ethyl-2-oxo-1,2-dihydroquinolin-6-yl)-2-phenylethane-1,2-dione.

$^1$H-NMR (CDCl$_3$) δ: 0.74-0.80 (2H, m), 1.05-1.12 (2H, m), 1.35 (3H, t, J=7.1 Hz), 2.07-2.16 (1H, m), 4.36 (2H, q, J=7.2 Hz), 6.46-6.49 (1H, m), 7.46 (1H, d, J=9.0 Hz), 7.54 (2H, t, J=7.9 Hz), 7.69 (1H, t, J=7.4 Hz), 8.02 (2H, dd, J=8.3, 1.2 Hz), 8.14 (1H, dd, J=8.9, 2.1 Hz), 8.77 (1H, d, J=2.0 Hz).

REFERENCE EXAMPLE 30

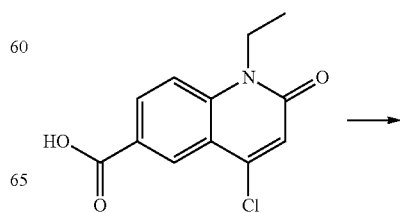

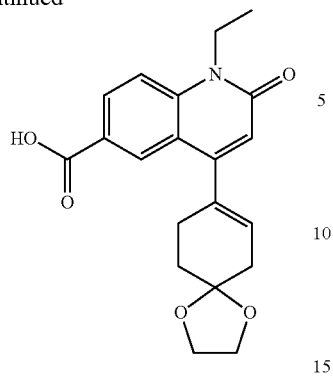

A mixture of 503 mg of 4-chloro-1-ethyl-2-oxo-1,2-dihydroquinoline-6-carboxylic acid, 639 mg of 8-(4,4,5,5-tetramethyl-1,3,2-dioxaborolan-2-yl)-(1,4-dioxaspiro[4.5]dec-7-ene, 849 mg of tripotassium phosphate, 42 mg of bis(di-tert-butyl(4-dimethylaminophenyl)phosphine)dichloropalladium(II), 12 mL of dioxane and 4 mL of water was stirred at 140° C. for 5 minutes using microwave equipment. The reaction mixture was cooled to room temperature, and then ethyl acetate and water were added to the reaction mixture. The aqueous layer was fractionated and washed twice with ethyl acetate. To the aqueous layer was added 6 mol/L hydrochloric acid to adjust the pH to 2.0, and then added tetrahydrofuran. The organic layer was fractionated, and the aqueous layer was extracted twice with ethyl acetate. The organic layer was combined with the extract, washed with saturated sodium chloride aqueous solution, and then dried over anhydrous magnesium sulfate, and the solvent was distilled off under reduced pressure. To the obtained residue was added ethyl acetate, and the solid matter was filtered to obtain 590 mg of 4-(1,4-dioxaspiro[4.5]dec-7-en-8-yl)-1-ethyl-2-oxo-1,2-dihydroquinoline-6-carboxylic acid as a light brown solid.

$^1$H-NMR (DMSO-D$_6$) δ: 1.21 (3H, t, J=7.0 Hz), 1.85 (2H, t, J=6.2 Hz), 2.39-2.56 (4H, m), 3.94-4.00 (4H, m), 4.29 (2H, q, J=7.1 Hz), 5.71-5.76 (1H, m), 6.41 (1H, s), 7.69 (1H, d, J=9.0 Hz), 8.11 (1H, dd, J=8.9, 2.1 Hz), 8.26 (1H, d, J=2.2 Hz), 13.02 (1H, brs).

REFERENCE EXAMPLE 31

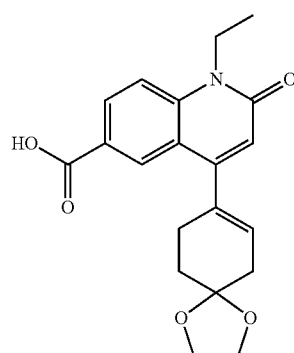 

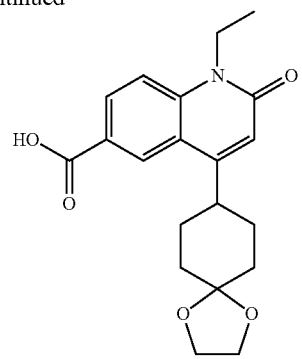

To a mixture of 583 mg of 4-(1,4-dioxaspiro[4.5]dec-7-en-8-yl)-1-ethyl-2-oxo-1,2-dihydroquinoline-6-carboxylic acid, 20 mL of dioxane and 100 mL of methanol was added 291 mg of 20% hydroxide palladium-carbon, and the mixture was stirred under hydrogen atmosphere at room temperature for 30 minutes. The insoluble matter was filtered off, and the solvent was distilled off under reduced pressure. To the obtained residue was added diisopropyl ether, the solid matter was filtered to obtain 502 mg of 4-(1,4-dioxaspiro[4.5]dec-8-yl)-1-ethyl-2-oxo-1,2-dihydroquinoline-6-carboxylic acid as a white solid.

$^1$H-NMR (DMSO-D$_6$) δ: 1.22 (3H, t, J=7.0 Hz), 1.60-1.93 (8H, m), 3.10-3.25 (1H, m), 3.87-3.96 (4H, m), 4.29 (2H, q, J=6.9 Hz), 6.46-6.51 (1H, m), 7.66-7.73 (1H, m), 8.13 (1H, dd, J=8.7 Hz, 1.6 Hz), 8.45 (1H d, J=1.5 Hz), 13.06 (1H, brs).

REFERENCE EXAMPLE 32

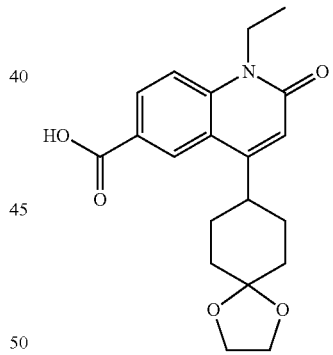 

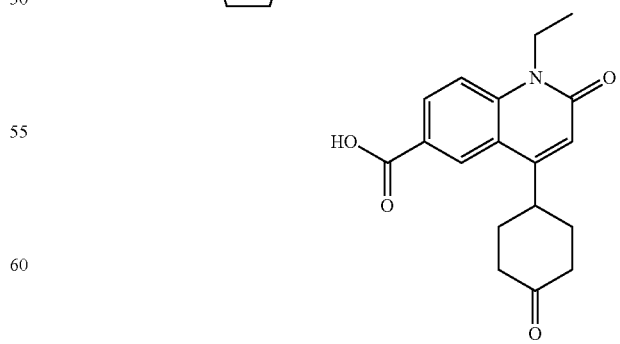

To a suspension of 250 mg of 4-(1,4-dioxaspiro[4.5]dec-8-yl)-1-ethyl-2-oxo-1,2-dihydroquinoline-6-carboxylic acid in 10 mL of tetrahydrofuran at room temperature was added 1.0 mL of concentrated hydrochloric acid, and the mixture was stirred for 4 hours. The solid matter was filtered and washed with ethyl acetate to obtain 182 mg of 1-ethyl-2-oxo-4-(4-oxocyclohexyl)-1,2-dihydroquinoline-6-carboxylic acid as a white solid.

$^1$H-NMR (DMSO-D$_6$) δ: 1.22 (3H, t, J=7.1 Hz), 1.83-2.00 (2H, m), 2.09-2.19 (2H, m), 2.26-2.37 (2H, m), 2.71-2.83 (2H, m), 3.67-3.77 (1H, m), 4.30 (2H, q, J=7.1 Hz), 6.58-6.62 (1H, m), 7.73 (1H, d, J=9.0 Hz), 8.16 (1H, dd, J=8.9 Hz, 1.8 Hz), 8.57 (1H, d, J=2.0 Hz).

EXAMPLE 1

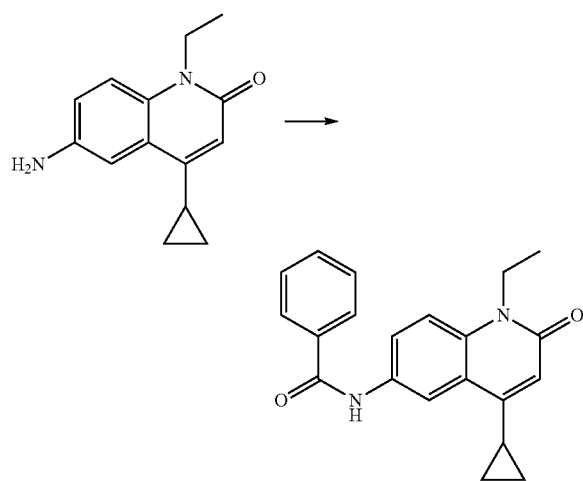

To a suspension of 1.2 g of 6-amino-4-cyclopropyl-1-ethylquinolin-2(1H)-one in 6 mL of pyridine was added 0.73 mL of benzoyl chloride, and the mixture was stirred at room temperature for 1 hour. To the reaction mixture were added ethyl acetate and water, and the pH of the mixture was adjusted to 2.0 with 2 mol/L hydrochloric acid. The organic layer was fractionated, washed with water and saturated sodium chloride aqueous solution, then dried over anhydrous magnesium sulfate, and the solvent was distilled off under reduced pressure. To the obtained residue were added diisopropyl ether and ethyl acetate, and the solid matter was filtered to obtain 1.75 g of N-(4-cyclopropyl-1-ethyl-2-oxo-1,2-dihydroquinolin-6-yl)benzamide as a slightly brown solid.

$^1$H-NMR (DMSO-D$_6$) δ: 0.75-0.84 (2H, m), 1.02-1.11 (2H, m), 1.20 (3H, t, J=6.9 Hz), 2.09-2.21 (1H, m), 4.26 (2H, q, J=7.1 Hz), 6.32 (1H, s), 7.44-7.66 (4H, m), 7.91-8.09 (3H, m), 8.65 (1H, d, J=2.0 Hz), 10.45 (1H, s).

EXAMPLE 2

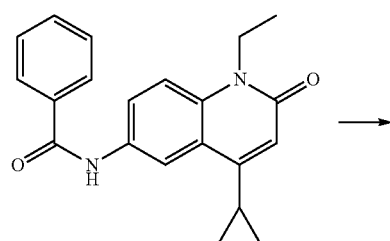

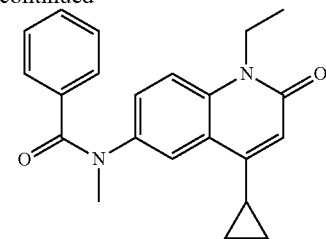

To a solution of 1.75 g of N-(4-cyclopropyl-1-ethyl-2-oxo-1,2-dihydroquinolin-6-yl)benzamide in 15 mL of N,N-dimethylacetamide, 0.25 g of 60% sodium hydride was added under ice cooling and the mixture was stirred for 10 minutes. To the reaction mixture under ice cooling was added 0.43 mL of methyl iodide, the mixture was stirred at room temperature for 1 hour. To the reaction mixture were added ethyl acetate and water, and the pH of the mixture was adjusted to 2.0 with 6 mol/L hydrochloric acid, and then the solid matter was filtered. The organic layer of the filtrate was fractionated, washed with water and saturated sodium chloride aqueous solution, then dried over anhydrous magnesium sulfate, and the solvent was distilled off under reduced pressure. To the obtained residue and filtered solid matter were added diisopropyl ether, ethyl acetate and water, and then the solid matter was filtered, washed with water and diisopropyl ether to obtain 1.45 g of N-(4-cyclopropyl-1-ethyl-2-oxo-1,2-dihydroquinolin-6-yl)-N-methylbenzamide as a slightly brown solid.

$^1$H-NMR (DMSO-D$_6$) δ: 0.48-0.57 (2H, m), 0.86-0.95 (2H, m), 1.13 (3H, t, J=6.9 Hz), 1.93-2.06 (1H, m), 3.44 (3H, s), 4.19 (2H, q, J=6.8 Hz), 6.24 (1H, s), 7.16-7.33 (5H, m), 7.46-7.58 (2H, m), 7.76-7.81 (1H, m).

EXAMPLE 3

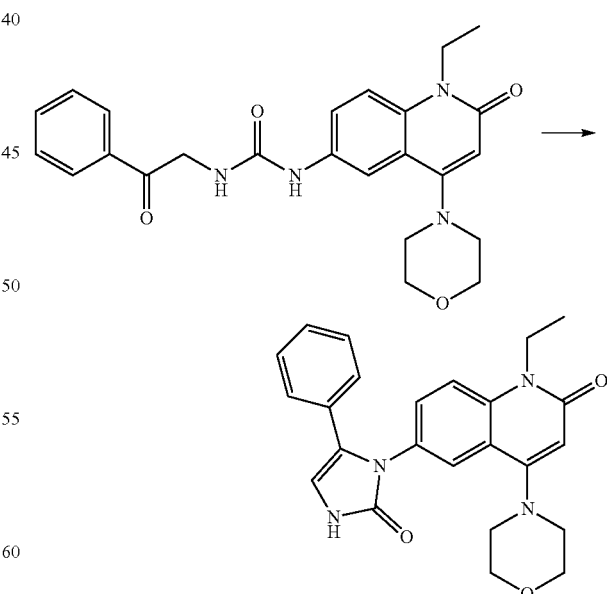

To a suspension of 0.86 g of 1-(1-ethyl-4-(morpholin-4-yl)-2-oxo-1,2-dihydroquinolin-6-yl)-3-(2-oxo-2-phenylethyl)urea in 5.0 mL of dioxane at room temperature was added 5.0 mL of concentrated hydrochloric acid and the mixture was stirred for 2 hours. To the reaction mixture was added water, and the solid matter was filtered and washed with water and diisopropyl ether to obtain 0.72 g of 1-ethyl-4-(morpholin-4-yl)-6-(2-oxo-5-phenyl-2,3-dihydro-1H-imidazol-1-yl)quinolin-2(1H)-one as a slightly brown solid.

¹H-NMR (DMSO-D₆) δ: 1.19 (3H, t, J=7.3 Hz), 2.54-2.65 (4H, m), 3.44-3.53 (4H, m), 4.17-4.29 (2H, m), 5.98 (1H, s), 6.87 (1H, d, J=2.6 Hz), 7.05-7.12 (2H, m), 7.14-7.31 (4H, m), 7.59-7.68 (2H, m). 10.57-10.63 (1H, m).

EXAMPLE 4

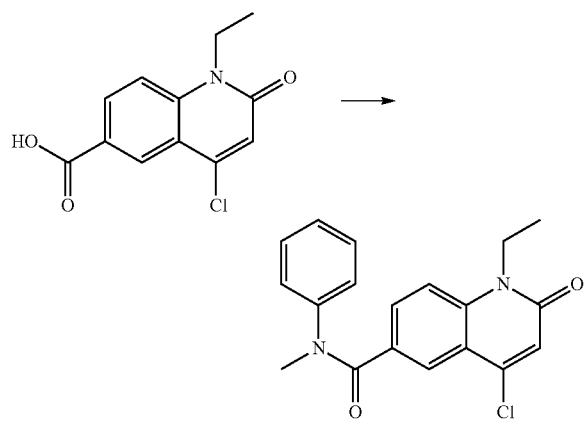

To a suspension of 3.0 g of 4-chloro-1-ethyl-2-oxo-1,2-dihydroquinoline-6-carboxylic acid in 30 mL of tetrahydrofuran at room temperature were added 1.25 mL of oxalyl chloride and 10 μL of N,N-dimethylformamide, and the mixture was stirred for 2 hours. To the reaction mixture under ice cooling were added 1.55 mL of N-methylaniline and 1.81 mL of triethylamine, and then the mixture was stirred at room temperature for 1 hour. To the reaction mixture were added ethyl acetate and water. The organic layer was fractionated, washed with water and saturated sodium chloride aqueous solution, and then dried over anhydrous magnesium sulfate, and the solvent was distilled off under reduced pressure. The obtained residue was purified by silica gel column chromatography [hexane:ethyl acetate gradient elution=50:50 to 20:80]. To the obtained residue were added diisopropyl ether and ethyl acetate, and then the solid matter was filtered to obtain 2.01 g of 4-chloro-1-ethyl-N-methyl-2-oxo-N-phenyl-1,2-dihydroquinoline-6-carboxamide as a slightly brown solid.

¹H-NMR (CDCl₃) δ: 1.28 (3H, t, J=6.9 Hz), 3.55 (3H, s), 4.26 (2H, q, J=7.3 Hz), 6.81 (1H, s), 7.07-7.13 (2H, m), 7.15-7.32 (4H, m), 7.65 (1H, dd, J=9.2, 2.0 Hz), 7.94 (1H, d, J=2.0 Hz).

EXAMPLE 5

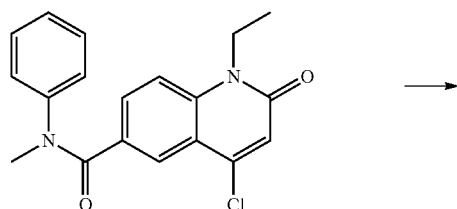

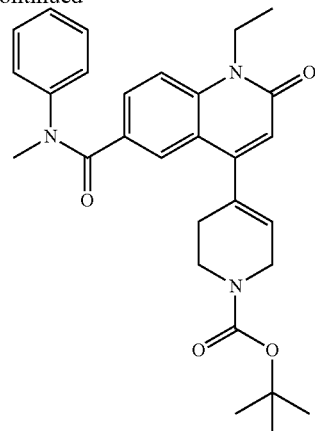

A mixture of 2.0 g of 4-chloro-1-ethyl-N-methyl-2-oxo-N-phenyl-1,2-dihydroquinoline-6-carboxamide, 2.18 g of tert-butyl 4-(4,4,5,5-tetramethyl-1,3,2-dioxaborolan-2-yl)-3,6-dihydropyridine-1(2H)-carboxylate, 1.24 g of sodium carbonate, 0.21 g of bis(di-tert-butyl(4-dimethylaminophenyl)phosphine)dichloropalladium(II), 20 mL of ethylene glycol dimethyl ether, and 4.0 mL of water was heated at reflux under nitrogen atmosphere for 3 hours. The reaction mixture was cooled to room temperature, and then ethyl acetate and water were added. The organic layer was fractionated, washed successively with water and saturated sodium chloride aqueous solution, and then dried over anhydrous magnesium sulfate, and the solvent was distilled off under reduced pressure. The obtained residue was purified by silica gel chromatography [hexane:ethyl acetate gradient elution=50:50 to 0:100] to obtain 2.9 g of tert-butyl 4-(1-ethyl-6-(methyl(phenyl)carbamoyl)-2-oxo-1,2-dihydroquinolin-4-yl)-3,6-dihydropyridine-1(2H)-carboxylate as a slightly brown foam.

¹H-NMR (CDCl₃) δ: 1.32 (3H, t, J=6.9 Hz), 1.56 (9H, s), 1.94-2.14 (2H, m), 3.53 (3H, s), 3.57 (2H, t, J=5.6 Hz), 3.99-4.06 (2H, m), 4.30 (2H, q, J=7.0 Hz), 5.42 (1H, brs), 6.41 (1H, s), 6.99-7.07 (2H, m), 7.10-7.19 (1H, m), 7.22-7.33 (3H, m), 7.35-7.41 (1H, m), 7.77 (1H, dd, J=9.2, 2.0 Hz).

EXAMPLE 6

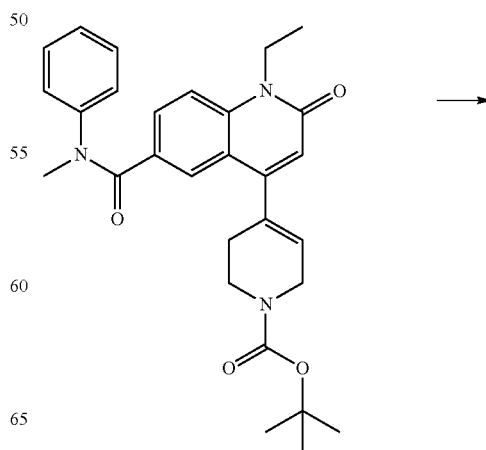

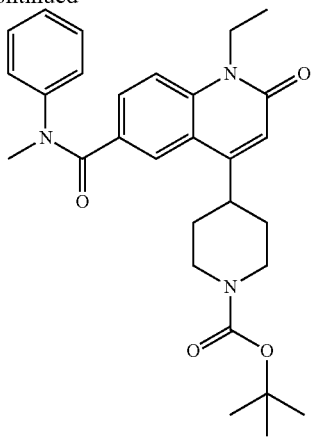

A mixture of 1.47 g of tert-butyl 4-(1-ethyl-6-(methyl (phenyl)carbamoyl)-2-oxo-1,2-dihydroquinolin-4-yl)-3,6-dihydropyridine-1(2H)-carboxylate, 0.44 g of 5% palladium-carbon, 0.29 g of ammonium formate, and 15 mL of methanol was heated at reflux under nitrogen atmosphere for 1 hour and 30 minutes. The reaction mixture was cooled to room temperature and the insoluble matter was filtered off. The filter residue was washed with ethyl acetate. The filtrate was combined with the wash solution, and the solvent was distilled off under reduced pressure. To the obtained residue were added 0.44 g of 5% palladium-carbon, 0.29 g of ammonium formate, and 15 mL of methanol, and the mixture was heated at reflux under nitrogen atmosphere for 2 hours. The reaction mixture was cooled to room temperature and the insoluble matter was filtered off. The filter residue was washed with ethyl acetate. The filtrate was combined with the wash solution, and the solvent was distilled off under reduced pressure. To the obtained residue was added diisopropyl ether, and the solid matter was filtered and washed with diisopropyl ether to obtain 1.26 g of tert-butyl 4-(1-ethyl-6-(methyl(phenyl)carbamoyl)-2-oxo-1,2-dihydroquinolin-4-yl)piperidine-1-carboxylate as a white solid.

$^1$H-NMR (CDCl$_3$) δ: 1.31 (3H, t, J=7.3 Hz), 1.40-1.58 (4H, m), 1.50 (9H, s), 2.62-2.85 (3H, m), 3.56 (3H, s), 4.15-4.34 (4H, m), 6.49 (1H, s), 7.04-7.11 (2H, m), 7.12-7.20 (1H, m), 7.23-7.33 (3H, m), 7.61 (1H, d, J=2.0 Hz), 7.73 (1H, dd, J=8.6, 2.0 Hz).

EXAMPLE 7

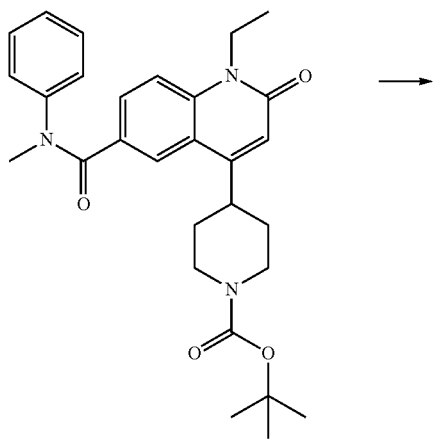

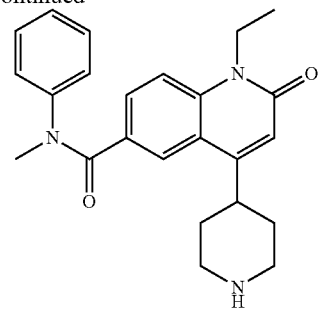

A mixture of 1.26 g of tert-butyl 4-(1-ethyl-6-(methyl (phenyl)carbamoyl)-2-oxo-1,2-dihydroquinolin-4-yl)-piperidine-1-carboxylate in 5 mL of dichloromethane and 5 mL of trifluoroacetic acid was stirred at room temperature for 30 minutes, and then the solvent was distilled off under reduced pressure. To the obtained residue were added ethyl acetate and saturated sodium hydrogen carbonate aqueous solution, and the organic layer was fractionated. The aqueous layer was extracted with ethyl acetate, and further extracted twice with chloroform. The organic layer was combined with the extract, and then dried over anhydrous magnesium sulfate, and the solvent was distilled off under reduced pressure to obtain 1.0 g of 1-ethyl-N-methyl-2-oxo-N-phenyl-4-(piperidin-4-yl)-1,2-dihydroquinoline-6-carboxamide as a white solid.

$^1$H-NMR (CDCl$_3$) δ: 1.31 (3H, t, J=7.3 Hz), 1.55-1.67 (4H, m), 2.67-2.90 (3H, m), 3.22-3.34 (2H, m), 3.56 (3H, s), 4.29 (2H, q, J=7.3 Hz), 6.55 (1H, s), 7.05-7.20 (3H, m), 7.22-7.32 (3H, m), 7.62 (1H, d, J=2.0 Hz), 7.71 (1H, dd, J=8.6, 2.0 Hz).

EXAMPLE 8

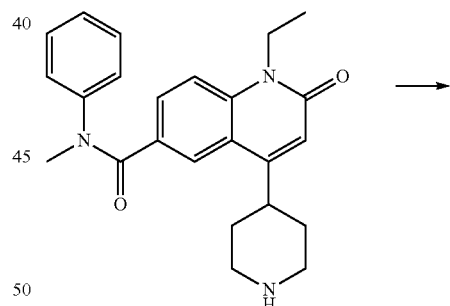

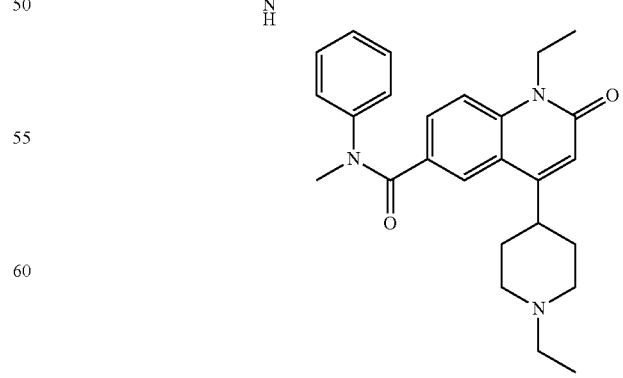

To a suspension of 1.0 g of 1-ethyl-N-methyl-2-oxo-N-phenyl-4-(piperidin-4-yl)-1,2-dihydroquinoline-6-carboxamide in 15 mL of acetone and 8 mL of tetrahydrofuran were added 0.71 g of potassium carbonate and 0.25 mL of ethyl iodide, and the mixture was stirred at room temperature for 30 minutes, and then stirred at the ambient temperature of 40° C. for 2 hours. After adding 0.24 g of potassium carbonate and 82 µL of ethyl iodide to the reaction mixture and stirring at the ambient temperature of 40° C. for 1 hour, the solvent was distilled off under reduced pressure. To the obtained residue were added ethyl acetate and water, the organic layer was fractionated, washed with saturated sodium chloride aqueous solution, and then dried over anhydrous magnesium sulfate, and the solvent was distilled off under reduced pressure. The obtained residue was purified by basic silica gel column chromatography [hexane:ethyl acetate gradient elution=50:50 to 0:100]. To the obtained residue was added diisopropyl ether, and the solid matter was filtered to obtain 0.76 g of 1-ethyl-4-(1-ethylpiperidin-4-yl)-N-methyl-2-oxo-N-phenyl-1,2-dihydroquinoline-6-carboxamide as a white solid.

$^1$H-NMR (DMSO-D$_6$) δ: 1.05 (3H, t, J=7.3 Hz), 1.15 (3H, t, J=7.3 Hz), 1.31-1.52 (4H, m), 1.92-2.06 (2H, m), 2.40 (2H, q, J=7.0 Hz), 2.47-2.63 (1H, m), 2.86-2.98 (2H, m), 3.43 (3H, s), 4.20 (2H, q, J=7.0 Hz), 6.36 (1H, s), 7.10-7.32 (5H, m), 7.50-7.58 (2H, m), 7.73 (1H, dd, J=8.9, 1.7 Hz).

EXAMPLE 9

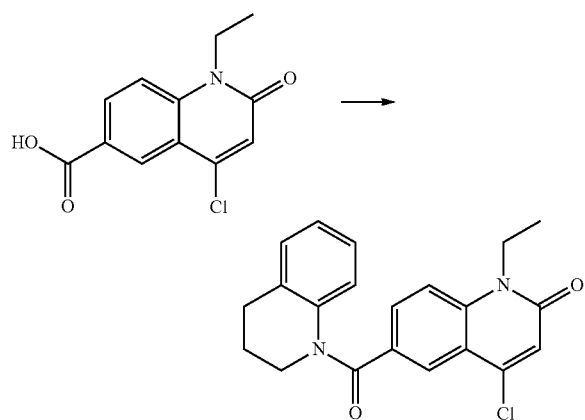

By the same method as Example 4, from 4-chloro-1-ethyl-2-oxo-1,2-dihydroquinoline-6-carboxylic acid was obtained 4-chloro-6-(3,4-dihydroquinolin-1(2H)-ylcarbonyl)-1-ethylquinolin-2 (1H)-one $^1$H-NMR (CDCl$_3$) δ: 1.31 (3H, t, J=7.2 Hz), 2.10 (2H, quint, J=6.6 Hz), 2.88 (2H, t, J=6.6 Hz), 3.96 (2H, t, J=6.7 Hz), 4.30 (2H, q, J=7.2 Hz), 6.65 (1H, d, J=7.8 Hz), 6.83-6.90 (2H, m), 7.00-7.06 (1H, m), 7.18-7.28 (2H, m), 7.56 (1H, dd, J=8.8, 2.0 Hz), 8.09 (1H, d J=2.2 Hz).

EXAMPLE 10

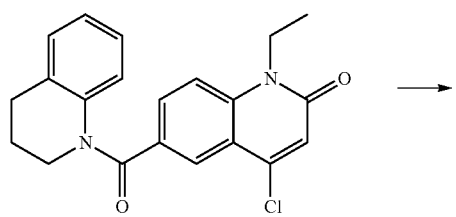

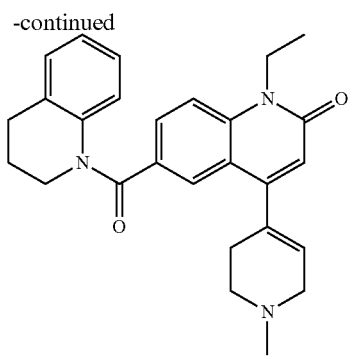

A mixture of 64 mg of 4-chloro-6-(3,4-dihydroquinolin-1(2H)-ylcarbonyl)-1-ethylquinolin-2(1H)-one, 47 mg of 1-methyl-4-(4,4,5,5-tetramethyl-1,3,2-dioxaborolan-2-yl)-1,2,3,6-tetrahydropyridine, 55 mg of sodium carbonate, 12.3 mg of bis(di-tert-butyl(4-dimethylaminophenyl)phosphine) dichloropalladium(II), 2 mL of ethylene glycol dimethyl ether, and 0.2 mL of water was heated at reflux under nitrogen atmosphere for 2 hours. The reaction mixture was cooled to room temperature, and then ethyl acetate and water were added. The organic layer was fractionated, washed successively with water and saturated sodium chloride aqueous solution, and then dried over anhydrous magnesium sulfate, and the solvent was distilled off under reduced pressure. The obtained residue was purified by basic silica gel chromatography [hexane:ethyl acetate gradient elution=50:50 to 0:100] to obtain 62 mg of 6-(3,4-dihydroquinolin-1(2H)-ylcarbonyl)-1-ethyl-4-(1-methyl-1,2,3,6-tetrahydropyridin-4-yl)quinolin-2(1H)-one as a slightly brown foam.

$^1$H-NMR (CDCl$_3$) δ: 1.35 (3H, t, J=6.9 Hz), 2.05-2.18 (4H, m), 2.41 (3H, s), 2.45-2.55 (2H, m), 2.87 (2H, t, J=6.6 Hz), 2.94-3.02 (2H, m), 3.95 (2H, t, J=6.6 Hz), 4.33 (2H, q, J=7.1 Hz), 5.29-5.36 (1H, m), 6.47 (1H, s), 6.54 (1H, d, J=7.9 Hz), 6.80-6.89 (1H, m), 6.94-7.02 (1H, m), 7.18 (1H, d, J=7.3 Hz), 7.35 (1H, d, J=9.2 Hz), 7.49 (1H, d, J=2.0 Hz), 7.77 (1H, dd, J=8.6, 2.0 Hz).

EXAMPLE 11

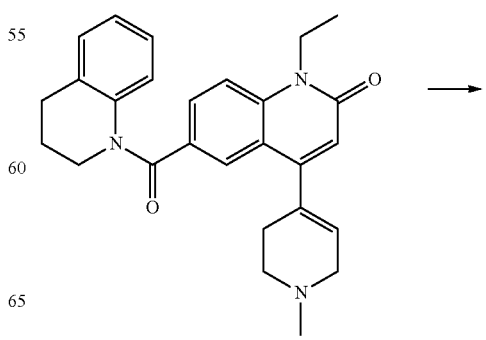

-continued

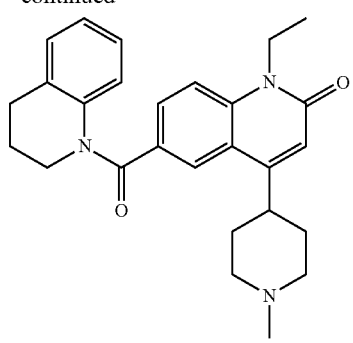

A mixture of 60 mg of 6-(3,4-dihydroquinolin-1(2H)-ylcarbonyl)-1-ethyl-4-(1-methyl-1,2,3,6-tetrahydropyridin-4-yl)quinolin-2(1H)-one in 15 mL of methanol and 15 mL of ethyl acetate was subjected to hydrogenation reaction (25° C., 1 bar, flow rate 2 mL/min, 10% palladium-carbon) using the flow type hydrogenation reaction apparatus. The solvent was distilled off under reduced pressure, and then the obtained residue was purified by basic silica gel column chromatography [hexane:ethyl acetate gradient elution=50: 50 to 0:100]. To the obtained residue were added diisopropyl ether and ethyl acetate, and the solid matter was filtered to obtain 10 mg of 6-(3,4-dihydroquinolin-1(2H)-ylcarbonyl)-1-ethyl-4-(1-methylpiperidin-4-yl)quinolin-2(1H)-one as a white solid.

$^1$H-NMR (DMSO-D$_6$) δ: 1.18 (3H, t, J=6.9 Hz), 1.24-1.52 (4H, m), 1.80-1.94 (2H, m), 1.95-2.10 (2H, m), 2.19 (3H, s), 2.50-2.65 (1H, m), 2.70-2.81 (2H, m), 2.87 (2H, t, J=6.3 Hz), 3.81 (2H, t, J=6.6 Hz), 4.24 (2H, q, J=6.8 Hz), 6.38 (1H, s), 6.58 (1H, d, J=7.9 Hz), 6.84 (1H, t, J=7.3 Hz), 6.96 (1H, t, J=7.3 Hz), 7.22 (1H, d, J=7.3 Hz), 7.50-7.55 (1H, m), 7.62 (1H, d, J=9.2 Hz), 7.73-7.81 (1H, m).

EXAMPLE 12

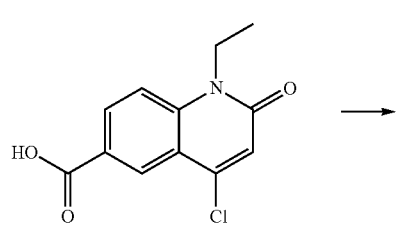

By the same method as Example 4, from 4-chloro-1-ethyl-2-oxo-1,2-dihydroquinoline-6-carboxylic acid was obtained 4-chloro-1-ethyl-N-methyl-N-(4-methylphenyl)-2-oxo-1,2-dihydroquinoline-6-carboxamide.

$^1$H-NMR (CDCl$_3$) δ: 1.29 (3H, t, J=7.2 Hz), 2.29 (3H, s), 3.51 (3H, s), 4.26 (2H, q, J=7.1 Hz), 6.81 (1H, s), 6.98 (2H, d, J=8.3 Hz), 7.07 (2H, d, J=8.3 Hz), 7.20 (1H, d, J=8.8 Hz), 7.65 (1H, dd, J=8.8, 2.0 Hz), 7.94 (1H, d, J=2.0 Hz).

EXAMPLE 13

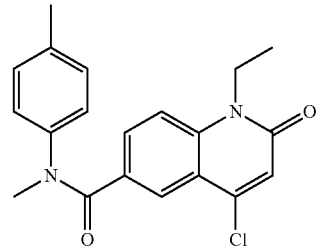

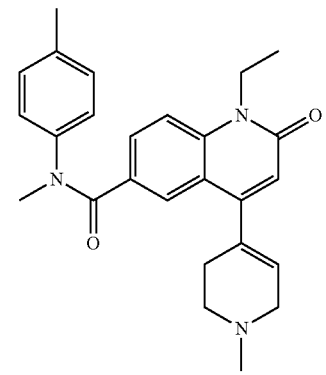

By the same method as Example 10, from 4-chloro-1-ethyl-N-methyl-N-(4-methylphenyl)-2-oxo-1,2-dihydroquinoline-6-carboxamide was obtained 1-ethyl-N-methyl-N-(4-methylphenyl)-4-(1-methyl-1,2,3,6-tetrahydropyridin-4-yl)-2-oxo-1,2-dihydroquinoline-6-carboxamide.

$^1$H-NMR (CDCl$_3$) δ: 1.31 (3H, t, J=7.2 Hz), 2.14-2.21 (2H, m), 2.26 (3H, s), 2.45 (3H, s), 2.61 (2H, t, J=5.6 Hz), 3.04-3.11 (2H, m), 3.50 (3H, s), 4.29 (2H, q, J=7.1 Hz), 5.36-5.42 (1H, m), 6.45 (1H, s), 6.92 (2H, d, J=8.3 Hz), 7.03 (2H, d, J=8.5 Hz), 7.27 (1H, d, J=8.8 Hz), 7.51 (1H, d, J=2.0 Hz), 7.69 (1H, dd, J=8.9, 2.1 Hz).

EXAMPLE 14

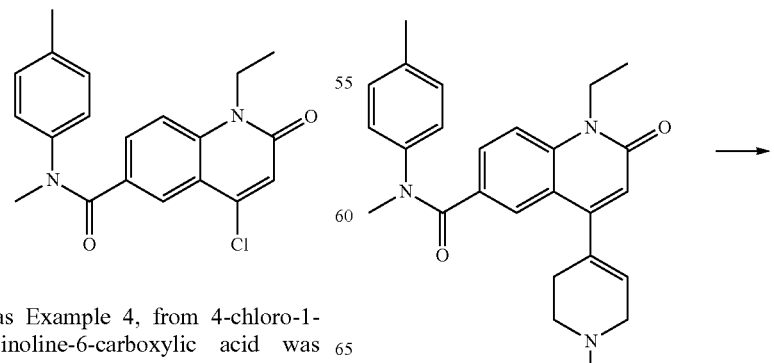

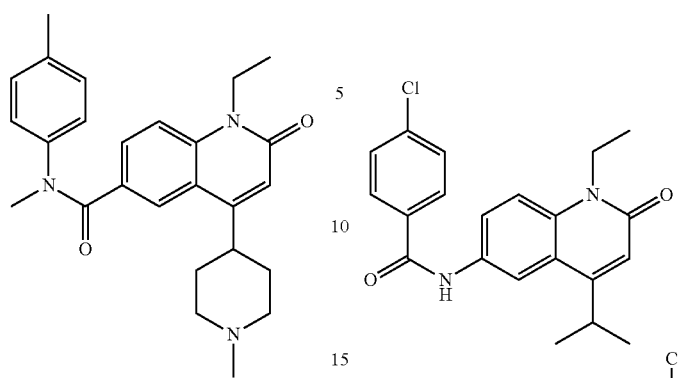

By the same method as Reference Example 13, from 1-ethyl-N-methyl-N-(4-methylphenyl)-4-(1-methyl-1,2,3,6-tetrahydropyridin-4-yl)-2-oxo-1,2-dihydroquinoline-6-carboxamide was obtained 1-ethyl-N-methyl-N-(4-methylphenyl)-4-(1-methylpiperidin-4-yl)-2-oxo-1,2-dihydroquinoline-6-carboxamide.

$^1$H-NMR (CDCl$_3$) δ: 1.30 (3H, t, J=7.1 Hz), 1.50-1.71 (4H, m), 1.99-2.10 (2H, m), 2.26 (3H, s), 2.36 (3H, s), 2.48-2.59 (1H, m), 2.91-3.00 (2H, m), 3.53 (3H, s), 4.28 (2H, q, J=7.2 Hz), 6.55 (1H, s), 6.96 (2H, d, J=8.3 Hz), 7.06 (2H, d, J=8.0 Hz), 7.25-7.30 (1H, m), 7.60 (1H, d, J=2.0 Hz), 7.71 (1H, dd, J=8.8, 2.0 Hz).

EXAMPLE 15

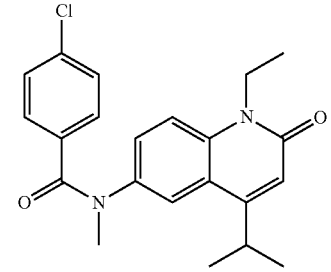

By the same method as Example 1, from 6-amino-1-ethyl-4-(propan-2-yl)quinolin-2(1H)-one and 4-chlorobenzoyl chloride was obtained 4-chloro-N-(1-ethyl-2-oxo-4-(propan-2-yl)-1,2-dihydroquinolin-6-yl)benzamide.

$^1$H-NMR (CDCl$_3$) δ: 1.34 (6H, d, J=6.6 Hz), 1.31-1.40 (3H, m), 3.34-3.47 (1H, m), 4.37 (2H, q, J=7.1 Hz), 6.67 (1H, s), 7.42 (1H, d, J=9.2 Hz), 7.48 (2H, d, J=8.3 Hz), 7.77 (1H, dd, J=9.2, 2.3 Hz), 7.91 (2H, d, J=8.3 Hz), 8.23 (1H, s), 8.33 (1H, d, J=2.3 Hz).

EXAMPLE 16

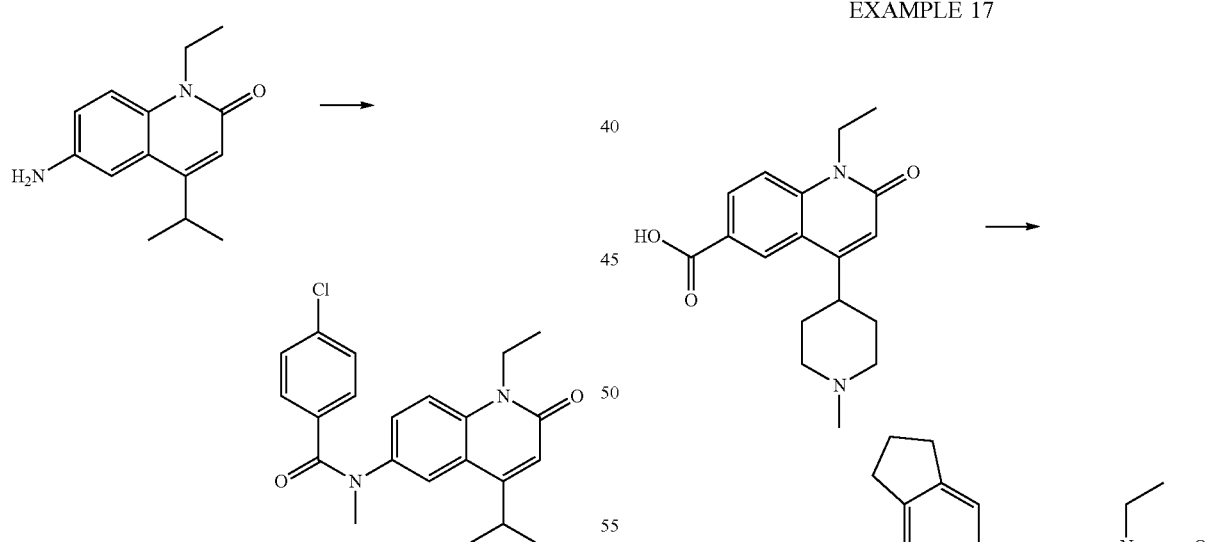

By the same method as Example 2, from 4-chloro-N-(1-ethyl-2-oxo-4-(propan-2-yl)-1,2-dihydroquinolin-6-yl)benzamide was obtained 4-chloro-N-(1-ethyl-2-oxo-4-(propan-2-yl)-1,2-dihydroquinolin-6-yl)-N-methylbenzamide.

$^1$H-NMR (CDCl$_3$) δ: 1.12 (6H, d, J=6.8 Hz), 1.34 (3H, t, J=7.2 Hz), 3.01-3.14 (1H, m), 3.53 (3H, s), 4.31 (2H, q, J=7.2 Hz), 6.61 (1H, s), 7.12-7.19 (2H, m), 7.24-7.29 (2H, m), 7.31-7.37 (3H, m).

EXAMPLE 17

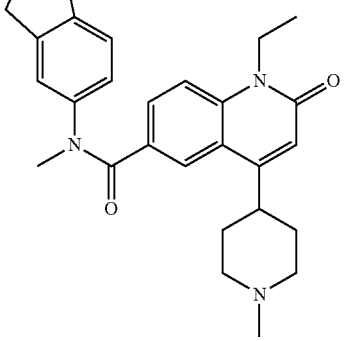

A mixture of 80 mg of 1-ethyl-4-(1-methylpiperidin-4-yl)-2-oxo-1,2-dihydroquinoline-6-carboxylic acid, 80 μL of N-methyl-2,3-dihydro-1H-inden-5-amine, 3 mL of dichloromethane, 90 mg of 1-ethyl-3-(3-dimethylaminopropyl)carbodiimide hydrochloride, 63 mg of 1-hydroxy-7-azabenzotriazole and 0.3 mL of triethylamine was stirred in a sealed tube at the ambient temperature of 70-80° C. for 3 hours. The reaction mixture was cooled to room temperature and then the solvent was distilled off under reduced pressure. To the obtained residue were added 1 mL of 2 mol/L sodium hydroxide aqueous solution, 4 mL of tetrahydrofuran, and 2 mL of methanol, and the mixture was stirred at the ambient temperature of 40-50° C. for 20 minutes, and the solvent was distilled off under reduced pressure. To the reaction mixture were added ethyl acetate and saturated sodium chloride aqueous solution, the organic layer was fractionated, and the aqueous layer was extracted with ethyl acetate. The organic layer was combined with the extract, and then dried over anhydrous magnesium sulfate, and the solvent was distilled off under reduced pressure. The obtained residue was purified by silica gel column chromatography [chloroform:methanol gradient elution=100:0 to 80:20] to obtain 8 mg of N-(2,3-dihydro-1H-inden-5-yl)-1-ethyl-N-methyl-4-(1-methylpiperidin-4-yl)-2-oxo-1,2-dihydroquinoline-6-carboxamide as a white solid.

$^1$H-NMR (DMSO-D$_6$) δ: 1.15 (3H, t, J=7.0 Hz), 1.36-1.57 (4H, m), 1.89-2.06 (4H, m), 2.24 (3H, s), 2.69-2.89 (6H, m), 3.29-3.37 (1H, m), 3.39 (3H, s), 4.21 (2H, q, J=7.1 Hz), 6.38 (1H, s), 6.84-6.92 (1H, m), 7.07 (1H, d, J=8.0 Hz), 7.15 (1H, s), 7.52-7.61 (2H, m), 7.75 (1H, dd, J=8.9, 1.6 Hz).

EXAMPLE 18

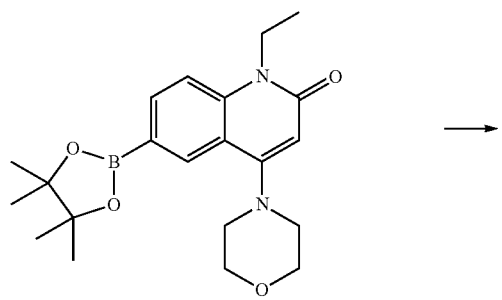

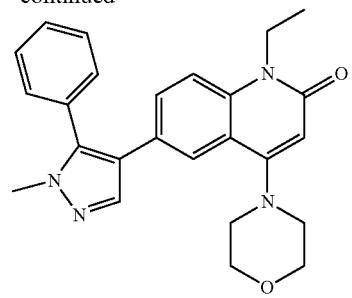

By the same method as Reference Example 2, from 1-ethyl-4-(morpholin-4-yl)-6-(4,4,5,5-tetramethyl-1,3,2-dioxaborolan-2-yl)quinolin-2(1H)-one and 4-bromo-1-methyl-5-phenyl-1H-pyrazole was obtained 1-ethyl-6-(1-methyl-5-phenyl-1H-pyrazol-4-yl)-4-(morpholin-4-yl)quinolin-2(1H)-one.

$^1$H-NMR (DMSO-D$_6$) δ: 1.17 (3H, t, J=6.9 Hz), 2.65-2.76 (4H, m), 3.42-3.53 (4H, m), 3.74 (3H, s), 4.21 (2H, q, J=6.8 Hz), 5.95 (1H, s), 7.35 (1H, d, J=2.0 Hz), 7.37-7.64 (7H, m), 7.81 (1H, s).

EXAMPLES 19-244

Confirming to the procedure described in the specification, the compounds indicated in Tables 1-25 were produced by publicly known reactions, such as condensation, addition, oxidization, reduction, rearrangement, substitution, halogenation, dehydration, hydrolysis or the like, or the appropriate combination of these reactions.

TABLE 1

| Example No. | Structural Formula | Compound Name | MS |
|---|---|---|---|
| 19 | | N-(1-ethyl-4-(1-methylpiperidin-4-yl)-2-oxo-1,2-dihydroquinolin-6-yl)-N-methylbenzamide | 404(M + H) |

TABLE 1-continued

| Example No. | Structural Formula | Compound Name | MS |
|---|---|---|---|
| 20 | | N-(1-ethyl-4-(octahydroisoquinolin-2(1H)-yl)-2-oxo-1,2-dihydroquinolin-6-yl)-N-methylbenzamide | 444(M + H) |
| 21 | | N-(1-ethyl-4-(morpholin-4-yl)-2-oxo-1,2-dihydroquinolin-6-yl)-2-hydroxy-N-methylbenzamide | 408(M + H) |
| 22 | | N-(1-ethyl-4-(morpholin-4-yl)-2-oxo-1,2-dihydroquinolin-6-yl)-N-methyl-2-(trifluoromethoxy)benzamide | 476(M + H) |
| 23 | | 2-cyano-N-(1-ethyl)-4-(morpholin-4-yl)-2-oxo-1,2-dihydroquinolin-6-yl)-N-methylbenzamide | 417(M + H) |
| 24 | | N-(1-ethyl-4-(morpholin-4-yl)-2-oxo-1,2-dihydroquinolin-6-yl)-N-methyl-4-propylbenzamide | 434(M + H) |

TABLE 1-continued

| Example No. | Structural Formula | Compound Name | MS |
|---|---|---|---|
| 25 | | 3-ethoxy-N-(1-ethyl-4-(morpholin-4-yl)-2-oxo-1,2-dihydroquinolin-6-yl)-N-methylbenzamide | 436(M + H) |
| 26 | | N-(1-ethyl-4-(morpholin-4-yl)-2-oxo-1,2-dihydroquinolin-6-yl)-N-methyl-2-(trifluoromethyl)benzamide | 460(M + H) |
| 27 | | N-(1-ethyl-4-(morpholin-4-yl)-2-oxo-1,2-dihydroquinolin-6-yl)-2-fluoro-N-methylbenzamide | 410(M + H) |

TABLE 2

| Example No. | Structural Formula | Compound Name | MS |
|---|---|---|---|
| 28 | | N-(4-((E)-2-cyclopropylvinyl)-1-ethyl-2-oxo-1,2-dihydroquinolin-6-yl)-N-methylbenzamide | 373(M + H) |

TABLE 2-continued

| Example No. | Structural Formula | Compound Name | MS |
|---|---|---|---|
| 29 | | N-(1-ethyl-4-((1E)-4-hydroxybut-1-en-1-yl)-2-oxo-1,2-dihydroquinolin-6-yl)-N-methylbenzamide | 377(M + H) |
| 30 | | N-(4-butyl-1-ethyl-2-oxo-1,2-dihydroquinolin-6-yl)-N-methylbenzamide | 363(M + H) |
| 31 | | 4-cyclopropyl-N-(1-ethyl-4-(morpolin-4-yl)-2-oxo-1,2-dihydroquinolin-8-yl)-N-methylbenzamide | 432(M + H) |
| 32 | | 4-((E)-2-cyclopropylvinyl)-N-(1-ethyl-4-(morpholin-4-yl)-2-oxo-1,2-dihydroquinolin-6-yl)-N-methylbenzamide | 458(M + H) |
| 33 | | N-(1-ethyl-4-(morphoiln-4-yl)-2-oxo-1,2-dihydroquinolin-6-yl)-N-methyl-4-(1-methyl-1,2,3,6-tetrahydropyridin-4-yl)benzamide | 487(M + H) |

TABLE 2-continued

| Example No. | Structural Formula | Compound Name | MS |
|---|---|---|---|
| 34 | | 4-(cyclohe-1-en-1-yl)-N-(1-ethyl-4-(morpholin-4-yl)-2-oxa-1,2-dihydroquinolin-6-yl)-N-methylbenzamide | 472(M + H) |
| 35 | | N-(4-(2-cyclopropylethyl)-1-ethyl-2-oxo-1,2-dihydroquinolin-6-yl)-N-methylenzamide | 375(M + H) |
| 36 | | N-(1,4-diethyl-2-oxo-1,2-dihydroquinolin-6-yl)-N-methylbenzamide | 335(M + H) |

TABLE 3

| Example No. | Structural Formula | Compound Name | MS |
|---|---|---|---|
| 37 | | N-(1-ethyl-4-(4-hydroxybutyl)-2-oxo-1,2-dibydroquinolin-6-yl)-methylbenzamide | 379(M + H) |

TABLE 3-continued

| Example No. | Compound Name | MS |
|---|---|---|
| 38 | 4-(2-cyclopropylethyl)-N-(1-ethyl-4-(morpholin-4-yl)-2-oxo-1,2-dihydroquinolin-6-yl)-N-methylbenzamide | 460(M + H) |
| 39 | N-1-(ethyl-4-(morpholin-4-yl)-2-oxo-1,2-dihydroquinolin-6-yl)-N-methyl-4-(1-methylpiperidin-4-yl)-benzamide | 489(M + H) |
| 40 | 4-cyclohexyl-N-(1-ethyl-4-(morpholin-4-yl)-2-oxo-1,2-dihydroquinolin-6-yl)-N-methylbenzamide | 474(M + H) |
| 41 | N-(1-ethyl-4-(morpholin-4-yl)-2-oxo-1,2-dihydroquinolin-6-yl)-4-((1E)-4-hydroxybut-1-en-1-yl)-N-methylbenzamide | 462(M + H) |
| 42 | N-(1-ethyl-4-(morpholin-4-yl)-2-oxo-1,2-dihydroquinolin-6-yl)-N-methyl-4-sulfamoylbenzamide | 471(M + H) |

TABLE 3-continued

| Example No. | Structural Formula | Compound Name | MS |
|---|---|---|---|
| 43 | | N-(1-ethyl-4-(morpholin-4-yl)-2-oxo-1,2-dihydroquinolin-6-yl)-N-methyl-4-(methylsulfonyl)benzamide | 470(M + H) |
| 44 | | 4-(dimethylamino)-N-(1-ethyl-4-(morpholin-4-yl)-2-oxo-1,2-dihydroquinolin-6-yl)-N-methylbenzamide | 435(M + H) |
| 45 | | 4-ethyl-N-(1-ethyl-4-(mopholin-4-yl)-2-oxo-1,2-dihydroquinolin-6-yl)-N-methylbenzamide | 420(M + H) |

TABLE 4

| Example No. | Structural Formula | Compound Name | MS |
|---|---|---|---|
| 46 | | N-(1-ethyl-4-(morpholin-4-yl)-2-oxo-1,2-dihydroquinolin-6-yl)-N-methyl-4-(propan-2-yl)benzamide | 434(M + H) |

TABLE 4-continued

| Example No. | Structural Formula | Compound Name | MS |
|---|---|---|---|
| 47 | | 2-amino-N-(4-cydopropyl-1-ethyl-2-oxo-1,2-dihydroquinolin-6-yl)-N-methyl-4-(trifluoromethyl)benzamide | 430(M + H) |
| 48 | | 2-amino-N-(4-cyclopropyl-1-ethyl-2-oxo-1,2-dihydroquinolin-6-yl)-4-fluoro-N-methylbenzamide | 360(M + H) |
| 49 | | 2-amino-N-(4-cyclopropyl-1-ethyl-2-oxo-1,2-dihydroquinolin-6-yl)-N-methylbenzamide | 362(M + H) |
| 50 | | 2-amino-4-cyclopropyl-N-(4-cyclopropyl-1-ethyl-2-oxo-1,2-dihydroquinolin-6-yl)-N-methylbenzamide | 402(M + H) |
| 51 | | 2-amino-4-(2-cyclopropylethyl)-N-(4-cyclopropyl-1-ethyl-2-oxo-1,2-dihydroquinolin-6-yl)-N-methylbenzamide | 430(M + H) |
| 52 | | 2-amino-N-(4-cyclopropyl-1-ethyl-2-oxo-1,2-dihydroquinolin-6-yl)-N-methyl-4-(propan-2-yl)benzamide | 404(M + H) |

TABLE 4-continued

| Example No. | Structural Formula | Compound Name | MS |
|---|---|---|---|
| 53 | | 2-amino-N-(4-cyclopropyl-1-ethyl-2-oxo-1,2-dihydroquinolin-6-yl)-4-ethyl-N-methylbenzamide | 390(M + H) |
| 54 | | 2-amino-N-(4-cyclopropyl-1-ethyl-2-oxo-1,2-dihydroquinolin-6-yl)-N-methyl-4-propylbenzamide | 404(M + H) |
| 55 | | N-(1-ethyl-2-oxo-4-(propan-2yl)-1,2-dihydroquinolin-6-yl)-N-methylbenzamide | 349(M + H) |

TABLE 5

| Example No. | Structural Formula | Compound Name | MS |
|---|---|---|---|
| 56 | | N-(4-cyclopropyl-1-ethyl-2-oxo-1,2-dihydroquinoin-6-yl)-N-methyl-4-propylbenzamide | 389(M + H) |
| 57 | | N-(4-cyclopropyl-1-ethyl-2-oxo-1,2-dihydroquinoin-6-yl)-N-methyl-4-(propan-2-yl)benzamide | 389(M + H) |

TABLE 5-continued

| Example No. | Structural Formula | Compound Name | MS |
|---|---|---|---|
| 58 | | N-(4-cyclopropyl-1-ethyl-2-oxo-1,2-dihydroquinoin-6-yl)-4-ethyl-N-methylbenzamide | 375(M + H) |
| 59 | | 4-(2-cyclopropylethyl)-N-(4-cyclopropyl-1-ethyl-2-oxo-1,2-dihydroquinolin-6-yl)-N-methylbenzamide | 415(M + H) |
| 60 | | 4 cyclopropyl-N-(4-cyclopropyl-1-ethyl-2-oxo-1,2-dihydroquinolin-6-yl)-N-methylbenzamide | 387(M + H) |
| 61 | | N-(4-cyclopropyl-1-ethyl-2-oxo-1,2-dihydroquinolin-6-yl)-4-fluoro-N-methylbenzamide | 365(M + H) |
| 62 | | 2-amino-N-(1-ethyl-2-oxo-4-(propan-2-yl)-1,2-dihydroquinolin-6-yl)-4-fluoro-N-methylbenzamide | 382(M + H) |
| 63 | | 2-amino-4-cyclopropyl-N-(1-ethyl-2-oxo-4-(propan-2-yl)-1,2-dihydroquinolin-6-yl)-N-methylbenzamide | 404(M + H) |

TABLE 5-continued

| Example No. | Structural Formula | Compound Name | MS |
|---|---|---|---|
| 64 | | 2-amino-N-(1-ethyl-2-oxo-4-(propan-2-yl)-1,2-dihydroquinolin-6-yl)-N-methylbenzamide | 364(M + H) |
| 65 | | 2-amino-N-(1-ethyl-2-oxo-4-(propan-2-yl)-1,2-dihydroquinolin-6-yl)-N-methyl-4-(trifluoromethyl)benzamide | 432(M + H) |

TABLE 6

| Example No. | Structural Formula | Compound Name | MS |
|---|---|---|---|
| 66 | | 2-amino-N-(1-ethyl-2-oxo-4-(propan-2-yl)-1,2-dihydroquinolin-6-yl)-N-methyl-4-(propan-2-yl)benzamide | 406(M + H) |
| 67 | | 2-amino-4-ethyl-N-(1-ethyl-2-oxo-4-(propan-2-yl)-1,2-dihydroquinolin-6-yl)-N-methylbenzamide | 392(M + H) |
| 68 | | 2-amino-N-(1-ethyl-2-oxo-4-(propan-2-yl)-1,2-dihydroquinolin-6-yl)-N-methyl-4-propylbenzamide | 406(M + H) |

TABLE 6-continued

| Example No. | Compound Name | MS |
|---|---|---|
| 69 | N-(4-cyclopropyl-1-ethyl-2-oxo-1,2-dihydroquinolin-6-yl)-4-(ethylamino)-N-methylbenzamide | 390(M + H) |
| 70 | N-(4-cyclopropyl-1-ethyl-2-oxo-1,2-dihydroquinolin-6-yl)-4-(ethylamino)-N-methylbenzamide | 390(M + H) |
| 71 | N-(4-cyclopropyl-1-ethyl-2-oxo-1,2-dihydroquinolin-6-yl)-N-methyl-4-(phenylamino)benzamide | 438(M + H) |
| 72 | N-(4-cydopropyl-1-ethyl-2-oxo-1,2-dihydroquinolin-6-yl)-N-methyl-4-(methyl(propyl)amino)benzamide | 418(M + H) |
| 73 | N-(4-cyclopropyl-1-ethyl-2-oxo-1,2-dihydroquinolin-6-yl)-N-methyl-4-(piperidin-1-yl)benzamide | 430(M + H) |

TABLE 6-continued

| Example No. | Structural Formula | Compound Name | MS |
|---|---|---|---|
| 74 | | 2-amino-N-(1-ethyl-4-methyl-2-oxo-1,2-dihydroquinolin-6-yl)-4-fluoro-N-methylbenzamide | 354(M + H) |
| 75 | | N-(4-(butan-2-yl)-1-ethyl-2-oxo-1,2-dihydroquinolin-6-yl)-N-methylbenzamide | 363(M + H) |

TABLE 7

| Example No. | Structural Formula | Compound Name | MS |
|---|---|---|---|
| 76 | | N-(4-cyclopropyl-1-ethyl-2-oxo-1,2-dihydroquinolin-6-yl)-N,2-dimethylbenzamide | 361(M + H) |
| 77 | | N-(4-cyclopropyl-1-ethyl-2-oxo-1,2-dihydroquinolin-6-yl)-N,3-dimethylbenzamide | 361(M + H) |
| 78 | | N-(4-cyclopropyl-1-ethyl-2-oxo-1,2-dihydroquinolin-6-yl)-N,4-dimethylbenzamide | 361(M + H) |

TABLE 7-continued

| Example No. | Structural Formula | Compound Name | MS |
|---|---|---|---|
| 79 | | N-(4-cyclopropyl-1-ethyl-2-oxo-1,2-dihydroquinolin-6-yl)-2-methoxy-N-methylbenzamide | 377(M + H) |
| 80 | | N-(4-cyclopropyl-1-ethyl-2-oxo-1,2-dihydroquinolin-6-yl)-3-methoxy-N-methylbenzamide | 377(M + H) |
| 81 | | N(4-cyclopropyl-1-ethyl-2-oxo-1,2-dihydroquinolin-6-yl)-4-(diethylamino)-N-methylbenzamide | 418(M + H) |
| 82 | | 4-tert-butyl-N-(4-cyclopropropyl-1-ethyl-2-oxo-1,2-dihydroquinolin-6-yl)-N-methylbenzamide | 403(M + H) |
| 83 | | N-(4-cyclopropyl-1-ethyl-2-oxo-1,2-dihydroquinolin-6-yl)-2-hydroxy-N-methylbenzamide | 363(M + H) |
| 84 | | N-(4-cyclopropyl-1-ethyl-2-oxo-1,2-dihydroquinolin-6-yl)-3-hydroxy-N-methylbenzamide | 363(M + H) |

TABLE 7-continued

| Example No. | Structural Formula | Compound Name | MS |
|---|---|---|---|
| 85 | | 3-amino-N-(4-cyclopropyl-1-ethyl-2-oxo-1,2-dihydroquinolin-6-yl)-N-methylbenzamide | 362(M + H) |

TABLE 8

| Example No. | Structural Formula | Compound Name | MS |
|---|---|---|---|
| 86 | | 4-amino-N-(4-cyclopropyl-1-ethyl-2-oxo-1,2-dihydroquinolin-6-yl)-N-methylbenzamide | 363(M + H) |
| 87 | | N-(4-cyclopropyl-1-ethyl-2-oxo-1,2-dihydroquinolin-6-yl)-3-(dimethylamino)-N-methylbenzamide | 390(M + H) |
| 88 | | 4-(acetylamino)-N-(4-cyclopropyl-1-ethyl-2-oxy-1,2-dihydroquinolin-6-yl)-N-methylbenzamide | 404(M + H) |
| 89 | | 3-(acetylamino)-N-(4-cyclopropyl-1-ethyl-2-oxo-1,2-dihydroquinolin-6-yl)-N-methylbenzamide | 404(M + H) |

TABLE 8-continued

| Example No. | Structural Formula | Compound Name | MS |
|---|---|---|---|
| 90 | | 2-(acetylamino)-N-(4-cyclopropyl-1-ethyl-2-oxo-1,2-dihdroquinolin-6-yl)-N-methylbenzamide | 404(M + H) |
| 91 | | N-(4 cyclopropyl-1-ethyl-2-oxo-1,2-dihydroquinolin-6-yl)-N-methyl-4-((methylsulfonyl)amino)benzamide | 440(M + H) |
| 92 | | N-(4-cyclopropyl-1-ethyl-2-oxo-1,2-dihydroquinolin-6-yl)-N-methyl-3-((methylsulfonyl)amino)benzamide | 440(M + H) |
| 93 | | N-(4-cyclopropyl-1-ethyl-2-oxo-1,2-dihydroquinolin-6-yl)-N-methyl-2-((methylsulfonyl)amino)benzamide | 440(M + H) |
| 94 | | 2-amino-N-(4-cyclopropyl-1-ethyl-2-oxo-1,2-dihydroquinolin-6-yl)-N,4-methylbenzamide | 376(M + H) |
| 95 | | N-(4-cyclopropyl-1-ethyl-2-oxo-1,2-dihydroquinolin-6-yl)-N-methyl-2-(methylamino)benzamide | 376(M + H) |

TABLE 8-continued

| Example No. | Structural Formula | Compound Name | MS |
|---|---|---|---|
| 96 | | N-(4-cyclopropyl-1-ethyl-2-oxo-1,2-dihydroquinolin-6-yl)-2-(dimethylamino)-N-methylbenzamide | 390(M + H) |

TABLE 9

| Example No. | Structural Formula | Compound Name | MS |
|---|---|---|---|
| 97 | | N-(1-ethyl-4-(1-(2-hydroxyethyl)piperidin-4-yl)-2-oxo-1,2-dihydroquinolin-6-yl)-N-methylbenzamide | 434(M + H) |
| 98 | | N-(1-ethyl-4-(1-(2-methoxyethyl)piperidin-4-yl)-2-oxo-1,2-dihydroquinolin-6-yl)-N-methylbenzamide | 448(M + H) |
| 99 | | 3-chloro-N-(1-ethyl-2-oxo-4-(piperidin-4-yl)-1,2-dihydroquinolin-6-yl)-N-methylbenzamide | 425(M + H) |

TABLE 9-continued

| Example No. | Structural Formula | Compound Name | MS |
|---|---|---|---|
| 100 | | N-(1-(ethyl-2-oxo-4-(1-(2,2,2-trifluoroethyl)piperidin-4-yl)-1,2-dihydroquinolin-6-yl)-N,4-dimethylbenzamide | 486(M + H) |
| 101 | | 3-chloro-N-(1-ethyl-2-oxo-4-(1-(2,2,2-trifluoroethyl)piperidin-4-yl)-1,2-dihydroquinolin-6-yl)-N-methylbenzamide | 507(M + H) |
| 102 | | 3-chloro-N-(4-(1-(cyanomethyl)piperidin-4-yl)-1-ethyl-2-oxo-1,2-dihydroquinolin-6-yl)-N-methylbenzamide | 464(M + H) |
| 103 | | N-(1-ethyl-2-oxo-4-(4-oxocyclohexyl)-1,2-dihydroquinolin-6-yl)-N-methylbenzamide | 401(M − H) |

TABLE 10

| Example No. | Structural Formula | Compound Name | MS |
|---|---|---|---|
| 104 | | N-(4-(1-(cyanomethyl)piperidin-4-yl)-1-ethyl-2-oxo-1,2-dihydroquinolin-6-yl)-N-methylbenzamide | 429(M + H) |
| 105 | | N-(1-ethyl-2-oxo-4-(propan-2-yl)-1,2-dihydroquinolin-6-yl)-2-hydroxy-N,4-dimethylbenzamide | 377(M − H) |
| 106 | | 3-chloro-N-(1-ethyl-2-oxo-4-(propan-2-yl)-1,2-dihydroquinolin-6-yl)-N-methylbenzamide | 384(M + H) |
| 107 | | N-(1-ethyl-2-oxo-4-(propan-2-yl)-1,2-dihydroquinolin-6-yl)-2-hydroxy-N,5-dimethylbenzamide | 377(M − H) |
| 108 | | 2-(acetylamino)-N-(1-ethyl-2-oxo-4-(propan-2-yl)-1,2-dihydroquinolin-6-yl)-N,4-dimethylbenzamide | 418(M − H) |
| 109 | | 2-(acetylamino)-N-(1-ethyl-2-oxo-4-(propan-2-yl)-1,2-dihydroquinolin-6-yl)-4-fluoro-N-methylbenzamide | 422(M − H) |

TABLE 10-continued

| Example No. | Structural Formula | Compound Name | MS |
|---|---|---|---|
| 110 | | 4-chloro-N-(1-ethyl-4-(1-methylpiperidin-4-yl)-2-oxo-1,2-dihydroquinolin-6-yl)-N-methylbenzamide | 439(M + H) |
| 111 | | 2-amino-4-chloro-N-(1-ethyl-2-oxo-4-(propan-2-yl)-1,2-dihydroquinolin-6-yl)-N-methylbenzamide | 399(M + H) |
| 112 | | 3-amino-4-chloro-N-(1-ethyl-2-oxo-4-(propan-2-yl)-1,2-dihydroquinolin-6-yl)-N-methylbenzamide | 399(M + H) |
| 113 | | 4-amino-N-(1-ethyl-2-oxo-4-(propan-2-yl)-1,2-dihydroquinolin-6-yl)-2-hydroxy-N-methylbenzamide | 380(M + H) |

TABLE 11

| Example No. | Structural Formula | Compound Name | MS |
|---|---|---|---|
| 114 | | 4-chloro-N-(1-ethyl-2-oxo-4-(propan-2-yl)-1,2-dihydroquinolin-6-yl)-2-methoxy-N-methylbenzamide | 414(M + H) |

TABLE 11-continued

| Example No. | Structural Formula | Compound Name | MS |
|---|---|---|---|
| 115 | | 4-chloro-N-(1-ethyl-2-oxo-4-(propan-2-yl)-1,2-dihydroquinolin-6-yl)-3-methoxy-N-methylbenzamide | 414(M + H) |
| 116 | | 4-chloro-N-(1-ethyl-2-oxo-4-(propan-2-yl)-1,2-dihydroquinolin-6-yl)-3-(3-hydroxypropoxy)-N-methylbenzamide | 458(M + H) |
| 117 | | 4-chloro-3-(3-(dimethylamino)propoxy)-N-(1-ethyl-2-oxo-4-(propan-2-yl)-1,2-dihydroquinolin-6-yl)-N-methylbenzamide | 484(M + H) |
| 118 | | 4-chloro-N-(1-ethyl-2-oxo-4-(propan-2-yl)-1,2-dihydroquinolin-6-yl)-2-(3-hydroxypropoxy)-N-methylbenzamide | 458(M + H) |
| 119 | | 4-chloro-N-(1-ethyl-2-oxo-4-(propan-2-yl)-1,2-dihydroquinolin-6-yl)-2-((2-hydroxyethyl)amino)-N-methylbenzamide | 443(M + H) |
| 120 | | 4-chloro-2-((2-(dimethylamino)ethyl)amino)-N-(1-ethyl-2-oxo-4-(propan-2-yl)-1,2-dihydroquinolin-6-yl)-N-methylbenzamide | 469(M + H) |

TABLE 11-continued

| Example No. | Structural Formula | Compound Name | MS |
|---|---|---|---|
| 121 | | N-(1-ethyl-4-methyl-2-oxo-1,2-dihydroquinolin-6-yl)-N-methylthiophene-2-carboxamide | 327(M + H) |
| 122 | | N-(1-ethyl-4-methyl-2-oxo-1,2-dihydroquinolin-6-yl)-N-methylthiophene-3-carboxamide | 327(M + H) |
| 123 | | N-(1-ethyl-4-methyl-2-oxo-1,2-dihydroquinolin-6-yl)-N-methyl-1H-pyrrole-2-carboxamide | 310(M + H) |

TABLE 12

| Example No. | Structural Formula | Compound Name | MS |
|---|---|---|---|
| 124 | | N-(1-ethyl-4-(morpholin-4-yl)-2-oxo-1,2-dihydroquinolin-6-yl)-N-methylnaphthalene-2-carboxamide | 442(M + H) |
| 125 | | N-(1-ethyl-4-(morpholin-4-yl)-2-oxo-1,2-dihydroquinolin-6-yl)-N-methylnaphthalene-1-carboxamide | 442(M + H) |

TABLE 12-continued

| Example No. | Structural Formula | Compound Name | MS |
|---|---|---|---|
| 126 | | 4-tert-butyl-N-(1-ethyl-4-(morpholin-4-yl)-2-oxo-1,2-dihydroquinolin-6-yl)-N-methylbenzamide | 448(M + H) |
| 127 | | N-(1-ethyl-4-(morpholin-4-yl)-2-oxo-1,2-dihydroquinolin-6-yl)-4-methoxy-N-methylbenzamide | 422(M + H) |
| 128 | | N-(1-ethyl-4-(morpholin-4-yl)-2-oxo-1,2-dihydroquinolin-6-yl)-N-methylbiphenyl-4-carboxamide | 468(M + H) |
| 129 | | 4-cyano-N-(1-ethyl-4-(morpholin-4-yl)-2-oxo-1,2-dihydroquinolin-6-yl)-N-methylbenzamide | 417(M + H) |
| 130 | | N-(1-ethyl-4-(morpholin-4-yl)-2-oxo-1,2-dihydroquinolin-6-yl)-3-fluoro-N-methylbenzamide | 410(M + H) |

TABLE 12-continued

| Example No. | Structural Formula | Compound Name | MS |
|---|---|---|---|
| 131 | | 3-cyano-N-(1-ethyl-4-(morpholin-4-yl)-2-oxo-1,2-dihydroquinolin-6-yl)-N-methylbenzamide | 417(M + H) |
| 132 | | N-(1-ethyl-4-(morpholin-4-yl)-2-oxo-1,2-dihydroquinolin-6-yl)-N-methyl-3-(trifluoromethyl)benzamide | 460(M + H) |

TABLE 13

| Example No. | Structural Formula | Compound Name | MS |
|---|---|---|---|
| 133 | | N-(1-ethyl-4-(morpholin-4-yl)-2-oxo-1,2-dihydroquinolin-6-yl)-3-methoxy-N-methylbenzamide | 422(M + H) |
| 134 | | 3-(dimethylamino)-N-(1-ethyl-4-(morpholin-4-yl)-2-oxo-1,2-dihydroquinolin-6-yl)-N-methylbenzamide | 435(M + H) |

TABLE 13-continued

| Example No. | Structural Formula | Compound Name | MS |
|---|---|---|---|
| 135 | | N-(1-ethyl-4-(morpholin-4-yl)-2-oxo-1,2-dihydroquinolin-6-yl)-4-fluoro-N-methylbenzamide | 410(M + H) |
| 136 | | N-(1-ethyl-4-(morpholin-4-yl)-2-oxo-1,2-dihydroquinolin-6-yl)-N-methyl-4-(trifluoromethyl)benzamide | 460(M + H) |
| 137 | | N-(1-ethyl-4-(morpholin-4-yl)-2-oxo-1,2-dihydroquinolin-6-yl)-3-hydroxy-N-methylbenzamide | 408(M + H) |
| 138 | | 1-ethyl-N-methyl-4-(1-methyl-1,2,3,6-tetrahydropyridin-4-yl)-2-oxo-N-phenyl-1,2-dihydroquinoline-6-carboxamide | 402(M + H) |
| 139 | | 1-ethyl-N-methyl-4-(1-methylpiperidin-4-yl)-2-oxo-N-phenyl-1,2-dihydroquinoline-6-carboxamide | 404(M + H) |

TABLE 13-continued

| Example No. | Structural Formula | Compound Name | MS |
|---|---|---|---|
| 140 | | 4-cyclohexyl-1-ethyl-N-methyl-2-oxo-N-phenyl-1,2-dihydroquinoline-6-carboxamide | 389(M + H) |
| 141 | | 4-(cyclohex-1-en-1-yl)-1-ethyl-N-methyl-2-oxo-N-phenyl-1,2-dihydroquinoline-6-carboxamide | 387(M + H) |

TABLE 14

| Example No. | Structural Formula | Compound Name | MS |
|---|---|---|---|
| 142 | | 4-cyclopropyl-1-ethyl-N-methyl-2-oxo-N-phenyl-1,2-dihydroquinoline-6-carboxamide | 347(M + H) |
| 143 | | 6-(2,3-dihydro-1H-indol-1-ylcarbonyl)-1-ethyl-4-(1-methylpiperidin-4-yl)quinolin-2(1H)-one | 416(M + H) |

TABLE 14-continued

| Example No. | Structural Formula | Compound Name | MS |
|---|---|---|---|
| 144 | | 4-((1-ethyl-4-(1-methylpiperidin-4-yl)-2-oxo-1,2-dihydroquinolin-6-yl)carbonyl)-3,4-dihydroquinoxalin-2(1H)-one | 445(M + H) |
| 145 | | N-(2-cyanophenyl)-4-cyclopropyl-1-ethyl-N-methyl-2-oxo-1,2-dihydroquinoline-6-carboxamide | 372(M + H) |
| 146 | | 4-cyclopropyl-1-ethyl-N-(4-fluorophenyl)-N-methyl-2-oxo-1,2-dihydroquinoline-6-carboxamide | 365(M + H) |
| 147 | | 4-cyclopropyl-1-ethyl-N-methyl-2-oxo-N-(4-(trifluoromethyl)phenyl)-1,2-dihydroquinoline-6-carboxamide | 415(M + H) |
| 148 | | 4-cyclopropyl-1-ethyl-N-(2-fluorophenyl)-N-methyl-2-oxo-1,2-dihydroquinoline-6-carboxamide | 365(M + H) |
| 149 | | 4-cyclopropyl-1-ethyl-N-methyl-2-oxo-N-(2-(trifluoromethyl)phenyl)-1,2-dihydroquinoline-6-carboxamide | 415(M + H) |

TABLE 14-continued

| Example No. | Structural Formula | Compound Name | MS |
|---|---|---|---|
| 150 | | 4-cyclopropyl-1-ethyl-N-methyl-N-(2-methylphenyl)-2-oxo-1,2-dihydroquinoline-6-carboxamide | 361(M + H) |
| 151 | | 4-cyclopropyl-1-ethyl-N-methyl-N-(3-methylphenyl)-2-oxo-1,2-dihydroquinoline-6-carboxamide | 361(M + H) |

TABLE 15

| Example No. | Structural Formula | Compound Name | MS |
|---|---|---|---|
| 152 | | 4-cyclopropyl-1-ethyl-N-methyl-N-(4-methylphenyl)-2-oxo-1,2-dihydroquinoline-6-carboxamide | 361(M + H) |
| 153 | | 4-cyclopropyl-1-ethyl-N-(3-fluorophenyl)-N-methyl-2-oxo-1,2-dihydroquinoline-6-carboxamide | 365(M + H) |
| 154 | | N-(3-cyanophenyl)-4-cyclopropyl-1-ethyl-N-methyl-2-oxo-1,2-dihydroquinoline-6-carboxamide | 372(M + H) |

125
126

TABLE 15-continued

| Example No. | Structural Formula | Compound Name | MS |
|---|---|---|---|
| 155 | | N-(4-cyanophenyl)-4-cyclopropyl-1-ethyl-N-methyl-2-oxo-1,2-dihydroquinoline-6-carboxamide | 372(M + H) |
| 156 | | 4-cyclopropyl-1-ethyl-N-methyl-2-oxo-N-(3-(trifluoromethyl)phenyl)-1,2-dihydroquinoline-6-carboxamide | 415(M + H) |
| 157 | | 4-cyclopropyl-1-ethyl-N-methyl-2-oxo-N-(pyridin-2-yl)-1,2-dihydroquinoline-6-carboxamide | 348(M + H) |
| 158 | | 4-cyclopropyl-N-(2,4-difluorophenyl)-1-ethyl-N-methyl-2-oxo-1,2-dihydroquinoline-6-carboxamide | 383(M + H) |
| 159 | | 4-cyclopropyl-1-ethyl-N-methyl-2-oxo-N-(2,4,6-trifluorophenyl)-1,2-dihydroquinoline-6-carboxamide | 401(M + H) |
| 160 | | 4-cyclopropyl-1-ethyl-N-(3-fluoro-4-methylphenyl)-N-methyl-2-oxo-1,2-dihydroquinoline-6-carboxamide | 379(M + H) |

TABLE 15-continued

| Example No. | Structural Formula | Compound Name | MS |
|---|---|---|---|
| 161 | | 4-cyclopropyl-N-(3,4-difluorophenyl)-1-ethyl-N-methyl-2-oxo-1,2-dihydroquinoline-6-carboxamide | 383(M + H) |
| 162 | | 4-cyclopropyl-1-ethyl-N-(4-fluoro-3-methylphenyl)-N-methyl-2-oxo-1,2-dihydroquinoline-6-carboxamide | 379(M + H) |

TABLE 16

| Example No. | Structural Formula | Compound Name | MS |
|---|---|---|---|
| 163 | | 4-cyclopropyl-1-ethyl-N-methyl-2-oxo-N-(pyridin-4-yl)-1,2-dihydroquinoline-6-carboxamide | 348(M + H) |
| 164 | | 4-cyclopropyl-1-ethyl-N-methyl-2-oxo-N-(pyridin-3-yl)-1,2-dihydroquinoline-6-carboxamide | 348(M + H) |
| 165 | | 1-ethyl-N,4-dimethyl-N-(3-methylphenyl)-2-oxo-1,2-dihydroquinoline-6-carboxamide | 335(M + H) |

TABLE 16-continued

| Example No. | Structural Formula | Compound Name | MS |
|---|---|---|---|
| 166 | | 1-ethyl-N,4-dimethyl-N-(4-methylphenyl)-2-oxo-1,2-dihydroquinoline-6-carboxamide | 335(M + H) |
| 167 | | 1-ethyl-4-(1-(2-hydroxyethyl)piperidin-4-yl)-N-methyl-2-oxo-N-phenyl-1,2-dihydroquinoline-6-carboxamide | 434(M + H) |
| 168 | | 1-ethyl-4-(1-(2-methoxyethyl)piperidin-4-yl)-N-methyl-2-oxo-N-phenyl-1,2-dihydroquinoline-6-carboxamide | 448(M + H) |
| 169 | | 4-cyclopropyl-1-ethyl-N-methyl-N-(6-methylpyridin-2-yl)-2-oxo-1,2-dihydroquinoline-6-carboxamide | 362(M + H) |
| 170 | | 4-cyclopropyl-N-(4,6-dimethylpyridin-2-yl)-1-ethyl-N-methyl-2-oxo-1,2-dihydroquinoline-6-carboxamide | 376(M + H) |

TABLE 16-continued

| Example No. | Structural Formula | Compound Name | MS |
|---|---|---|---|
| 171 | | 4-cyclopropyl-1-ethyl-N-methyl-N-(5-methylpyridin-2-yl)-2-oxo-1,2-dihydroquinoline-6-carboxamide | 362(M + H) |
| 172 | | 4-cyclopropyl-1-ethyl-N-methyl-N-(6-methylpyridin-3-yl)-2-oxo-1,2-dihydroquinoline-6-carboxamide | 362(M + H) |

TABLE 17

| Example No. | Structural Formula | Compound Name | MS |
|---|---|---|---|
| 173 | | 4-cyclopropyl-1-ethyl-N-methyl-N-(2-methylpyridin-4-yl)-2-oxo-1,2-dihydroquinoline-6-carboxamide | 362(M + H) |
| 174 | | 1-ethyl-N-methyl-2-oxo-N-phenyl-4-(1-(2,2,2-trifluoroethyl)piperidin-4-yl)-1,2-dihydroquinoline-6-carboxamide | 472(M + H) |
| 175 | | methyl 2-(((4-cyclopropyl-1-ethyl-2-oxo-1,2-dihydroquinolin-6-yl)carbonyl)(methyl)amino)benzoate | 405(M + H) |

TABLE 17-continued

| Example No. | Structural Formula | Compound Name | MS |
|---|---|---|---|
| 176 | | 3-(((4-cyclopropyl-1-ethyl-2-oxo-1,2-dihydroquinolin-6-yl)carbonyl)(methyl)amino)benzoic acid | 391(M + H) |
| 177 | | methyl 4-(((4-cyclopropyl-1-ethyl-2-oxo-1,2-dihydroquinolin-6-yl)carbonyl)(methyl)amino)benzoate | 405(M + H) |
| 178 | | 2-(((4-cyclopropyl-1-ethyl-2-oxo-1,2-dihydroquinolin-6-yl)carbonyl)(methyl)amino)benzoic acid | 391(M + H) |
| 179 | | 1-ethyl-4-(1-(2-hydroxyethyl)piperidin-4-yl)-N-methyl-2-oxo-N-(5,6,7,8-tetrahydronaphthalen-2-yl)-1,2-dihydroquinoline-6-carboxamide | 488(M + H) |

TABLE 17-continued

| Example No. | Structural Formula | Compound Name | MS |
| --- | --- | --- | --- |
| 180 | | 4-(1-benzoylpiperidin-4-yl)-1-ethyl-N-methyl-N-(4-methylphenyl)-2-oxo-1,2-dihydroquinoline-6-carboxamide | 508(M + H) |

TABLE 18

| Example No. | Structural Formula | Compound Name | MS |
| --- | --- | --- | --- |
| 181 | | 1-ethyl-N-methyl-N-(4-methylphenyl)-4-(1-(methylsulfonyl)piperidin-4-yl)-2-oxo-1,2-dihydroquinoline-6-carboxamide | 480(M − H) |
| 182 | | 1-ethyl-N-(2-(hydroxymethyl)-4-methylphenyl)-N-methyl-2-oxo-4-(propan-2-yl)-1,2-dihydroquinoline-6-carboxamide | 393(M + H) |

TABLE 18-continued

| Example No. | Structural Formula | Compound Name | MS |
|---|---|---|---|
| 183 | | 1-ethyl-N-methyl-N-(4-methylphenyl)-4-(1-(2-methylpropanoyl)piperidin-4-yl)-2-oxo-1,2-dihydroquinoline-6-carboxamide | 474(M + H) |
| 184 | | N-(4-chlorophenyl)-1-ethyl-N-methyl-2-oxo-4-(propan-2-yl)-1,2-dihydroquinoline-6-carboxamide | 384(M + H) |
| 185 | | 1-ethyl-N-methyl-N-(4-methyl-3-(phenylcarbamoyl)phenyl)-2-oxo-4-(propan-2-yl)-1,2-dihydroquinoline-6-carboxamide | 480(M − H) |
| 186 | | 1-ethyl-N-methyl-N-(4-methyl-3-(propan-2-ylcarbamoyl)phenyl)-2-oxo-4-(propan-2-yl)-1,2-dihydroquinoline-6-carboxamide | 446(M − H) |
| 187 | | N-(2-dimethylcarbamoyl)-4-methylphenyl)-1-ethyl-N-methyl-2-oxo-4-(propan-2-yl)-1,2-dihydroquinoline-6-carboxamide | 434(M + H) |
| 188 | | 1-ethyl-N-methyl-N-(4-methyl-2-(phenylcarbamoyl)phenyl)-2-oxo-4-(propan-2-yl)-1,2-dihydroquinoline-6-carboxamide | 480(M − H) |

TABLE 18-continued

| Example No. | Structural Formula | Compound Name | MS |
|---|---|---|---|
| 189 | | 1-ethyl-N-methyl-N-(4-methyl-2-(propan-2-ylcarbamoyl)phenyl)-2-oxo-4-(propan-2-yl)-1,2-dihydroquinoline-6-carboxamide | 446(M − H) |

TABLE 19

| Example No. | Structural Formula | Compound Name | MS |
|---|---|---|---|
| 190 | | 1-ethyl-N-methyl-4-(4-methylpiperidin-4-yl)-2-oxo-N-(5,6,7,8-tetrahydronaphthalen-2-yl)-1,2-dihydroquinoline-6-carboxamide | 458(M + H) |
| 191 | | 1-ethyl-4-(1-(2-hydroxyethyl)piperidin-4-yl)-N-methyl-2-oxo-N-(6,7,8,9-tetrahydro-5H-benzo(7)annulen-2-yl)-1,2-dihydroquinoline-6-carboxamide | 502(M + H) |
| 192 | | N-(4-chlorophenyl)-1-ethyl-N-methyl-4-(1-(2-methylpropanoyl)piperidin-4-yl)-2-oxo-1,2-dihydroquinoline-6-carboxamide | 494, 496(M + H) |

TABLE 19-continued

| Example No. | Structural Formula | Compound Name | MS |
|---|---|---|---|
| 193 | | 1-ethyl-N-methyl-4-(1-(2-methylpropanoyl)piperidin-4-yl)-2-oxo-N-(4-(trifluoromethyl)phenyl)-1,2-dihydroquinoline-6-carboxamide | 528(M + H) |
| 194 | | 4-cyano-N-(1-ethyl-2-oxo-4-(propan-2-yl)-1,2-dihydroquinolin-6-yl)-N-methylbenzamide | 374(M + H) |
| 195 | | 1-ethyl-N-(2-methoxy-1-methyl-1H-indol-6-yl)-N-methyl-2-oxo-4-(propan-2-yl)-1,2-dihydroquinoline-6-carboxamide | 430(M − H) |
| 196 | | tert-butyl 6-(((1-ethyl-2-oxo-4-(propan-2-yl)-1,2-dihydroquinolin-6-yl)carbonyl)(methyl)amino)-2,3-dihydro-1H-indole-1-carboxylate | 490(M + H) |
| 197 | | N-(4-chloro-3-(1H-tetrazol-5-yl)phenyl)-1-ethyl-N-methyl-2-oxo-4-(propan-2-yl)-1,2-dihydroquinoline-6-carboxamide | 451(M + H) |

TABLE 20

| Example No. | Structural Formula | Compound Name | MS |
|---|---|---|---|
| 198 | | (2-chloro-5-(((1-ethyl-2-oxo-4-(propan-2-yl)-1,2-dihydroquinolin-6-yl)carbonyl)(methyl)amino)phenyl)acetic acid | 442(M + H) |
| 199 | | N-(4-chloro-3-(2-hydroxyethyl)phenyl)-1-ethyl-N-methyl-2-oxo-4-(propan-2-yl)-1,2-dihydroquinoline-6-carboxamide | 428(M + H) |
| 200 | | 1-ethyl-N-(3-((2-hydroxyethyl)carbamoyl)-4-methylphenyl)-N-methyl-2-oxo-4-(propan-2-yl)-1,2-dihydroquinoline-6-carboxamide | 450(M + H) |
| 201 | | N-(4-chloro-3-methoxyphenyl)-1-ethyl-N-methyl-2-oxo-4-(propan-2-yl)-1,2-dihydroquinoline-6-carboxamide | 414(M + H) |
| 202 | | N-(3-amino-4-chlorophenyl)-1-ethyl-N-methyl-2-oxo-4-(propan-2-yl)-1,2-dihydroquinoline-6-carboxamide | 399(M + H) |
| 203 | | 1-ethyl-N-methyl-N-(4-(methylsulfonyl)phenyl)-2-oxo-4-(propan-2-yl)-1,2-dihydroquinoline-6-carboxamide | 427(M + H) |

TABLE 20-continued

| Example No. | Structural Formula | Compound Name | MS |
|---|---|---|---|
| 204 | | N-(3-(butylcarbamoyl)-4-methylphenyl)-1-ethyl-N-methyl-4-(1-methylpiperidin-4-yl)-2-oxo-1,2-dihydroquinoline-6-carboxamide | 517(M + H) |
| 205 | | 1-ethyl-N-(3-((2-hydroxyethyl)carbamoyl)-4-methylphenyl)-N-methyl-4-(1-methylpiperidin-4-yl)-2-oxo-1,2-dihydroquinoline-6-carboxamide | 505(M + H) |
| 206 | | 1-ethyl-N-methyl-N-(4-methyl-2-(methylcarbamoyl)phenyl)-4-(1-methylpiperidin-4-yl)-2-oxo-1,2-dihydroquinoline-6-carboxamide | 475(M + H) |

TABLE 21

| Example No. | Structural Formula | Compound Name | MS |
|---|---|---|---|
| 207 | | 1-ethyl-N-methyl-4-(1-methylpiperidine-4-yl)-N-(4-methyl-2-(propan-2-ylcarbamoyl)phenyl)-2-oxo-1,2-dihydroquinoline-6-carboxamide | 503(M + H) |

TABLE 21-continued

| Example No. | Structural Formula | Compound Name | MS |
|---|---|---|---|
| 208 | | 1-ethyl-N-(2-((2-hydroxyethyl)carbamoyl)-4-methylphenyl)-N-methyl-4-(1-methylpiperidin-4-yl)-2-oxo-1,2-dihydroquinoline-6-carboxamide | 505(M + H) |
| 209 | | 1-ethyl-N-(3-(2-methoxyethyl)-4-methylphenyl)-N-methyl-4-(1-methylpiperidin-4-yl)-2-oxo-1,2-dihydroquinoline-6-carboxamide | 476(M + H) |
| 210 | | 1-ethyl-N-(3-(2-hydroxyethyl)-4-methylphenyl)-N-methyl-4-(1-methylpiperidin-4-yl)-2-oxo-1,2-dihydroquinoline-6-carboxamide | 462(M + H) |
| 211 | | 1-ethyl-N-methyl-2-oxo-N-phenyl-4-(trifluoromethyl)-1,2-dihydroquinoline-6-carboxamide | 375(M + H) |
| 212 | | 1-ethyl-N-methyl-N-(4-methylphenyl)-2-oxo-4-(trifluoromethyl)-1,2-dihydroquinoline-6-carboxamide | 389(M + H) |

TABLE 21-continued

| Example No. | Structural Formula | Compound Name | MS |
|---|---|---|---|
| 213 | | 1-ethyl-N-(3-fluoro-4-(trifluoromethyl)phenyl)-N-methyl-2-oxo-4-(propan-2-yl)-1,2-dihydroquinoline-6-carboxamide | 435(M + H) |
| 214 | | 1-ethyl-N-methyl-2-oxo-4-(propan-2-yl)-N-(3-(trifluoromethyl)phenyl)-1,2-dihydroquinoline-6-carboxamide | 417(M + H) |
| 215 | | N-(2-cyano-4-methylphenyl)-1-ethyl-N-methyl-2-oxo-4-(propan-2-yl)-1,2-dihydroquinoline-6-carboxamide | 388(M + H) |

TABLE 22

| Example No. | Structural Formula | Compound Name | MS |
|---|---|---|---|
| 216 | | 1-ethyl-N-methyl-N-(6-methylpyridin-3-yl)-2-oxo-4-(tetrahydro-2H-pyran-4-yl)-1,2-dihydroquinoline-6-carboxamide | 406(M + H) |
| 217 | | 1-ethyl-N-methyl-N-(3-methylphenyl)-2-oxo-4-(propan-2-yl)-1,2-dihydroquinoline-6-carboxamide | 363(M + H) |

TABLE 22-continued

| Example No. | Structural Formula | Compound Name | MS |
|---|---|---|---|
| 218 | | 1-ethyl-N-(isoquinolin-6-yl)-N-methyl-2-oxo-4-(propan-2-yl)-1,2-dihydroquinoline-6-carboxamide | 400(M + H) |
| 219 | | N-(4-chloro-2-cyanophenyl)-1-ethyl-N-methyl-2-oxo-4-(propan-2-yl)-1,2-dihydroquinoline-6-carboxamide | 408(M + H) |
| 220 | | 1-ethyl-N-methyl-N-(4-methyl-3-(trifluoromethyl)phenyl)-2-oxo-4-(propan-2-yl)-1,2-dihydroquinoline-6-carboxamide | 431(M + H) |
| 221 | | 1-ethyl-N-methyl-N-(4-methyl-3-(methylsulfonyl)phenyl)-2-oxo-4-(propan-2-yl)-1,2-dihydroquinoline-6-carboxamide | 441(M + H) |
| 222 | | 1-ethyl-N-methyl-N-(3-methyl-4-(methylsulfonyl)phenyl)-2-oxo-4-(propan-2-yl)-1,2-dihydroquinoline-6-carboxamide | 441(M + H) |
| 223 | | 1-ethyl-N-methyl-2-oxo-4-(propan-2-yl)-N-(quinoxalin-6-yl)-1,2-dihydroquinoline-6-carboxamide | 401(M + H) |

TABLE 22-continued

| Example No. | Structural Formula | Compound Name | MS |
|---|---|---|---|
| 224 | | 1-ethyl-N-methyl-2-oxo-4-(propan-2-yl)-N-(quinolin-7-yl)-1,2-dihydroquinoline-6-carboxamide | 400(M + H) |
| 225 | | 1-ethyl-N-methyl-2-oxo-4-(propan-2-yl)-N-(2-(trifluoromethyl)phenyl)-1,2-dihydroquinoline-6-carboxamide | 417(M + H) |

TABLE 23

| Example No. | Structural Formula | Compound Name | MS |
|---|---|---|---|
| 226 | | 1-ethyl-N-methyl-2-oxo-4-(propan-2-yl)-N-(4-(trifluoromethyl)phenyl)-1,2-dihydroquinoline-6-carboxamide | 417(M + H) |
| 227 | | N-(3,4-difluorophenyl)-1-ethyl-N-methyl-2-oxo-4-(propan-2-yl)-1,2-dihydroquinoline-6-carboxamide | 385(M + H) |
| 228 | | 1-ethyl-N-(4-fluoro-3-(trifluoromethyl)phenyl)-N-methyl-2-oxo-4-(propan-2-yl)-1,2-dihydroquinoline-6-carboxamide | 435(M + H) |

TABLE 23-continued

| Example No. | Structural Formula | Compound Name | MS |
|---|---|---|---|
| 229 | | 1-ethyl-N-methyl-2-oxo-N-(3-oxo-2,3-dihydro-1H-isoindol-5-yl)-4-(propan-2-yl)-1,2-dihydroquinoline-6-carboxamide | 404(M + H) |
| 230 | | 1-ethyl-4-(4-hydroxypiperidin-1-yl)-N-methyl-2-oxo-N-(3-(trifluoromethyl)phenyl)-1,2-dihydroquinoline-6-carboxamide | 474(M + H) |
| 231 | | 1-ethyl-N-methyl-N-(2-methyl-3-oxo-2,3-dihydro-1H-isoindol-5-yl)-2-oxo-4-(propan-2-yl)-1,2-dihydroquinoline-6-carboxamide | 418(M + H) |
| 232 | | 1-ethyl-4-(3-hydroxyazetidin-1-yl)-N-methyl-2-oxo-N-(3-(trifluoromethyl)phenyl)-1,2-dihydroquinoline-6-carboxamide | 446(M + H) |
| 233 | | 1-ethyl-4-(4-(2-hydroxyethyl)piperidin-1-yl)-N-methyl-2-oxo-N-(3-(trifluoromethyl)phenyl)-1,2-dihydroquinoline-6-carboxamide | 502(M + H) |

TABLE 23-continued

| Example No. | Structural Formula | Compound Name | MS |
|---|---|---|---|
| 234 | | 4-(dimethylamino)-1-ethyl-N-methyl-2-oxo-N-(3-(trifluoromethyl)phenyl)-1,2-dihydroquinoline-6-carboxamide | 418(M + H) |

TABLE 24

| Example No. | Structural Formula | Compound Name | MS |
|---|---|---|---|
| 235 | | N,1-dimethyl-N-(4-methylphenyl)-4-(1-methylpiperidin-4-yl)-2-oxo-1,2-dihydroquinoline-6-carboxamide | 404(M + H) |
| 236 | | 1-ethyl-4-methyl-6-(2-oxo-5-phenyl-2,3-dihydro-1H-imidazol-1-yl)quinolin-2(1H)-one | 346(M + H) |
| 237 | | 1-ethyl-6-(2-oxo-5-phenyl-2,3-dihydro-1H-imidazol-1-yl)-4-(piperidin-1-yl)quinolin-2(1H)-one | 415(M + H) |
| 238 | | 1-ethyl-4-methyl-6-(3-methyl-2-oxo-5-phenyl-2,3-dihydro-1H-imidazol-1-yl)quinolin-2(1H)-one | 360(M + H) |

TABLE 24-continued

| Example No. | Structural Formula | Compound Name | MS |
|---|---|---|---|
| 239 | | 6-(3-benzyl-2-oxo-5-phenyl-2,3-dihydro-1H-imidazol-1-yl)-1-ethyl-4-methylquinolin-2(1H)-one | 436(M + H) |
| 240 | | 1-ethyl-6-(3-methyl-2-oxo-5-phenyl-2,3-dihydro-1H-imidazol-1-yl)-4-(piperidin-1-yl)quinolin-2(1H)-one | 429(M + H) |
| 241 | | 6-(3-benzyl-2-oxo-5-phenyl-2,3-dihydro-1H-imidazol-1-yl)-1-ethyl-4-(piperidin-1-yl)quinolin-2(1H)-one | 505(M + H) |
| 242 | | 1-ethyl-4-(1-methylpiperidin-4-yl)-6-(2-oxo-5-phenylimidazolidin-1-yl)quinolin-2(1H)-one | 431(M + H) |

TABLE 25

| Example No. | Structural Formula | Compound Name | MS |
|---|---|---|---|
| 243 | | 1-ethyl-4-(1-methyl-1,2,3,6-tetrahydropyridin-4-yl)-6-(2-oxo-5-phenyl-2,3-dihydro-1H-imidazol-1-yl)quinolin-2(1H)-one | 427(M + H) |
| 244 | | 1-ethyl-4-(1-methylpiperidin-4-yl)-6-(2-oxo-5-phenyl-2,3-dihydro-1H-imidazol-1-yl)quinolin-2(1H)-one | 429(M + H) |

EXAMPLE 245

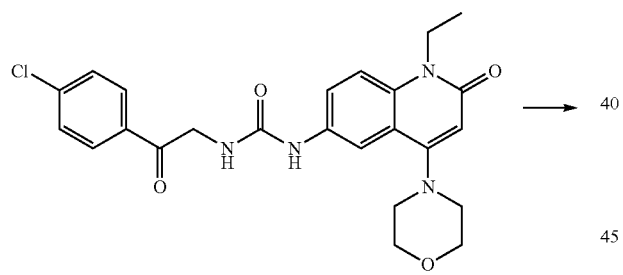

To a suspension of 0.70 g of 1-(2-(4-chlorophenyl)-2-oxoethyl)-3-(1-ethyl-4-(morpholin-4-yl)-2-oxo-1,2-dihydroquinolin-6-yl)urea in 4.0 mL of dioxane was added 4.0 mL of concentrated hydrochloric acid at room temperature and the mixture was stirred for 2 hours. Water was added to the reaction mixture, and the solid matter was filtered and washed with water and diisopropyl ether. The obtained solid matter was purified by silica gel column chromatography [chloroform:methanol gradient elution=100:0 to 90:10]. To the obtained residue was added diisopropyl ether, and the solid matter was filtered to obtain 0.59 g of 6-(5-(4-chlorophenyl)-2-oxo-2,3-dihydro-1H-imidazol-1-yl)-1-ethyl-4-(morpholin-4-yl)quinolin-2(1H)-one as a white solid.

$^1$H-NMR (DMSO-D$_6$) δ: 1.19 (3H, t, J=6.8 Hz), 2.64-2.73 (4H, m), 3.50-3.57 (4H, m), 4.23 (2H, q, J=6.8 Hz), 6.00 (1H, s), 6.95 (1H, s), 7.07-7.13 (2H, m), 7.24 (1H, d, J=2.4 Hz), 7.32-7.38 (2H, m), 7.57 (1H, dd, J=9.1, 2.3 Hz), 7.65 (1H, d, J=9.0 Hz), 10.67 (1H, s).

MS (ESI, m/z):451(M+H), 449(M−H)

EXAMPLE 246

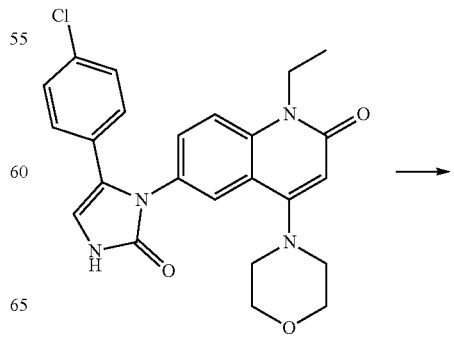

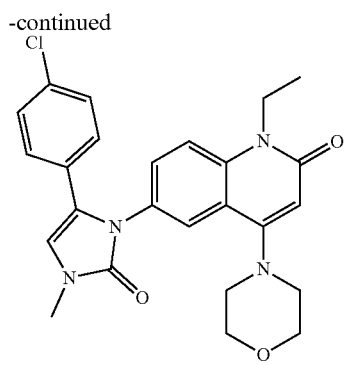

To a solution of 300 mg of 6-(5-(4-chlorophenyl)-2-oxo-2,3-dihydro-1H-imidazol-1-yl)-1-ethyl-4-(morpholin-4-yl)quinolin-2(1H)-one in 3 mL of N,N-dimethylformamide was added under ice cooling 30 mg of 60% sodium hydride and the mixture was stirred for 5 minutes. To the reaction mixture, under ice cooling was added 50 μL of methyl iodide, the mixture was stirred at room temperature for 2 hours. To the reaction mixture were added under ice cooling ethyl acetate and water, and the pH of the mixture was adjusted to 2.0 with 1 mol/L hydrochloric acid, the solid matter was filtered, and washed with water and diisopropyl ether to obtain 203 mg of 6-(5-(4-chlorophenyl)-3-methyl-2-oxo-2,3-dihydro-1H-imidazol-1-yl)-1-ethyl-4-(morpholin-4-yl)quinolin-2(1H)-one as a white solid.

$^1$H-NMR (DMSO-D$_6$) δ: 1.19 (3H, t, J=7.0 Hz), 2.64-2.72 (4H, m), 3.28 (3H, s), 3.50-3.57 (4H, m), 4.23 (2H, q, J=6.8 Hz), 6.01 (1H, s), 7.05-7.12 (2H, m), 7.07 (1H, s), 7.26 (1H, d, J=2.4 Hz), 7.34-7.39 (2H, m), 7.57 (1H, dd, J=9.0, 2.4 Hz), 7.66 (1H, d J=9.0 Hz).

MS (ESI, m/z):465(M+H)

EXAMPLE 247

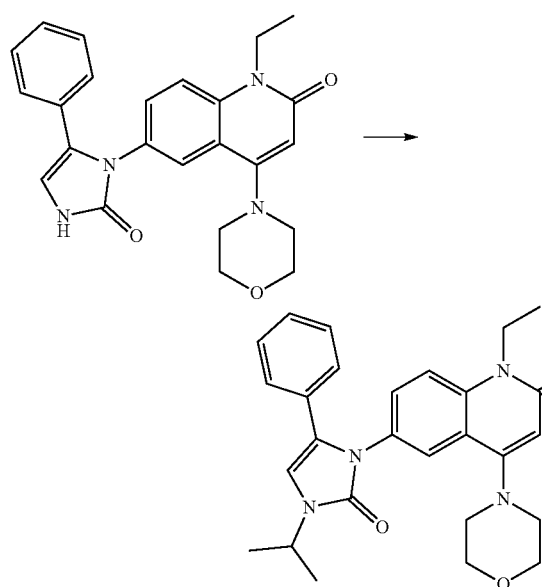

To a suspension of 330 mg of 1-ethyl-4-(morpholin-4-yl)-6-(2-oxo-5-phenyl-2,3-dihydro-1H-imidazol-1-yl)quinolin-2(1H)-one in 2 mL of N,N-dimethylacetamide under ice cooling was added 35 mg of 60% sodium hydride and the mixture was stirred for 5 minutes. To the reaction mixture under ice cooling was added 119 μL of 2-iodopropane, and the mixture was stirred at room temperature for 1 hour. To the reaction mixture was added 60 of 2-iodopropane, and the mixture was stirred at room temperature for 1 hour. To the reaction mixture under ice cooling were added ethyl acetate and water, and the pH of the mixture was adjusted to 2.0 with 1 mol/L hydrochloric acid. The organic layer was fractionated, washed with water and saturated sodium chloride aqueous solution, and then dried over anhydrous magnesium sulfate, and the solvent was distilled off under reduced pressure. The obtained residue was purified by silica gel column chromatography [ethyl acetate to chloroform:methanol gradient elution=95:5 to 90:10]. To the obtained residue were added diisopropyl ether and ethyl acetate, and the solid matter was filtered. The obtained solid matter was purified by silica gel column chromatography [ethyl acetate]. To the obtained residue were added diisopropyl ether and ethyl acetate, and the solid matter was filtered to obtain 68 mg of 1-ethyl-4-(morpholin-4-yl)-6-(2-oxo-5-phenyl-3-(propan-2-yl)-2,3-dihydro-1H-imidazol-1-yl)quinolin-2(1H)-one as a light brown solid.

$^1$H-NMR (CDCl$_3$) δ: 1.36 (3H, t, J=7.1 Hz), 1.43 (6H, d, J=6.8 Hz), 2.63-2.70 (4H, m), 3.55-3.62 (4H, m), 4.32 (2H, q, J=7.2 Hz), 4.55 (1H, quint, J=6.8 Hz), 6.09 (1H, s), 6.51 (1H, s), 7.07-7.12 (2H, m), 7.15-7.28 (3H, m), 7.33 (1H, d, J=2.4 Hz), 7.43 (1H, d, J=9.0 Hz), 7.72 (1H, dd, J=9.0, 2.4 Hz).

EXAMPLE 248

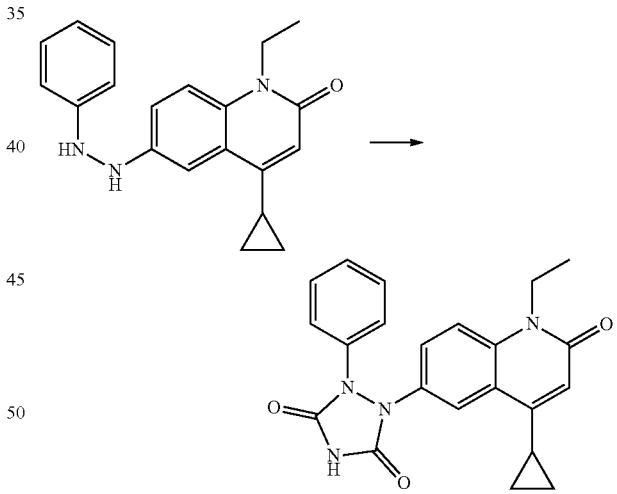

A mixture of 100 mg of 4-cyclopropyl-1-ethyl-6-(2-phenylhydrazinyl)quinolin-2(1H)-one, 46 mg of ethyl carbamoyl carbamate and 3 mL of toluene was stirred at 140° C. for 1 hour and 30 minutes using microwave equipment. The reaction mixture was cooled to room temperature, and then ethyl acetate and water were added. The organic layer was fractionated, washed successively with water and saturated sodium chloride aqueous solution, and then dried over anhydrous magnesium sulfate, and the solvent was distilled off under reduced pressure. The obtained residue was purified by silica gel column chromatography [hexane:ethyl acetate gradient elution=50:50 to 0:100]. To the obtained residue was added chloroform, and the solid matter was filtered to obtain 15 mg of 1-(4-cyclopropyl-1-ethyl-2-oxo-1,2-dihydroquinolin-6-yl)-2-phenyl-1,2,4-triazolidine-3,5-dione as a light brown solid.

$^1$H-NMR (DMSO-D$_6$) δ: 0.57-0.65 (2H, m), 0.92-1.01 (2H, m), 1.14 (3H, t, J=7.0 Hz), 2.03-2.14 (1H, m), 4.20 (2H, q, J=7.1 Hz), 6.29 (1H, s), 7.20-7.27 (1H, m), 7.34-7.47 (4H, m), 7.60 (1H, d, J=9.3 Hz), 7.70 (1H, dd, J=9.1, 2.6 Hz), 8.03 (1H, d, J=2.4 Hz), 12.09 (1H, s).

EXAMPLE 249

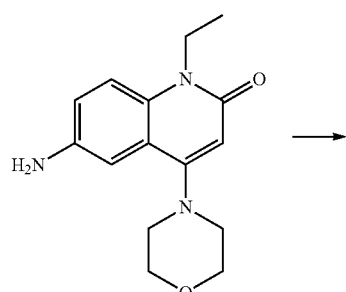

EXAMPLE 250

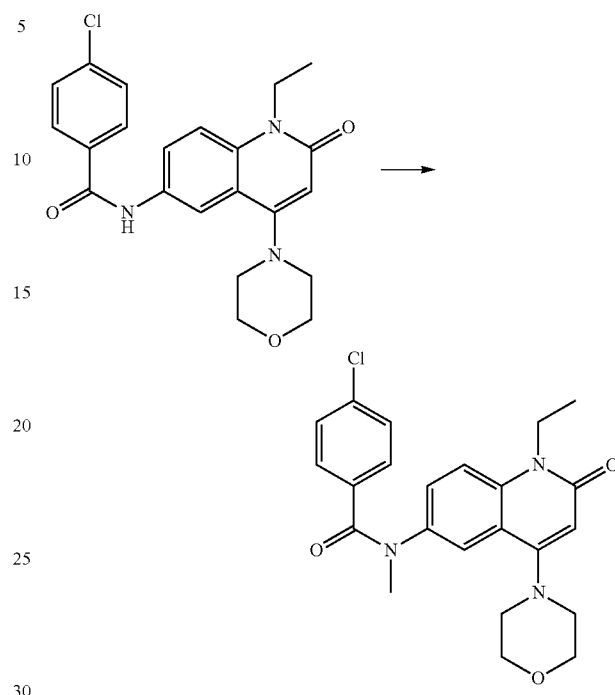

To a suspension of 2.0 g of 6-amino-1-ethyl-4-(morpholin-4-yl)quinolin-2(1H)-one in 10 mL of pyridine under ice cooling was added 1.12 mL of 4-chlorobenzoyl chloride and the mixture was stirred at room temperature for 1 hour. To the reaction mixture under ice cooling were added ethyl acetate and water, and the pH of the mixture was adjusted to 2.0 with 2 mol/L hydrochloric acid. The solid matter was filtered and washed with water and diisopropyl ether to obtain 3.01 g of 4-chloro-N-(1-ethyl-4-(morpholin-4-yl)-2-oxo-1,2-dihydroquinolin-6-yl)benzamide as a white solid.

$^1$H-NMR (DMSO-D$_6$) δ: 1.19 (3H, t, J=7.0 Hz), 3.03-3.13 (4H, m), 3.81-3.90 (4H, m), 4.24 (2H, q, J=7.1 Hz), 6.04 (1H, s), 7.59 (1H, d, J=9.3 Hz), 7.64 (2H, d, J=8.5 Hz), 7.98 (1H, dd, J=9.3, 2.4 Hz), 8.01 (2H, d, J=8.5 Hz), 8.35 (1H, d, J=2.2 Hz), 10.48 (1H, s).

To a suspension of 3.0 g of 4-chloro-N-(1-ethyl-4-(morpholin-4-yl)-2-oxo-1,2-dihydroquinolin-6-yl)benzamide in 24 mL of N,N-dimethylacetamide, 0.35 g of 60% sodium hydride was added under ice cooling and the mixture was stirred for 10 minutes. To the reaction mixture under ice cooling was added 0.68 mL of methyl iodide, the mixture was stirred at room temperature for 1 hour. To the reaction mixture were added ethyl acetate and iced water, and the pH of the mixture was adjusted to 2.0 with 2 mol/L hydrochloric acid. The organic layer was fractionated, washed with water and saturated sodium chloride aqueous solution, and then dried over anhydrous magnesium sulfate, and the solvent was distilled off under reduced pressure. To the obtained residue were added diisopropyl ether and ethyl acetate, the solid matter was filtered, washed with diisopropyl ether to obtain 2.55 g of 4-chloro-N-(1-ethyl-4-(morpholin-4-yl)-2-oxo-1,2-dihydroquinolin-6-yl)-N-methylbenzamide as a white solid.

$^1$H-NMR (DMSO-D$_6$) δ: 1.16 (3H, t, J=7.1 Hz), 2.45-2.60 (4H, m), 3.42 (3H, s), 3.60-3.71 (4H, m), 4.19 (2H, q, J=6.9 Hz), 5.96 (1H, s), 7.21 (1H, s), 7.28 (2H, d, J=8.3 Hz), 7.33 (2H, d, J=8.3 Hz), 7.60 (1H d, J=9.0 Hz), 7.68 (1H, dd, J=9.0, 2.2 Hz).

EXAMPLE 251

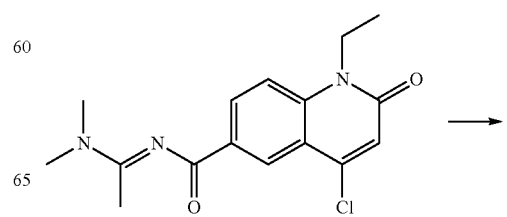

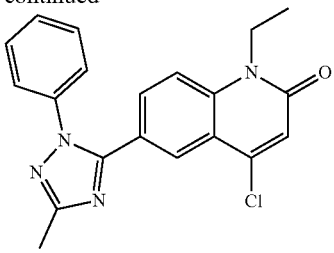

A mixture of 1.5 g of 4-chloro-N-((1E)-1-(dimethylamino)ethylidene)-1-ethyl-2-oxo-1,2-dihydroquinoline-6-carboxamide, 0.51 ml of phenylhydrazine and 12 mL of acetic acid was stirred at the ambient temperature of 120° C. for 2 hours. The reaction mixture was cooled to room temperature and then the solvent was distilled off under reduced pressure. To the obtained residue were added diisopropyl ether and ethyl acetate, and the solid matter was filtered and washed with diisopropyl ether to obtain 1.37 g of 4-chloro-1-ethyl-6-(3-methyl-1-phenyl-1H-1,2,4-(triazol-5-yl)quinolin-2(1H)-one as a light brown solid.

$^1$H-NMR (DMSO-$D_6$) δ: 1.18 (3H, t, J=7.1 Hz), 2.41 (3H, s), 4.25 (2H, q, J=6.9 Hz), 6.97 (1H, s), 7.44-7.58 (5H, m), 7.72 (1H, d, J=9.0 Hz), 7.77 (1H, dd, J=9.0, 2.0 Hz), 7.99 (1H, d, J=2.0 Hz).

EXAMPLE 252

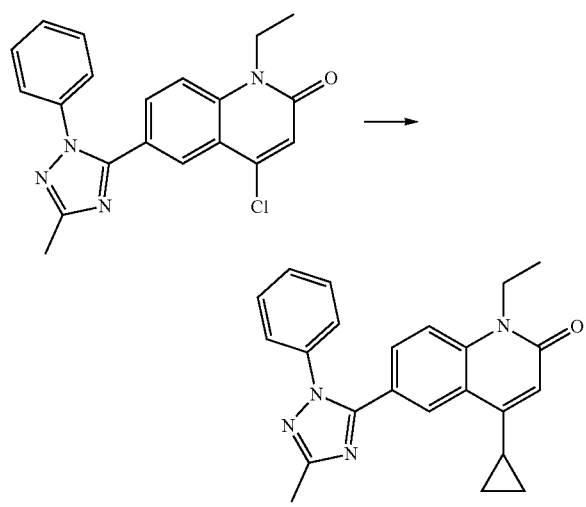

A mixture of 1.37 g of 4-chloro-1-ethyl-6-(3-methyl-1-phenyl-1H-1,2,4-triazol-5-yl)quinolin-2(1H)-one, 0.48 g of cyclopropylboric acid, 1.6 g of tripotassium phosphate, 0.26 g of bis(di-tert-butyl(4-dimethylaminophenyl)phosphine)dichloropalladium(II), 15 mL of dioxane and 3.0 mL of water was stirred under nitrogen atmosphere at the ambient temperature of 100-110° C. for 3 hours. The reaction mixture was cooled to room temperature, and then ethyl acetate and water were added. The organic layer was fractionated, washed successively with water and saturated sodium chloride aqueous solution, and then dried over anhydrous magnesium sulfate, and the solvent was distilled off under reduced pressure. The obtained residue was purified by silica gel column chromatography [hexane:ethyl acetate gradient elution=50:50 to 0:100]. To the obtained residue were added diisopropyl ether and cyclohexane, and the solid matter was filtered to obtain 1.10 g of 4-cyclopropyl-1-ethyl-6-(3-methyl-1-phenyl-1H-1,2,4-(triazol-5-yl)quinolin-2(1H)-one as a slightly brown solid.

$^1$H-NMR (DMSO-$D_6$) δ: 0.54-0.61 (2H, m), 0.70-0.79 (2H, m), 1.17 (3H, t, J=7.1 Hz), 1.70-1.79 (1H, m), 2.40 (3H, s), 4.23 (2H, q, J=7.1 Hz), 6.31 (1H, s), 7.42-7.57 (5H, m), 7.64 (1H, d, J=9.0 Hz), 7.81 (1H, dd, J=8.9, 2.1 Hz), 8.03 (1H, d, J=2.0 Hz).

EXAMPLE 253

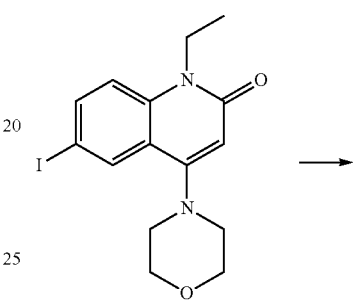

A mixture of 41 mg of 1-ethyl-6-iodo-4-(morpholin-4-yl)quinolin-2(1H)-one, 17 mg of (5S)-5-phenylpyrrolidin-2-one, 1 mg of copper iodide(I), 4 mg of 4,7-dimethoxy-1,10-phenanthroline, 48 mg of cesium carbonate, and 0.5 mL of N-methyl-2-pyrrolidone was stirred at the ambient temperature of 130-135° C. for 30 minutes. The reaction mixture was cooled to room temperature, and then ethyl acetate was added to the reaction mixture, and the insoluble matter was filtered off. To the filtrate were added water and saturated sodium chloride aqueous solution, and the organic layer was fractionated, washed with saturated sodium chloride aqueous solution, and then dried over anhydrous sodium sulfate, and the solvent was distilled off under reduced pressure. The obtained residue was purified by basic silica gel chromatography [hexane:ethyl acetate gradient elution=70:30 to 40:60]. To the obtained residue was added diisopropyl ether, and the solid matter was filtered to obtain 23 mg of 1-ethyl-4-(morpholin-4-yl)-6-((5S)-2-oxo-5-phenylpyrrolidin-1-yl)quinolin-2(1H)-one as a light yellow solid.

$^1$H-NMR (CDCl$_3$) δ: 1.29 (3H, t, J=7.2 Hz), 2.02-2.08 (1H, m), 2.60-2.97 (7H, m), 3.73-3.80 (4H, m), 4.20-4.33 (2H, m), 5.29-5.32 (1H, m), 6.11 (1H, s), 7.23-7.35 (6H, m), 7.75 (1H, d, J=2.4 Hz), 7.81 (1H dd, J=8.8, 2.4 Hz).

EXAMPLE 254

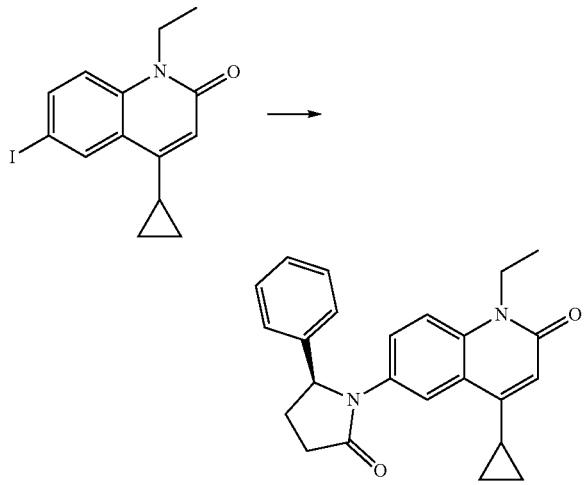

A mixture of 38 mg of 4-cyclopropyl-1-ethyl-6-iodoquinolin-2(1H)-one, 18 mg of (5S)-5-phenylpyrrolidin-2-one, 1 mg of copper iodide(I), 4 mg of 4,7-dimethoxy-1,10-phenanthroline, 51 mg of cesium carbonate, and 0.5 mL of N-methyl-2-pyrrolidone was stirred at the ambient temperature of 130-135° C. for 1 hour and 15 minutes. The reaction mixture was cooled to room temperature, and then ethyl acetate was added to the reaction mixture, and the insoluble matter was filtered off. To the filtrate were added water and saturated sodium chloride aqueous solution, the organic layer was fractionated, washed with saturated sodium chloride aqueous solution, and then dried over anhydrous sodium sulfate, and the solvent was distilled off under reduced pressure. The obtained residue was purified by basic silica gel chromatography [hexane:ethyl acetate gradient elution=80:20 to 60:40] to obtain 22 mg of 4-cyclopropyl-1-ethyl-6-((5S)-2-oxo-5-phenylpyrrolidin-1-yl)quinolin-2(1H)-one as a light yellow solid.

$^1$H-NMR (CDCl$_3$) δ: 0.50-0.57 (1H, m), 0.64-0.71 (1H, m), 0.82-0.99 (2H, m), 1.28 (3H, t, J=7.2 Hz), 1.79-1.86 (1H, m), 2.05-2.12 (1H, m), 2.63-2.85 (3H, m), 4.26 (2H, q, J=7.5 Hz), 5.27-5.30 (1H, m), 6.39 (1H, d, J=1.2 Hz), 7.25-7.40 (6H, m), 7.79 (1H, dd, J=9.2, 2.4 Hz), 7.99 (1H, d, J=2.4 Hz).

EXAMPLE 255

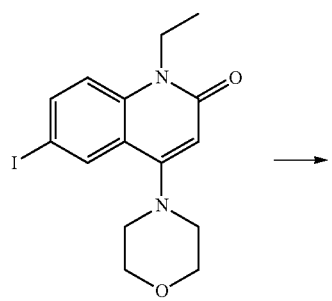

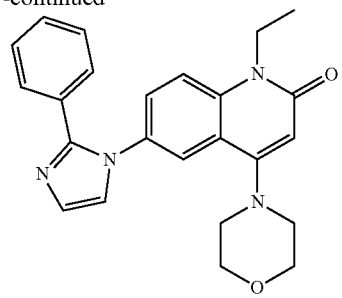

A mixture of 60 mg of 1-ethyl-6-iodo-4-(morpholin-4-yl)quinolin-2(1H)-one, 25 mg of 2-phenyl-1H-imidazole, 1.1 mg of copper oxide(I), 5.6 mg of 4,7-dimethoxy-1,10-phenanthroline, 29 mg of polyethylene glycol, 71 mg of cesium carbonate, and 4 mL of butyronitrile was stirred under nitrogen atmosphere at 170° C. for 40 minutes using microwave equipment. The reaction mixture was cooled to room temperature, and then ethyl acetate and water were added. The organic layer was fractionated, washed with saturated sodium chloride aqueous solution, and then dried over anhydrous sodium sulfate, and the solvent was distilled off under reduced pressure. The obtained residue was purified by thin layer chromatography for fractionation. To the obtained residue was added hexane, and the solid matter was filtered to obtain 10 mg of 1-ethyl-4-(morpholin-4-yl)-6-(2-phenyl-1H-imidazol-1-yl-quinolin-2(1H)-one as a white solid.

$^1$H-NMR (DMSO-D$_6$) δ: 1.20 (3H, t, J=7.3 Hz), 2.57-2.66 (4H, m), 3.42-3.52 (4H, m), 4.26 (2H, q, J=6.8 Hz), 6.03 (1H, s), 7.22 (1H, d, J=1.3 Hz), 7.28-7.38 (6H, m), 7.59 (1H, s), 7.71-7.77 (2H, m).

MS (ESI, m/z):401(M+H)

EXAMPLE 256

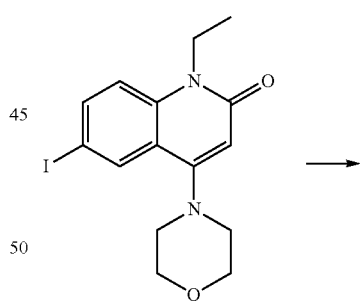

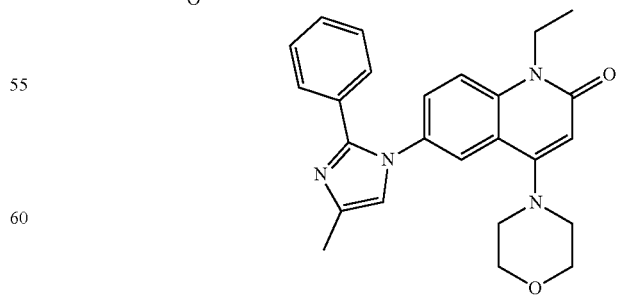

A mixture of 50 mg of 1-ethyl-6-iodo-4-(morpholin-4-yl)quinolin-2(1H)-one, 23 mg of 4-methyl-2-phenyl-1H-imidazole, 1.9 mg of copper oxide(I), 6.2 mg of 4,7-dimethoxy- 1,10-phenanthroline, 25 mg of polyethylene glycol, 64 mg of cesium carbonate, and 1.5 mL of butyronitrile was stirred under nitrogen atmosphere at 210° C. for 45 minutes using microwave equipment. To the reaction mixture was added 1.9 mg of copper oxide(I), and the mixture was stirred at 225° C. for 45 minutes using microwave equipment. To the reaction mixture were added 6.0 mg of copper oxide(I) and 6.2 mg of 4,7-dimethoxy-1,10-phenanthroline, and the mixture was stirred at 230° C. for 1 hour and 30 minutes using microwave equipment. The reaction mixture was cooled to room temperature, and then the insoluble matter was filtered off, and ethyl acetate and water were added. The organic layer was fractionated, washed with saturated sodium chloride aqueous solution, and then dried over anhydrous sodium sulfate, and the solvent was distilled off under reduced pressure. The obtained residue was purified by thin layer chromatography for fractionation. To the obtained residue was added diisopropyl ether, and the solid matter was filtered to obtain 5 mg of 1-ethyl-6-(4-methyl-2-phenyl-1H-imidazol-1-yl)-4-(morpholin-4-yl)quinolin-2(1H)-one as a white solid.

$^1$H-NMR (DMSO-D$_6$) δ: 1.20 (3H, t, J=6.9 Hz), 2.23 (3H, s), 2.56-2.66 (4H, m), 3.41-3.51 (4H, m), 4.20-430 (2H, m), 6.02 (1H, s), 7.22-7.36 (7H, m), 7.67-7.76 (2H, m).

MS (ESI, m/z):415(M+H)

EXAMPLE 257

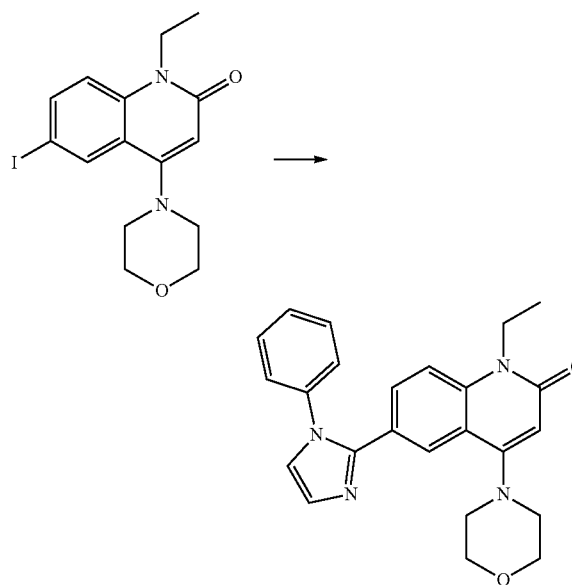

A mixture of 50 mg of 1-ethyl-6-iodo-4-(morpholin-4-yl)quinolin-2(1H)-one, 28 mg of 1-phenyl-1H-imidazole, 50 mg of copper iodide(I), 1.5 mg of palladium acetate, and 2 mL of N,N-dimethylacetamide was stirred under nitrogen atmosphere at 185° C. for 30 minutes using microwave equipment. The mixture was further stirred at 205° C. for 20 minutes. The reaction mixture was cooled to room temperature and then N,N-dimethylacetamide was distilled off under reduced pressure. To the obtained residue was added methanol, and the solid matter was filtered. To the obtained solid matter was added chloroform, and the mixture was heated at reflux for 10 minutes. The reaction mixture was cooled to room temperature, and then the insoluble matter was filtered off. The filtrate was purified by silica gel column chromatography [chloroform:methanol]. To the obtained residue were added hexane and ethyl acetate, and the solid matter was filtered to obtain 10 mg of 1-ethyl-4-(morpholin-4-yl)-6-(1-phenyl-1H-imidazol-2-yl)quinolin-2(1H)-one as a light brown solid.

$^1$H-NMR (DMSO-D$_6$) δ: 1.16 (3H, t, J=6.9 Hz), 2.64-2.73 (4H, m), 3.47-3.57 (4H, m), 4.19 (2H, q, J=7.0 Hz), 5.97 (1H, s), 7.23-7.38 (3H, m), 7.39-7.63 (6H, m), 7.74-7.85 (1H, m).

MS (ESI, m/z):401(M+H)

EXAMPLE 258

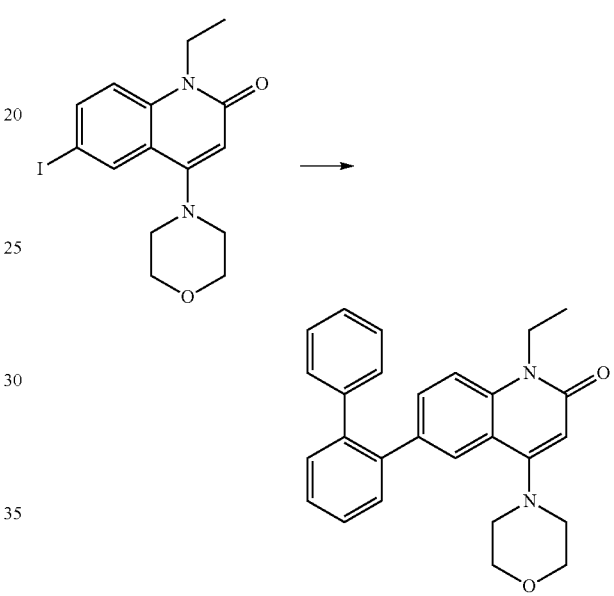

A mixture of 50 mg of 1-ethyl-6-iodo-4-(morpholin-4-yl)quinolin-2(1H)-one, 28 mg of biphenyl-2-ylboronic acid, 6 mg of tris(dibenzylideneacetone)dipalladium(0), 85 ma of cesium carbonate, and 2 mL of dioxane was stirred under nitrogen atmosphere at 150° C. for 30 minutes using microwave equipment. The mixture was further stirred at 160° C. for 30 minutes. The reaction mixture was cooled to room temperature, and then the insoluble matter was filtered off, and the solvent was distilled off under reduced pressure. The obtained residue was purified by silica gel column chromatography [hexane:ethyl acetate]. To the obtained residue were added hexane and ethyl acetate, and the solid matter was filtered to obtain 6 mg of 6-(biphenyl-2-yl)-1-ethyl-4-(morpholin-4-yl)quinolin-2(1H)-one as a white solid.

$^1$H-NMR (DMSO-D$_6$) δ: 1.19 (3H, t, J=6.9 Hz), 2.46-2.55 (4H, m), 3.50-3.58 (4H, m), 4.23 (2H, q, J=7.0 Hz), 5.93 (1H, s), 7.13-7.22 (3H, m), 7.23-7.31 (3H, m), 7.42-7.53 (4H, m), 7.59-7.70 (2H, m).

MS (ESI, m/z):411(M+H)

EXAMPLES 259-276

Confirming to the procedure described in the specification, the compounds indicated in Tables 26-28 were produced by publicly known reactions, such as condensation, addition, oxidization, reduction, rearrangement, substitution, halogenation, dehydration, hydrolysis or the like, or the appropriate combination of these reactions.

TABLE 26

| Example No. | Structural Formula | Compound Name | MS |
|---|---|---|---|
| 259 | | 1-ethyl-4-(morpholin-4-yl)-6-(2-oxo-5-phenyl-3-(2-(piperidin-1-yl)ethyl)-2,3-dihydro-1H-imidazol-1-yl)quinolin-2(1H)-one | 528(M + H) |
| 260 | | 1-ethyl-4-(morpholin-4-yl)-6-(3-(2-(morpholin-4-yl)ethyl)-2-oxo-5-phenyl-2,3-dihydro-1H-imidazol-1-yl)quinolin-2(1H)-one | 530(M + H) |
| 261 | | 6-(3-(2-(dimethylamino)ethyl)-2-oxo-5-phenyl-2,3-dihydro-1H-imidazol-1-yl)-1-ethyl-4-(morpholin-4-yl)quinolin-2(1H)-one | 488(M + H) |
| 262 | | 1-ethyl-6-(3-(2-hydroxyethyl)-2-oxo-5-phenyl-2,3-dihydro-1H-imidazol-1-yl)-4-(morpholin-4-yl)quinolin-2(1H)-one | 461(M + H) |

TABLE 26-continued

| Example No. | Structural Formula | Compound Name | MS |
|---|---|---|---|
| 263 | | 1-ethyl-6-(3-(2-methoxyethyl)-2-oxo-5-phenyl-2,3-dihydro-1H-imidazol-1-yl)-4-(morpholin-4-yl)quinolin-2(1H)-one | 475(M + H) |
| 264 | | 6-(3-butyl-2-oxo-5-pheynyl-2,3-dihydro-1H-imidazazol-1-yl)-1-ethyl-4-(morpholin-4-yl)quinolin-2(1H)-one | 473(M + H) |
| 265 | | 1-ethyl-4-(morpholin-4-yl)-6-(2-oxo-5-phenyl-3-propyl-2,3-dihydro-1H-imidazol-1-yl)quinolin-2(1H)-one | 459(M + H) |
| 266 | | 1-ethyl-6-(3-ethyl-2-oxo-5- phenyl-2,3-dihydro-1H-imidazol-1-yl)-4-(morpholin-4-yl)quinolin-2(1H)-one | 445(M + H) |

TABLE 27

| Example No. | Structural Formula | Compound Name | MS |
| --- | --- | --- | --- |
| 267 | | 4-cyclopropyl-1-ethyl-6-(3-methyl-2-oxo-5-(4-(trifluoromethyl)phenyl)-2,3-dihydro-1H-imidazol-1-yl)quinolin-2(1H)-one | 454(M + H) |
| 268 | | 4-cyclopropyl-1-ethyl-6-(2-oxo-5-(4-(trifluoromethyl)phenyl)-2,3-dihydro-1H-imidazol-1-yl)quinolin-2(1H)-one | 440(M + H) |
| 269 | | 6-(5-(4-chlorophenyl)-3-methyl-2-oxo-2,3-dihydro-1H-imidazol-1-yl)-4-cyclopropyl-1-ethylquinolin-2(1H)-one | 420(M + H) |
| 270 | | 1-ethyl-6-(3-methyl-2-oxo-5-(4-(trifluoromethyl)phenyl)-2,3-dihydro-1H-imidazol-1-yl)-4-(morpholin-4-yl)quinolin-2(1H)-one | 499(M + H) |

TABLE 27-continued

| Example No. | Structural Formula | Compound Name | MS |
|---|---|---|---|
| 271 | | 6-(5-(4-chlorophenyl)-2-oxo-2,3-dihydro-1H-imidazol-1-yl)-cyclopropyl-1-ethylquinolin-2(1H)-one | 406(M + H) |
| 272 | | 1-ethyl-6-(2-oxo-5-(4-(trifluoromethyl)phenyl)-2,3-dihydro-1H-imidazol-1-yl)-4-(morpholin-4-yl)quinolin-2(1H)-one | 485(M + H) |
| 273 | | 1-ethyl-6-(3-methyl-5-(4-methylphenyl)-2-oxo-2,3-dihydro-1H-imidazol-1-yl)-4-(morpholin-4-yl)quinolin-2(1H)-one | 445(M + H) |

TABLE 28

| Example No. | Structural Formula | Compound Name | MS |
|---|---|---|---|
| 274 | | 1-ethyl-6-(5-(4-methylphenyl)-2-oxo-2,3-dihydro-1H-imidazol-1-yl))-4-(morpholin-4-yl)quinolin-2(1H)-one | 431(M + H) |

TABLE 28-continued

| Example No. | Structural Formula | Compound Name | MS |
|---|---|---|---|
| 275 | | 4-cyclopropyl-1-ethyl-6-(3-methyl-5-(4-methylphenyl)-2-oxo-2,3-dihydro-1H-imidazol-1-yl)quinolin-2(1H)-one | 400(M + H) |
| 276 | | 4-cyclopropyl-1-ethyl-6-(5-(4-methylphenyl)-2-oxo-2,3-dihydro-1H-imidazol-1-yl)quinolin-2(1H)-one | 386(M + H) |

EXAMPLE 277

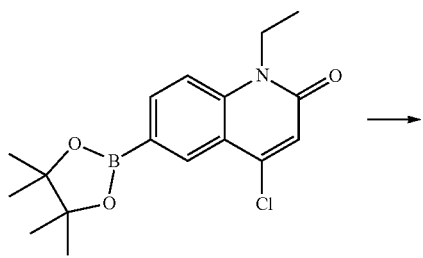

A mixture of 0.17 g of 4-chloro-1-ethyl-6-(4,4,5,5-tetramethyl-1,3,2-dioxaborolan-2-yl)quinolin-2(1H)-one, 0.11 g of 3-bromo-2-phenylpyridine, 0.20 g of tripotassium phosphate, 33 mg of bis(di-tert-butyl(4-dimethylaminophenyl)phosphine)dichloropalladium(II), 6 mL of dioxane and 2 mL of water was stirred under nitrogen atmosphere at the ambient temperature of 100-110° C. for 1 hour. The reaction mixture was cooled to room temperature, and then ethyl acetate and water were added. The organic layer was fractionated, and the aqueous layer was extracted with ethyl acetate. The organic layer was combined with the extract, washed with saturated sodium chloride aqueous solution, and then dried over anhydrous sodium sulfate, and the solvent was distilled off under reduced pressure. The obtained residue was purified by silica gel chromatography [hexane:ethyl acetate gradient elution=100:0 to 60:40] to obtain 134 mg of 4-chloro-1-ethyl-6-(2-phenylpyridin-3-yl)quinolin-2(1H)-one as a white foam.

$^1$H-NMR (CDCl$_3$) δ: 1.33 (3H, t, J=7.1 Hz), 4.31 (2H, q, J=7.1 Hz), 6.89 (1H, s), 7.24-7.29 (3H, m), 7.32-7.42 (5H, m), 7.81 (1H, dd, J=7.6, 1.7 Hz), 7.94 (1H, d, J=2.2 Hz) 8.74 (1H, dd, J=4.8, 1.7 Hz).

EXAMPLE 278

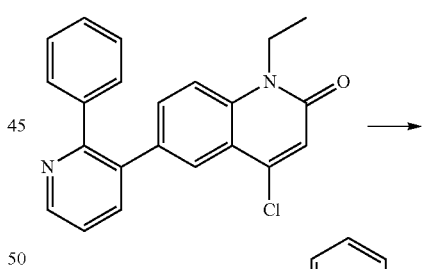

A mixture of 36 mg of 4-chloro-1-ethyl-6-(2-phenylpyridin-3-yl)quinolin-2(1H)-one, 17 mg of cyclopropylboric acid, 43 mg of tripotassium phosphate, 8 mg of bis(di-tert-butyl(4-dimethylaminophenyl)phosphine)dichloropalladium(II), 0.6 mL of dioxane and 0.2 mL of water was stirred at 120° C. for 15 minutes using microwave equipment. The reaction mixture was cooled to room temperature, and then ethyl acetate and water were added. The organic layer was

183 fractionated, and the aqueous layer was extracted with ethyl acetate. The organic layer was combined with the extract, and the solvent was distilled off under reduced pressure. The obtained residue was purified by silica gel chromatography [hexane:ethyl acetate gradient elution=100:0 to 50:50]. To the obtained residue was added hexane, and the solid matter was filtered to obtain 3 mg of 4-cyclopropyl-1-ethyl-6-(2-phenylpyridin-3-yl)quinolin-2(1H)-one as a white solid.

$^1$H-NMR (CDCl$_3$) δ: 0.53-0.59 (2H, m), 0.81-0.92 (2H, m), 1.34 (3H, t, J=7.1 Hz), 1.71-1.80 (1H, m), 4.33 (2H, q, J=7.3 Hz), 6.39-6.44 (1H, m), 7.20-7.49 (8H, m), 7.82 (1H, dd, J=7.6, 1.5 Hz), 7.87 (1H, d, J=2.2 Hz), 8.73 (1H, dd, J=4.6, 1.5 Hz).

EXAMPLE 279

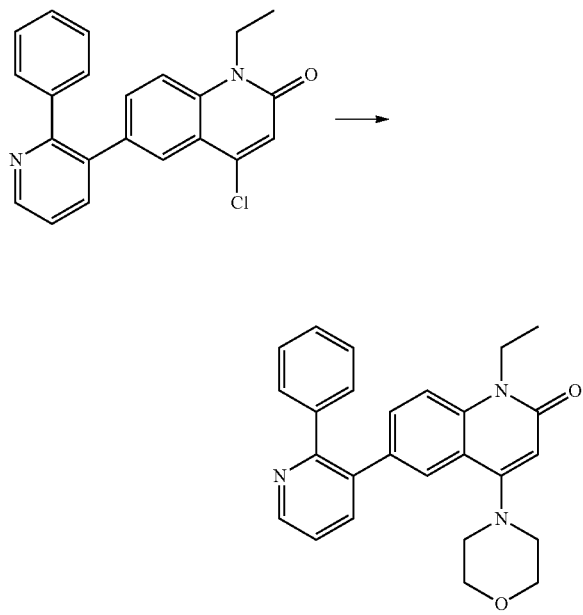

A mixture of 30 mg of 4-chloro-1-ethyl-6-(2-phenylpyridin-3-yl)quinolin-2(1H)-one, 0.7 mL of N,N-dimethylformamide, 35 mg of potassium carbonate and 21.5 μL of morpholine was stirred at 150° C. for 5 minutes using microwave equipment. The mixture was further stirred at 200° C. for 40 minutes. The reaction mixture was cooled to room temperature, and then ethyl acetate and water were added. The organic layer was fractionated, and the aqueous layer was extracted with ethyl acetate. The organic layer was combined with the extract, and the solvent was distilled off under reduced pressure. The obtained residue was purified by silica gel chromatography [hexane:ethyl acetate gradient elution=100:0 to 0:100 to chloroform:methanol=95:5]. To the obtained residue were added hexane and ethyl acetate, and the solid matter was filtered to obtain 8 mg of 1-ethyl-4-(morpholin-4-yl)-6-(2-phenylpyridin-3-yl)quinolin-2 (1H)-one as a brown solid.

$^1$H-NMR (CDCl$_3$) δ: 1.38 (3H, t, J=7.1 Hz), 2.57-2.65 (4H, m), 3.57-3.66 (4H, m), 4.34 (2H, q, J=7.2 Hz), 6.09 (1H, s), 7.20-7.29 (2H, m), 7.35-7.49 (6H, m), 7.61 (1H, dd, J=8.7, 2.1 Hz), 7.74 (1H, dd, J=7.6, 1.7 Hz), 8.73 (1H, dd, J=4.9, 1.7 Hz).

184

EXAMPLE 280

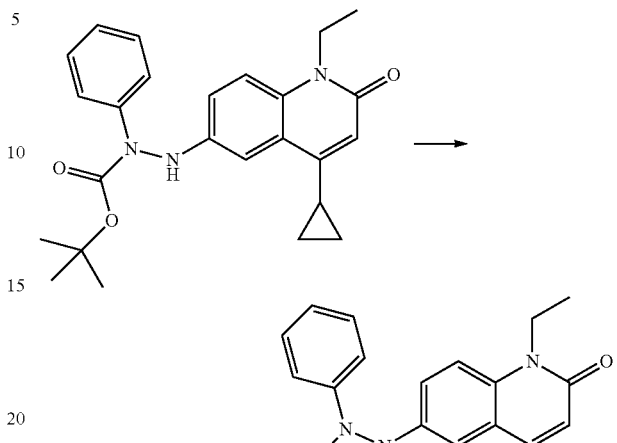

A mixture of 20 mg of tert-butyl 2-(4-cyclopropyl-1-ethyl-2-oxo-1,2-dihydroquinolin-6-yl)-1-phenylhydrazinecarboxylate, 0.5 mL of diethyl methylmalonate and 1 mL of 20% sodium ethoxide-ethanol solution was stirred at 180° C. for 3 minutes using microwave equipment. The reaction mixture was cooled to room temperature, and then ethyl acetate and water were added, and the pH of the mixture was adjusted to 1.0 with 2 mol/L hydrochloric acid. The organic layer was fractionated, and the aqueous layer was extracted with ethyl acetate. The organic layer was combined with the extract, washed with saturated sodium chloride aqueous solution, and then dried over anhydrous magnesium sulfate, and the solvent was distilled off under reduced pressure. The obtained residue was purified by silica gel column chromatography [chloroform:methanol gradient elution=100:0 to 95:5]. To the obtained residue was added ethyl acetate, and the solid matter was filtered to obtain 6 mg of 1-(4-cyclopropyl-1-ethyl-2-oxo-1,2-dihydroquinolin-6-yl)-4-methyl-2-phenylpyrazolidine-3,5-dione as a white solid.

$^1$H-NMR (CDCl$_3$) δ: 0.58-0.65 (2H, m), 0.95-1.03 (2H, m), 1.30 (3H, t, J=7.1 Hz), 1.64 (3H, d, J=7.8 Hz), 1.84-1.94 (1H, m), 3.47 (1H, q, J=7.7 Hz), 4.27 (2H, q, J=7.2 Hz), 6.44 (1H, d, J=1.2 Hz), 7.18-7.24 (1H, m), 7.31-7.39 (5H, m), 7.61 (1H, dd, J=9.1 Hz, 2.6 Hz), 7.94 (1H, d, J=2.4 Hz).

EXAMPLE 281

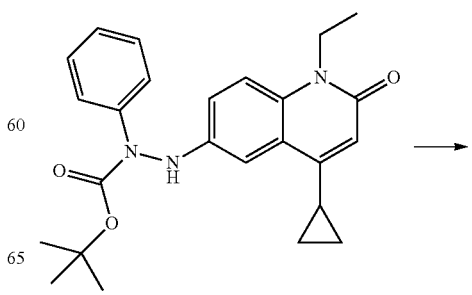

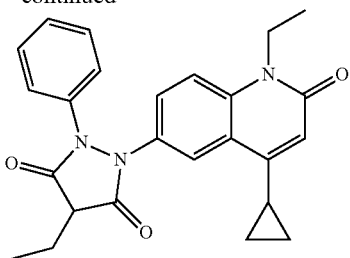

A mixture of 20 mg of tert-butyl 2-(4-cyclopropyl-1-ethyl-2-oxo-1,2-dihydroquinolin-6-yl)-1-phenylhydrazinecarboxylate, 0.5 mL of diethyl diethylmalonate and 1 mL of 20% sodium ethoxide-ethanol solution was stirred at 150° C. for 3 minutes using microwave equipment. The reaction mixture was cooled to room temperature, and then ethyl acetate and water were added, and the pH of the mixture was adjusted to 1.0 with 2 mol/L hydrochloric acid. The organic layer was fractionated, and the aqueous layer was extracted with ethyl acetate. The organic layer was combined with the extract, washed with saturated sodium chloride aqueous solution, and then dried over anhydrous magnesium sulfate, and the solvent was distilled off under reduced pressure. The obtained residue was purified by silica gel column chromatography [chloroform:methanol gradient elution=100:0 to 95:5]. To the obtained residue was added diisopropyl ether, and the solid matter was filtered to obtain 8 mg of 1-(4-cyclopropyl-1-ethyl-2-oxo-1,2-dihydroquinolin-6-yl)-4-ethyl-2-phenylmazolidine-3,5-dione as a light yellow solid.

$^1$H-NMR (CDCl$_3$) δ: 0.58-0.65 (2H, m), 0.95-1.02 (2H, m), 1.10-1.18 (3H, m), 1.30 (3H, t, J=7.2 Hz), 1.85-1.94 (1H, m), 2.15-2.24 (2H, m), 3.42 (1H, t, J=5.5 Hz), 4.27 (2H, q, J=7.2 Hz), 6.42-6.45 (1H, m), 7.18-7.24 (1H, m), 7.31-7.40 (5H, m), 7.61 (1H, dd, J=9.1 Hz, 2.6 Hz), 7.95 (1H, d, J=2.4 Hz).

EXAMPLES 282a, 282b

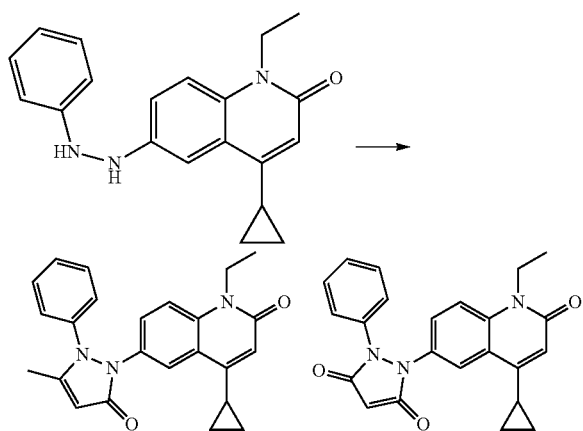

A mixture of 56 mg of 4-cyclopropyl-1-ethyl-6-(2-phenylhydrazinyl)quinolin-2(1H)-one, 14 μL of 4-methylideneoxetan-2-one, 27 μL of triethylamine, and 1 mL of chloroform was heated at reflux for 2 hours. The reaction mixture was cooled to room temperature and then the solvent was distilled off under reduced pressure. The obtained residue was purified by silica gel column chromatography [ethyl acetate:methanol gradient elution=100:0 to 95:5] to obtain 7 mg of a) 4-cyclopropyl-1-ethyl-6-(3-methyl-5-oxo-2-phenyl-2,5-dihydro-1H-pyrazol-1-yl)quinolin-2(1H)-one as a white solid, and 4 mg of b) 4-cyclopropyl-1-ethyl-6-(5-methyl-3-oxo-2-phenyl-2,3-dihydro-1H-pyrazol-1-yl)quinolin-2(1H)-one as a white solid.

a) 4-cyclopropyl-1-ethyl-6-(3-methyl-5-oxo-2-phenyl-2,5-dihydro-1H-pyrazol-1-yl)quinolin-2(1H)-one $^1$H-NMR (CDCl$_3$) δ: 0.63-0.69 (2H, m), 0.99-1.05 (2H, m), 1.28 (3H, t, J=7.2 Hz), 1.91-2.00 (1H, m), 2.12 (3H, d, J=1.0 Hz), 4.26 (2H, q, J=7.0 Hz), 5.61 (1H, d, J=0.7 Hz), 6.40 (1H, d, J=1.0 Hz), 7.21-7.39 (6H, m), 7.71 (1H, dd, J=9.3 Hz, 2.4 Hz), 7.95 (1H, d, J=2.4 Hz).

b) 4-cyclopropyl-1-ethyl-6-(5-methyl-3-oxo-2-phenyl-2,3-dihydro-1H-pyrazol-1-yl)quinolin-2(1H)-one $^1$H-NMR (CDCl$_3$) δ: 0.64-0.70 (2H, m), 1.02-1.09 (2H, m), 1.30 (3H, t, J=7.1 Hz), 1.90-1.99 (1H, m), 2.14 (3H, s), 4.27 (2H, q, J=7.0 Hz), 5.61-5.65 (1H, m), 6.44-6.48 (1H, m), 7.13 (1H, t, J=7.3 Hz), 7.22-7.42 (6H, m), 7.87 (1H, d, J=2.2 Hz).

EXAMPLE 283

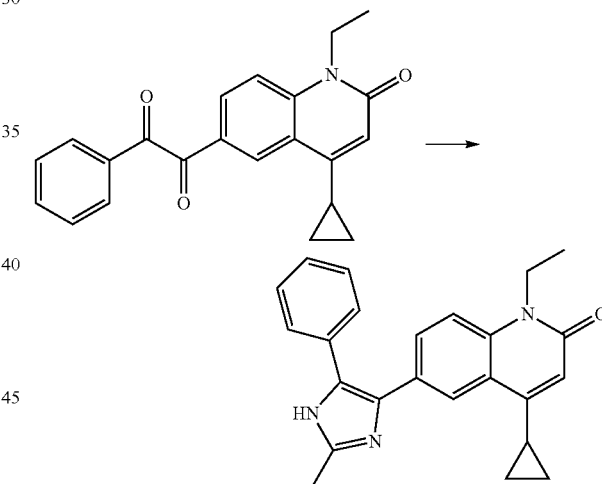

A mixture of 40 mg of 1-(4-cyclopropyl-1-ethyl-2-oxo-1,2-dihydroquinolin-6-yl)-2-phenylethane-1,2-dione, 1 mL of acetic acid, 89 mg of ammonium acetate, and 32 μL of acetaldehyde was stirred at 120° C. for 5 minutes using microwave equipment. The reaction mixture was further stirred at 140° C. for 5 minutes. The reaction mixture was cooled to room temperature, and then ethyl acetate and saturated sodium hydrogen carbonate aqueous solution were added. The organic layer was fractionated, and the aqueous layer was extracted with ethyl acetate. The organic layer was combined with the extract, washed with saturated sodium chloride aqueous solution, and then dried over anhydrous magnesium sulfate, and the solvent was distilled off under reduced pressure. The obtained residue was purified by silica gel chromatography [ethyl acetate:methanol gradient elution=100:0 to 90:10]. To the obtained residue was added diisopropyl ether, and the solid matter was filtered to obtain 4.7 mg of 4-cyclopropyl-1-ethyl-6-(2-methyl-5-phenyl-1H-imidazol-4-yl)quinolin-2(1H)-one as a white solid.

$^1$H-NMR (CDCl$_3$) δ: 0.59-0.67 (2H, m), 0.75-0.85 (2H, m), 1.34 (3H, t, J=7.2 Hz), 1.79-1.90 (1H, m), 2.55 (3H, s), 4.33 (2H, q, J=7.2 Hz), 6.36-6.42 (1H, m), 6.72 (1H, s), 7.20-7.41 (4H, m), 7.42-7.55 (1H, m), 7.75-7.79 (1H, m), 8.19-8.26 (1H, m).

EXAMPLE 284

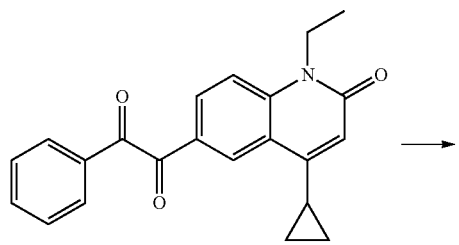

EXAMPLE 285

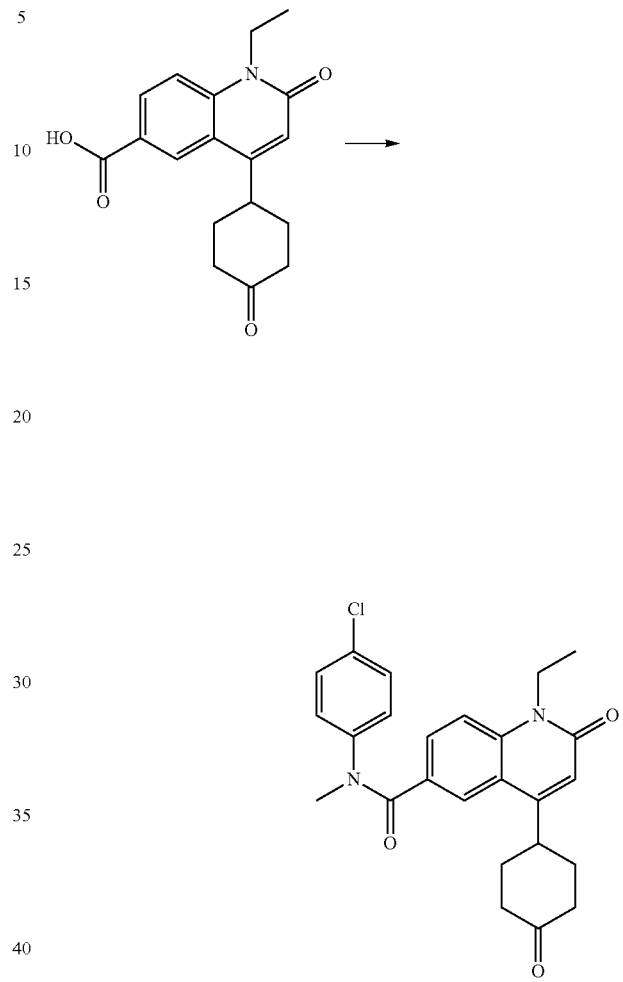

A mixture of 27 mg of 1-(4-cyclopropyl-1-ethyl-2-oxo-1,2-dihydroquinolin-6-yl)-2-phenylethane-1,2-dione and 1 mL of polyethylene glycol 400 was stirred at 100° C. for 5 minutes using microwave equipment. To the reaction mixture was added 5.2 μL of ethan-1,2-diamine, and the mixture was stirred at 150° C. for 7 minutes using microwave equipment. The reaction mixture was further stirred at 160° C. for 10 minutes. The reaction mixture was cooled to room temperature, and then ethyl acetate and water were added. The organic layer was fractionated, washed with water and saturated sodium chloride aqueous solution, and then dried over anhydrous magnesium sulfate, and the solvent was distilled off under reduced pressure. The obtained residue was purified by silica gel chromatography [hexane:ethyl acetate gradient elution=50:50 to 0:100]. To the obtained residue was added diisopropyl ether, and the solid matter was filtered to obtain 2 mg of 4-cyclopropyl-1-ethyl-6-(3-phenylpyradin-2-yl)quinolin-2(1H)-one as a white solid.

$^1$H-NMR (CDCl$_3$) δ: 0.52-0.58 (2H, m), 0.77-0.85 (2H, m), 1.34 (3H, t, J=7.2 Hz), 1.65-1.75 (1H, m), 4.33 (2H, q, J=7.2 Hz), 6.37-6.41 (1H, m), 7.31-7.41 (4H, m), 7.47-7.54 (2H, m), 7.86 (1H, dd, J=8.9 Hz, 2.1 Hz), 8.13 (1H, d, J=2.2 Hz), 8.63 (2H, dd, J=6.8 Hz, 2.4 Hz).

To a suspension of 134 mg of 1-ethyl-2-oxo-4-(4-oxocyclohexyl)-1,2-dihydroquinoline-6-carboxylic acid in 5 mL of dichloromethane were added 72 mg of 4-chloro-N-methylaniline, 0.27 mL of triethylamine and 216 mg of bis(2-oxo-3-oxazolidinyl)phosphinic acid chloride, and the mixture was stirred at room temperature for 9 hours. To the reaction mixture were added 72 mg of N-methyl-4-chloroaniline, 0.27 mL of triethylamine and 216 mg of bis(2-oxo-3-oxazolidinyl)phosphinic acid chloride, and the mixture was stirred at room temperature for 15 hours. The obtained reaction mixture was subjected to solvent elimination by distillation under reduced pressure. The obtained residue was purified by silica gel column chromatography [ethyl acetate]. To the obtained residue were added diisopropyl ether and ethyl acetate, the solid matter was filtered to obtain 73 mg of N-(4-chlorophenyl)-1-ethyl-N-methyl-2-oxo-4-(4-oxocyclohexyl)-1,2-dihydroquinoline-6-carboxamide as a white solid.

$^1$H-NMR (CDCl$_3$) δ: 1.32 (3H, t, J=7.2 Hz), 1.74-1.88 (2H, m), 1.95-2.04 (2H, m), 2.42-2.61 (4H, m), 3.07-3.17 (1H, m), 3.55 (3H, s), 4.30 (2H, q, J=7.1 Hz), 6.55-6.58 (1H, m), 7.03 (2H, d, J=8.8 Hz), 7.22-7.33 (3H, m), 7.66 (1H, dd, J=8.9 Hz, 2.1 Hz), 7.71 (1H, d, J=1.7 Hz).

EXAMPLE 286

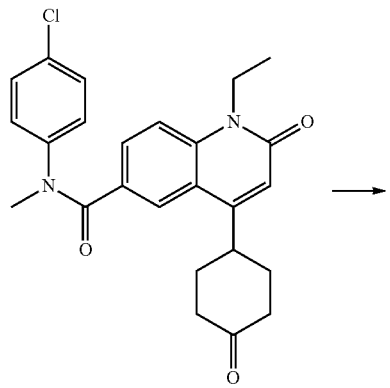

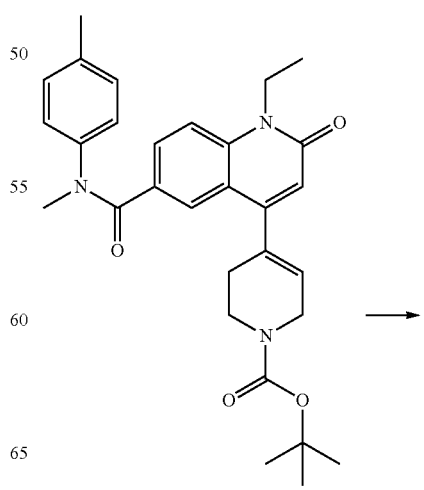

A mixture of 51 mg of N-(4-chlorophenyl)-1-ethyl-N-methyl-2-oxo-4-(4-oxocyclohexyl)-1,2-dihydroquinoline-6-carboxamide, 8.8 mg of sodium borohydride, and 1.0 mL of methanol was stirred at room temperature for 1 hour. To the reaction mixture were added ethyl acetate and 1 mol/L hydrochloric acid. The organic layer was fractionated, and the aqueous layer was extracted with ethyl acetate. The organic layer was combined with the extract, washed with saturated sodium chloride aqueous solution, and then dried over anhydrous magnesium sulfate, and the solvent was distilled off under reduced pressure. The obtained residue was purified by silica gel column chromatography [ethyl acetate:methanol gradient elution=100:0 to 90:10]. To the obtained residue was added diisopropyl ether, and the solid matter was filtered to obtain 41 mg of N-(4-chlorophenyl)-1-ethyl-4-(4-hydroxycyclohexyl)-N-methyl-2-oxo-1,2-dihydroquinoline-6-carboxamide as a white solid.

$^1$H-NMR (CDCl$_3$) δ: 1.32 (3H, t, J=7.2 Hz), 1.36-1.70 (6H, m), 2.09-2.20 (2H, m), 2.50-2.61 (1H, m), 3.54 (3H, s), 3.60-3.75 (1H, m), 4.29 (2H, q, J=7.0 Hz), 6.51-6.55 (1H, m), 7.02 (2H, d, J=8.8 Hz), 7.20-7.35 (3H, m), 7.55 (1H, d, J=2.0 Hz), 7.72 (1H, dd, J=8.8 Hz, 2.0 Hz).

EXAMPLE 287

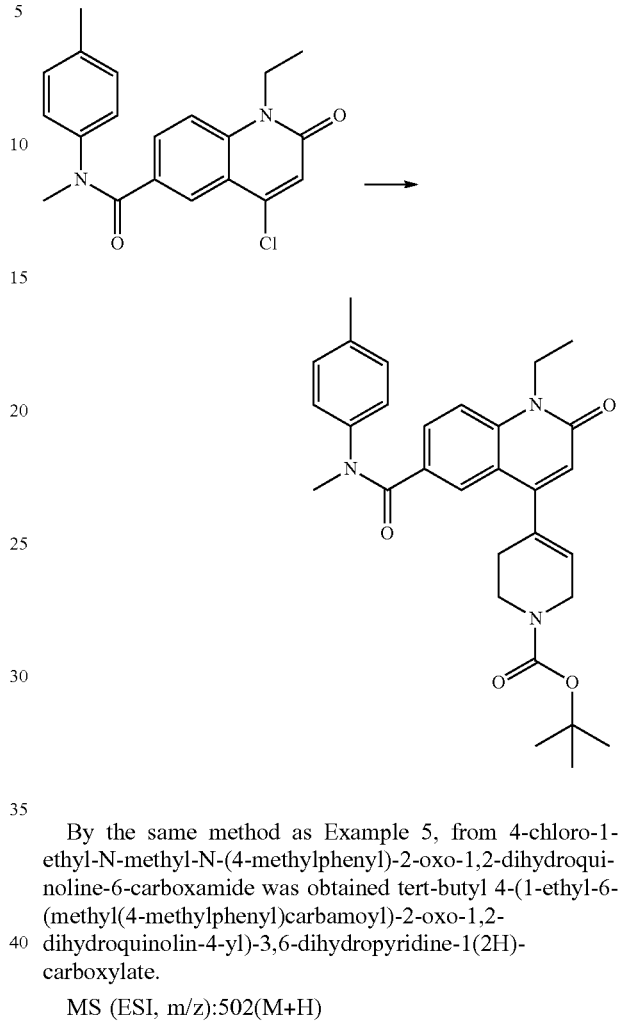

By the same method as Example 5, from 4-chloro-1-ethyl-N-methyl-N-(4-methylphenyl)-2-oxo-1,2-dihydroquinoline-6-carboxamide was obtained tert-butyl 4-(1-ethyl-6-(methyl(4-methylphenyl)carbamoyl)-2-oxo-1,2-dihydroquinolin-4-yl)-3,6-dihydropyridine-1(2H)-carboxylate.

MS (ESI, m/z):502(M+H)

EXAMPLE 288

-continued

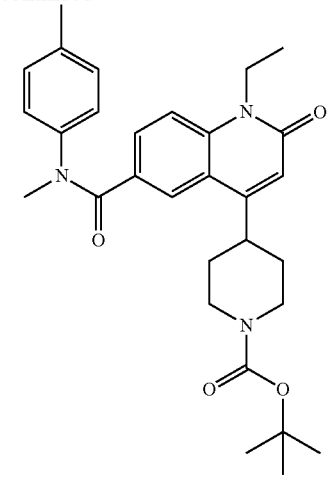

By the same method as Example 6, from tert-butyl 4-(1-ethyl-6-(methyl(4-methylphenyl)carbamoyl)-2-oxo-1,2-dihydroquinolin-4-yl)-3,6-dihydropyridine-1(2H)-carboxylate was obtained tert-butyl 4-(1-ethyl-6-(methyl(4-methylphenyl)carbamoyl)-2-oxo-1,2-dihydroquinolin-4-yl)piperidine-1-carboxylate.
MS (ESI, m/z):504(M+H)

EXAMPLE 289

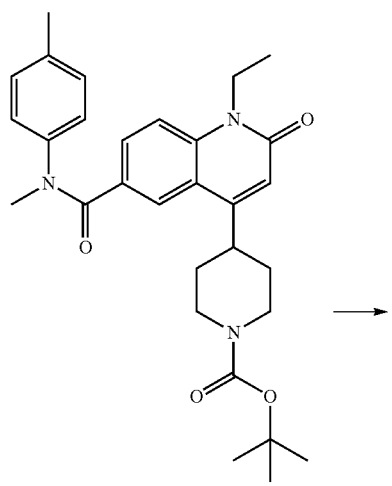

By the same method as Example 7, from tert-butyl 4-(1-ethyl-6-(methyl(4-methylphenyl)carbamoyl)-2-oxo-1, 2-dihydroquinolin-4-yl)piperidine-1-carboxylate was obtained 1-ethyl-N-methyl-N-(4-methylphenyl)-2-oxo-4-piperidin-4-yl)-1,2-dihydroquinoline-6-carboxamide.
MS (ESI, m/z):404(M+H)

EXAMPLE 290

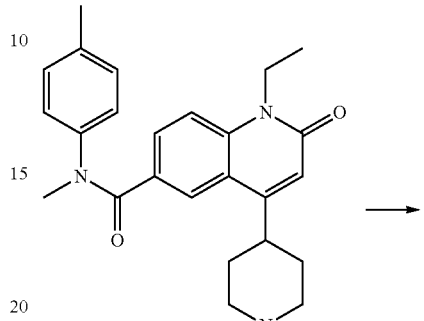

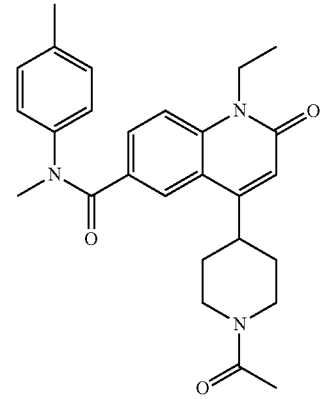

A mixture of 50 mg of 1-ethyl-N-methyl-N-(4-methylphenyl)-2-oxo-4-(piperidin-4-yl)-1,2-dihydroquinoline-6-carboxamide, 20 μL of acetyl chloride, 0.1 mL of triethylamine, and 1 mL of dichloromethane was stirred at room temperature for 20 minutes. The reaction mixture was purified by silica gel column chromatography [chloroform:methanol gradient elution=100:0 to 80:20]. To the obtained residue were added hexane and ethyl acetate, and the solid matter was filtered to obtain 13 mg of 4-(1-acetylpiperidin-4-yl)-1-ethyl-N-methyl-N-(4-methylphenyl)-2-oxo-1,2-dihydroquinoline-6-carboxamide as a yellow solid.
$^1$H-NMR (DMSO-D$_6$) δ: 1.12-1.55 (7H, m), 2.05 (3H, s), 2.20 (3H, s), 2.57-2.69 (1H, m), 2.86-2.99 (1H, m), 3.10-3.23 (1H, m), 3.40 (3H, s), 3.87 (1H, d, J=13.9 Hz), 4.20 (2H, q, J=6.9 Hz), 4.49 (1H, d, J=12.9 Hz), 6.37 (1H, s), 7.06-7.13 (4H, m), 7.52-7.62 (2H, m), 7.74 (1H, d J=8.8 Hz).

EXAMPLE 291

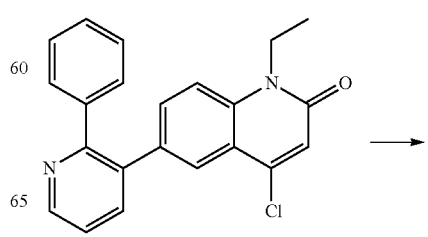

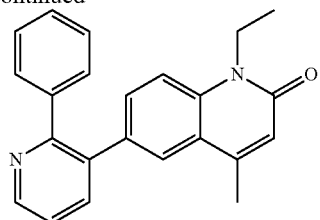

A mixture of 30 mg of 4-chloro-1-ethyl-6-(2-phenylpyridin-3-yl)quinolin-2(1H)-one, 10 mg of methylboric acid, 35 mg of tripotassium phosphate, 6 mg of bis(di-tert-butyl(4-dimethylaminophenyl)phosphine)dichloropalladium(II), 0.5 mL of dioxane and 0.2 mL of water was stirred at 120° C. for 10 minutes using microwave equipment. The reaction mixture was cooled to room temperature. The reaction mixture was purified by silica gel chromatography [hexane: ethyl acetate gradient elution=100:0 to 30:70]. To the obtained residue was added hexane, and the solid matter was filtered to obtain 5 mg of 1-ethyl-4-methyl-6-(2-phenylpyridin-3-yl)quinolin-2(1H)-one as a white solid.

$^1$H-NMR (CDCl$_3$) δ: 1.34 (3H, t, J=7.3 Hz), 2.21 (3H, d, J=1.0 Hz), 4.33 (2H, q, J=7.3 Hz), 6.55 (1H, d, J=0.96 Hz), 7.23-7.32 (4H, m), 7.34-7.42 (4H, m), 7.48 (1H, d, J=1.9 Hz), 7.81 (1H, dd, J=7.8, 1.7 Hz), 8.73 (1H, dd, J=4.9, 1.7 Hz).

MS (ESI, m/z):341(M+H)

EXAMPLES 292-294

Confirming to the procedure described in the specification, the compounds indicated in Table 29 were produced by publicly known reactions, such as condensation, addition, oxidization, reduction, rearrangement, substitution, halogenation, dehydration, hydrolysis or the like, or the appropriate combination of these reactions.

TABLE 29

| Example No. | Structural Formula | Compound Name | MS |
|---|---|---|---|
| 292 | | 1-ethyl-N-(3-fluoro-4-methylphenyl)-N-methyl-4-(1-methylpiperidin-4-yl)-2-oxo-1,2-dihydroquinoline-6-carboxamide | 436(M + H) |
| 293 | | N-(3-chloro-4-methylphenyl)-1-ethyl-N-methyl-4-(1-methylpiperidin-4-yl)-2-oxo-1,2-dihydroquinoline-6-carboxamide | 452(M + H) |
| 294 | | N-(3,4-dimethylphenyl)-1-ethyl-N-methyl-4-(1-methylpiperidin-4-yl)-2-oxo-1,2-dihydroquinoline-6-carboxamide | 432(M + H) |

TEST EXAMPLE 1

(CXCL10 Production Inhibition Test)

$0.5 \times 10^4$ or $1 \times 10^4$ human umbilical vein-derived endothelial cells were suspended in 100 μL of an EGM-2 BulletKit medium (without GA) or a Medium-200 medium supplemented with an EGM-2 SingleQuots kit (without GA), inoculated to a 96-well plate and cultured overnight. 100 μL of a solution of each test compound diluted with the same medium as that used in the inoculation was added to the cultured cells (final concentration of the test compound: 0.1 μmol/L). 1 hour thereafter, TNFα was added thereto at a final concentration of 10 ng/mL. 72 hours after the stimulation, the supernatant was recovered, and the amount of CXCL10 produced in the culture supernatant was determined using an ELISA kit (Peprotech, 900-109).

The rate of inhibition was calculated according to the following expression:

Rate of inhibition (%)=100−(Amount of CXCL10 produced in the presence of the test compound/ Amount of CXCL10 produced in the absence of the test compound)×100

The compounds of Example 2, Example 3, Example 8, Example 11, Example 14, Example 16, Example 17, Examples 245 to 248, Example 250, Examples 252 to 276, Examples 278 to 281, Example 282a, Example 282b, Example 283, Example 284, Example 286 and Examples 290 to 294 inhibited 50% or more of CXCL10 production at 0.1 μmol/L.

The compound of the present invention exhibited an excellent CXCL10 production inhibitory effect.

INDUSTRIAL APPLICABILITY

The compound represented by the general formula [1] or the salt thereof has an excellent CXCL10 inhibitory activity and is useful as an agent for treatment such as prophylaxis and/or therapy of a disease involving the overproduction of CXCL10.

The invention claimed is:

1. A compound represented by the general formula [1] or a salt thereof:

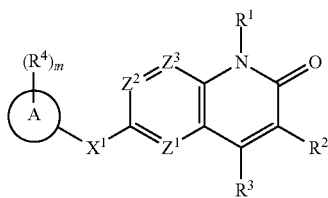

[1]

wherein $R^1$ represents an optionally substituted $C_{1-6}$ alkyl group;

$R^2$ represents a hydrogen atom, a halogen atom or an optionally substituted $C_{1-6}$ alkyl group;

$R^3$ represents a halogen atom, an optionally substituted $C_{1-6}$ alkyl group, an optionally substituted $C_{2-6}$ alkenyl group, an optionally substituted $C_{3-8}$ cycloalkyl group, an optionally substituted $C_{4-8}$ cycloalkenyl group, an optionally substituted aryl group, an optionally substituted $C_{1-6}$ alkoxy group, an optionally substituted $C_{1-6}$ alkylamino group, an optionally substituted di($C_{1-6}$ alkyl)amino group or an optionally substituted heterocyclic group;

$Z^1$, $Z^2$ and $Z^3$ are the same or different and each represent a nitrogen atom or a group represented by the general formula $CR^5$ wherein $R^5$ represents a hydrogen atom, a halogen atom or an optionally substituted $C_{1-6}$ alkyl group;

$X^1$ represents (1) a group represented by the general formula $C(=O)N(R^6)$ wherein the carbon atom is bonded to ring A, and $R^6$ represents a hydrogen atom, an amino-protective group or an optionally substituted $C_{1-6}$ alkyl group, (2) a group represented by the general formula $N(R^7)C(=O)$ wherein the nitrogen atom is bonded to ring A, and $R^7$ represents a hydrogen atom, an amino-protective group or an optionally substituted $C_{1-6}$ alkyl group; or $R^7$ represents, together with one substituent $R^4$ on ring A, an optionally substituted $C_{2-4}$ alkylene group, a group represented by the general formula $O-Y^1$ wherein the oxygen atom is bonded to ring A, and $Y^1$ represents an optionally substituted $C_{1-3}$ alkylene group, a group represented by the general formula $S(O)_n-Y^2$ wherein the sulfur atom is bonded to ring A, $Y^2$ represents an optionally substituted $C_{1-3}$ alkylene group, and n represents an integer of 0 to 2, or a group represented by the general formula $N(R^8)-Y^3$ wherein the nitrogen atom is bonded to ring A, $Y^3$ represents an optionally substituted $C_{1-3}$ alkylene group, and $R^8$ represents a hydrogen atom, an amino-protective group, an optionally substituted $C_{1-6}$ alkyl group or an optionally substituted aryl group, (3) an optionally substituted divalent cyclic hydrocarbon group resulting from the removal of one hydrogen atom from each of two adjacent atoms or (4) an optionally substituted divalent heterocyclic group resulting from the removal of one hydrogen atom from each of two adjacent atoms;

ring A represents a cyclic hydrocarbon group or a heterocyclic group;

m number of $R^4$ are the same or different and each represent a halogen atom, a cyano group, a nitro group, an amino-protective group, an optionally substituted $C_{1-6}$ alkyl group, an optionally substituted $C_{2-6}$ alkenyl group, an optionally substituted $C_{2-6}$ alkynyl group, an optionally substituted $C_{3-8}$ cycloalkyl group, an optionally substituted $C_{4-8}$ cycloalkenyl group, an optionally substituted aryl group, an optionally substituted $C_{1-6}$ alkoxy group, an optionally substituted aryloxy group, an optionally substituted $C_{1-6}$ alkylamino group, an optionally substituted di($C_{1-6}$ alkyl)amino group, an optionally substituted arylamino group, an optionally substituted carbamoyl group, an optionally substituted sulfamoyl group, an optionally substituted $C_{1-6}$ alkylthio group, an optionally substituted arylthio group, an optionally substituted $C_{1-6}$ alkylsulfonyl group, an optionally substituted arylsulfonyl group, an optionally substituted heterocyclic group, an optionally protected amino group, an optionally protected hydroxyl group, an optionally protected carboxyl group, an optionally substituted $C_{2-5}$ alkylene group formed together by two adjacent $R^4$, an optionally substituted $C_{2-4}$ alkylene group formed together by one $R^4$ and $R^7$, a group represented by the general formula $O-Y^1$ formed together by one $R^4$ and $R^7$ wherein the oxygen atom is bonded to ring A, and $Y^1$ represents an optionally substituted $C_{1-3}$ alkylene group, a group represented by the general formula $S(O)_n-Y^2$ formed together by one $R^4$ and $R^7$ wherein the sulfur atom is bonded to ring A, $Y^2$ represents an optionally substituted $C_{1-3}$ alkylene group, and n represents an integer of 0 to 2, or a group represented by the general formula $N(R^8)$—$Y^3$ formed together by one $R^4$ and $R^7$ wherein the nitrogen atom is bonded to ring A, $Y^3$ represents an optionally substituted $C_{1-3}$ alkylene group, and $R^8$ represents a hydrogen atom, an amino-protective group, an optionally substituted $C_{1-6}$ alkyl group or an optionally substituted aryl group; and m represents an integer of 0 to 5.

2. The compound according to claim 1 or a salt thereof, wherein $R^2$ is a hydrogen atom or an optionally substituted $C_{1-6}$ alkyl group; and each of $Z^1$, $Z^2$ and $Z^3$ is CH.

3. The compound according to claim 1 or a salt thereof, wherein $R^1$ is a $C_{1-3}$ alkyl group, and $R^3$ is an optionally substituted $C_{1-6}$ alkyl group, an optionally substituted $C_{3-8}$ cycloalkyl group, an optionally substituted aryl group or an optionally substituted heterocyclic group.

4. The compound according to claim 1 or a salt thereof, wherein ring A is a cyclic hydrocarbon group.

5. The compound according to claim 1 or a salt thereof, wherein $X^1$ is a group represented by the general formula $C(=O)N(R^6)$ wherein the carbon atom is bonded to ring A, and $R^6$ represents a hydrogen atom, an amino-protective group or an optionally substituted $C_{1-6}$ alkyl group.

6. The compound according to claim 1 or a salt thereof, wherein $X^1$ is a group represented by the general formula $C(=O)N(R^{6a})$ wherein the carbon atom is bonded to ring A, and $R^{6a}$ represents a hydrogen atom or an optionally substituted $C_{1-3}$ alkyl group;

m number of $R^4$ are the same or different and each are a halogen atom, an optionally substituted $C_{1-3}$ alkyl group, an optionally substituted $C_{1-3}$ alkylamino group or an optionally protected amino group; and m is an integer of 0 to 2.

7. The compound according to claim 1 or a salt thereof, wherein $R^3$ is an optionally substituted $C_{1-6}$ alkyl group, an optionally substituted $C_{3-8}$ cycloalkyl group or an optionally substituted heterocyclic group;

$X^1$ is a group represented by the general formula $C(=O)N(R^{6b})$ wherein the carbon atom is bonded to ring A, and $R^{6b}$ represents an optionally substituted $C_{1-3}$ alkyl group;

m number of $R^4$ are the same or different and each are a halogen atom or an optionally substituted $C_{1-3}$ alkyl group; and m is an integer of 0 to 2.

8. The compound according to claim 7 or a salt thereof, wherein m number of $R^4$ are the same or different and each are a halogen atom; and m is an integer of 0 to 2.

9. The compound according to claim 1 or a salt thereof, wherein $X^1$ is a group represented by the general formula $N(R^7)C(=O)$ wherein the nitrogen atom is bonded to ring A, and $R^7$ represents a hydrogen atom, an amino-protective group or an optionally substituted $C_{1-6}$ alkyl group; or $R^7$ represents, together with one substituent $R^4$ on ring A, an optionally substituted $C_{2-4}$ alkylene group, a group represented by the general formula $O$—$Y^1$ wherein the oxygen atom is bonded to ring A, and $Y^1$ represents an optionally substituted $C_{1-3}$ alkylene group, a group represented by the general formula $S(O)_n$—$Y^2$ wherein the sulfur atom is bonded to ring A, $Y^2$ represents an optionally substituted $C_{1-3}$ alkylene group, and n represents an integer of 0 to 2, or a group represented by the general formula $N(R^8)$—$Y^3$ wherein the nitrogen atom is bonded to ring A, $Y^3$ represents an optionally substituted $C_{1-3}$ alkylene group, and $R^8$ represents a hydrogen atom, an amino-protective group, an optionally substituted $C_{1-6}$ alkyl group or an optionally substituted aryl group.

10. The compound according to claim 1 or a salt thereof, wherein $R^3$ is an optionally substituted $C_{1-6}$ alkyl group, an optionally substituted $C_{3-8}$ cycloalkyl group or an optionally substituted heterocyclic group;

$X^1$ is a group represented by the general formula $N(R^{7a})C(=O)$ wherein the nitrogen atom is bonded to ring A, and $R^{7a}$ represents an optionally substituted $C_{1-3}$ alkyl group, or $R^{7a}$ represents, together with one substituent $R^4$ on ring A, an optionally substituted $C_{2-3}$ alkylene group or a group represented by the general formula $O$—$Y^{1a}$ wherein the oxygen atom is bonded to ring A, and $Y^{1a}$ represents an ethylene group;

m number of $R^4$ are the same or different and each are a halogen atom, an optionally substituted $C_{1-3}$ alkyl group, an optionally substituted $C_{1-3}$ alkylsulfonyl group, an optionally substituted $C_{2-3}$ alkylene group formed together by two adjacent $R^4$, an optionally substituted $C_{2-3}$ alkylene group formed together by one $R^4$ and $R^{7a}$, or a group represented by the general formula $O$—$Y^{1a}$ formed together by one $R^4$ and $R^{7a}$ wherein the oxygen atom is bonded to ring A, and $Y^{1a}$ represents an ethylene group; and m is an integer of 0 to 2.

11. The compound according to claim 1 or a salt thereof, wherein $R^3$ is an optionally substituted heterocyclic group;

$X^1$ is a group represented by the general formula $N(R^{7b})C(=O)$ wherein the nitrogen atom is bonded to ring A, and $R^{7b}$ represents an optionally substituted $C_{1-3}$ alkyl group, or $R^{7b}$ represents, together with one substituent $R^4$ on ring A, an optionally substituted $C_{2-3}$ alkylene group;

m number of $R^4$ are the same or different and each are an optionally substituted $C_{1-3}$ alkyl group, an optionally substituted $C_{2-3}$ alkylene group formed together by two adjacent $R^4$, or an optionally substituted $C_{2-3}$ alkylene group formed together by one $R^4$ and $R^{7b}$; and m is an integer of 0 to 2.

12. The compound according to claim 11 or a salt thereof, wherein $X^1$ is a group represented by the general formula $N(R^{7b})C(=O)$ wherein the nitrogen atom is bonded to ring A, and $R^{7b}$ represents an optionally substituted $C_{1-3}$ alkyl group, or $R^{7b}$ represents, together with one substituent $R^4$ on ring A, an optionally substituted $C_{2-3}$ alkylene group;

m number of $R^4$ are the same or different and each are an optionally substituted $C_{1-3}$ alkyl group, or an optionally substituted $C_{2-3}$ alkylene group formed together by one $R^4$ and $R^{7b}$; and m is an integer of 0 to 2.

13. The compound according to claim 1 or a salt thereof, wherein $X^1$ is an optionally substituted divalent cyclic hydrocarbon group resulting from the removal of one hydrogen atom from each of two adjacent atoms or an optionally substituted divalent heterocyclic group resulting from the removal of one hydrogen atom from each of two adjacent atoms.

14. The compound according to claim 1 or a salt thereof, wherein
- $R^3$ is an optionally substituted $C_{1-6}$ alkyl group or an optionally substituted heterocyclic group;
- $X^1$ is an optionally substituted divalent cyclic hydrocarbon group resulting from the removal of one hydrogen atom from each of two adjacent atoms or an optionally substituted divalent heterocyclic group resulting from the removal of one hydrogen atom from each of two adjacent atoms;
- m number of $R^4$ are the same or different and each are a halogen atom; and
- m is an integer of 0 to 2.

15. The compound according to claim 14 or a salt thereof, wherein
- $R^3$ is an optionally substituted heterocyclic group; and
- $X^1$ is an optionally substituted divalent heterocyclic group resulting from the removal of one hydrogen atom from each of two adjacent atoms.

16. A pharmaceutical composition comprising a compound according to claim 1 or a salt thereof.

17. An agent for treatment of an immune disease, comprising a compound according to claim 1 or a salt thereof.

* * * * *